(12) United States Patent
Uchikawa et al.

(10) Patent No.: US 8,273,761 B2
(45) Date of Patent: Sep. 25, 2012

(54) TRICYCLIC COMPOUND AND MEDICAL USE THEREOF

(75) Inventors: Osamu Uchikawa, Osaka (JP); Tatsuki Koike, Osaka (JP); Takafumi Takai, Osaka (JP); Yasutaka Hoashi, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 446 days.

(21) Appl. No.: 12/448,094

(22) PCT Filed: Dec. 7, 2007

(86) PCT No.: PCT/JP2007/073680
§ 371 (c)(1),
(2), (4) Date: Jul. 2, 2009

(87) PCT Pub. No.: WO2008/069311
PCT Pub. Date: Jun. 12, 2008

(65) Prior Publication Data
US 2010/0029707 A1     Feb. 4, 2010

(30) Foreign Application Priority Data
Dec. 8, 2006 (JP) .................. 2006-332647

(51) Int. Cl.
*C07D 491/048* (2006.01)
*A61K 31/4355* (2006.01)
(52) U.S. Cl. .................. 514/293; 514/294; 546/83
(58) Field of Classification Search .............. 546/83; 514/293, 294
See application file for complete search history.

(56) References Cited

U.S. PATENT DOCUMENTS

| | | | |
|---|---|---|---|
| 5,633,276 A | 5/1997 | North et al. | |
| 5,843,986 A | 12/1998 | Lesieur et al. | |
| 5,998,461 A | 12/1999 | Lesieur et al. | |
| 6,034,239 A | 3/2000 | Ohkawa et al. | |
| 6,218,429 B1 | 4/2001 | Ohkawa et al. | |

FOREIGN PATENT DOCUMENTS

| | | |
|---|---|---|
| JP | 11-152281 | 6/1999 |
| WO | 97/32871 | 9/1997 |
| WO | 2006/027474 A2 | 3/2006 |
| WO | 2006/027474 A3 | 3/2006 |

OTHER PUBLICATIONS

Dorwald F. A. Side Reactions in Organic Synthesis, 2005, Wiley: VCH, Weinheim p. IX of Preface.*
Supplementary European Search Report dated Nov. 23, 2009 in European Application No. EP 07 85 0267.
Benckova et al., 5-Aminofuro[3,2-*c*]Pyridinium tosylates and Substituted Furo[3,2-*c*]Pyridine N-Oxides: Synthesis and Reactions, *Collection of Czechoslovak Chemical Communications*, vol. 64, No. 3, pp. 539-547, 1999.
Elsner et al., Bicyclic melatonin receptor agonists containing a ring-junction nitrogen: Synthesis, biological evaluation, and molecular modeling of the putative bioactive conformation, *Bioorganic & Medicinal Chemistry*, vol. 14, pp. 1949-1958, 2006.

* cited by examiner

*Primary Examiner* — Rita Desai
(74) *Attorney, Agent, or Firm* — Wenderoth, Lind & Ponack, L.L.P.

(57) ABSTRACT

The present invention provides a compound represented by the formula

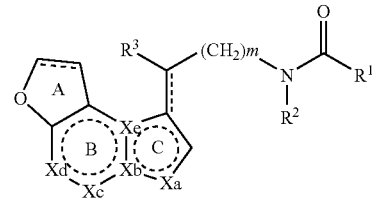

wherein $R^1$ is a hydrocarbon group optionally having substituent(s), amino optionally having substituent(s), hydroxy optionally having a substituent or a heterocyclic group optionally having substituent(s), $R^2$ is a hydrogen atom or a hydrocarbon group optionally having substituent(s), $R^3$ is a hydrogen atom, a halogen atom, a hydrocarbon group optionally having substituent(s), amino optionally having substituent(s), hydroxy optionally having a substituent or mercapto optionally having a substituent, Xa to Xe are each a carbon atom or a nitrogen atom, m is 0 to 2, and ring A to ring C are each a ring optionally having substituent(s), or a salt thereof, which is useful as an agent for the prophylaxis or treatment of a disease relating to an action of melatonin, and the like.

10 Claims, No Drawings

SEQUENCE LISTING

<160> NUMBER OF SEQ ID NOS: 2

<210> SEQ ID NO 1
<211> LENGTH: 1053
<212> TYPE: DNA
<213> ORGANISM: Homo sapiens

<400> SEQUENCE: 1

| | | | | | |
|---|---|---|---|---|---|
| atgcagggca | acggcagcgc | gctgcccaac | gcctcccagc | ccgtgctccg | cggggacggc | 60 |
| gcgcggccct | cgtggctggc | gtccgccctg | gcctgcgtcc | tcatcttcac | catcgtggtg | 120 |
| gacatcctgg | gcaacctcct | ggtcatcctg | tcggtgtatc | ggaacaagaa | gctcaggaac | 180 |
| gcaggaaaca | tctttgtggt | gagcttagcg | gtggcagacc | tggtggtggc | catttatccg | 240 |
| tacccgttgg | tgctgatgtc | gatatttaac | aacgggtgga | acctgggcta | tctgcactgc | 300 |
| caagtcagtg | ggttcctgat | gggcctgagc | gtcatcggct | ccatattcaa | catcaccggc | 360 |
| atcgccatca | accgctactg | ctacatctgc | cacagtctca | agtacgacaa | actgtacagc | 420 |
| agcaagaact | ccctctgcta | cgtgctcctc | atatggctcc | tgacgctggc | ggccgtcctg | 480 |
| cccaacctcc | gtgcagggac | tctccagtac | gacccgagga | tctactcgtg | caccttcgcc | 540 |
| cagtccgtca | gctccgccta | caccatcgcc | gtggtggttt | tccacttcct | cgtcccccatg | 600 |
| atcatagtca | tcttctgtta | cctgagaata | tggatcctgg | ttctccaggt | cagacagagg | 660 |
| gtgaaacctg | accgcaaacc | caaactgaaa | ccacaggact | tcaggaattt | tgtcaccatg | 720 |
| tttgtggttt | ttgtcctttt | tgccatttgc | tgggctcctc | tgaacttcat | tggcctggcc | 780 |
| gtggcctctg | accccgccag | catggtgcct | aggatcccag | agtggctgtt | tgtggccagt | 840 |
| tactacatgg | cgtatttcaa | cagctgcctc | aatgccatta | tatacgggct | actgaaccaa | 900 |
| aatttcagga | aggaatacag | gagaattata | gtctcgctct | gtacagccag | ggtgttcttt | 960 |
| gtggacagct | ctaacgacgt | ggccgatagg | gttaaatgga | aaccgtctcc | actgatgacc | 1020 |
| aacaataatg | tagtaaaggt | ggactccgtt | taa | | | 1053 |

<210> SEQ ID NO 2
<211> LENGTH: 1089
<212> TYPE: DNA
<213> ORGANISM: Homo sapiens

<400> SEQUENCE: 2

| | | | | | |
|---|---|---|---|---|---|
| atgtcagaga | acggctcctt | cgccaactgc | tgcgaggcgg | gcgggtgggc | agtgcgcccg | 60 |
| ggctggtcgg | gggctggcag | cgcgcggccc | tccaggaccc | ctcgacctcc | ctgggtggct | 120 |
| ccagcgctgt | ccgcggtgct | catcgtcacc | accgccgtgg | acgtcgtggg | caacctcctg | 180 |
| gtgatcctct | ccgtgctcag | gaaccgcaag | ctccggaacg | caggtaattt | gttcttggtg | 240 |
| agtctggcat | tggctgacct | ggtggtggcc | ttctacccct | acccgctaat | cctcgtggcc | 300 |
| atcttctatg | acggctgggc | cctggggag | gagcactgca | aggccagcgc | ctttgtgatg | 360 |
| ggcctgagcg | tcatcggctc | tgtcttcaat | atcactgcca | tcgccattaa | ccgctactgc | 420 |
| tacatctgcc | acagcatggc | ctaccaccga | atctaccggc | gctggcacac | ccctctgcac | 480 |
| atctgcctca | tctggctcct | caccgtggtg | gccttgctgc | caacttctt | tgtgggtcc | 540 |
| ctggagtacg | acccacgcat | ctattcctgc | accttcatcc | agaccgccag | cacccagtac | 600 |
| acggcggcag | tggtggtcat | ccacttcctc | ctccctatcg | ctgtcgtgtc | cttctgctac | 660 |
| ctgcgcatct | gggtgctggt | gcttcaggcc | cgcaggaaag | ccaagccaga | gagcaggctg | 720 |

-continued

```
tgcctgaagc ccagcgactt gcggagcttt ctaaccatgt ttgtggtgtt tgtgatcttt    780
gccatctgct gggctccact taactgcatc ggcctcgctg tggccatcaa cccccaagaa    840
atggctcccc agatccctga ggggctattt gtcactagct acttactggc ttatttcaac    900
agctgcctga atgccattgt ctatgggctc ttgaaccaaa acttccgcag ggaatacaag    960
aggatcctct tggccctttg gaacccacgg cactgcattc aagatgcttc caagggcagc   1020
cacgcggagg ggctgcagag cccagctcca cccatcattg gtgtgcagca ccaggcagat   1080
gctctctag                                                           1089
```

TRICYCLIC COMPOUND AND MEDICAL USE THEREOF

This application is a U.S. national stage of International Application No. PCT/JP2007/073680, filed Dec. 7, 2007.

TECHNICAL FIELD

The present invention relates to a tricyclic compound having superior affinity for melatonin receptor, and useful as an agent for the prophylaxis or treatment of a disease related to the action of melatonin.

BACKGROUND OF THE INVENTION

Melatonin (N-acetyl-5-methoxytryptamine), which is a hormone synthesized and secreted principally in the pineal gland, increases in dark environments and decreases in light environments. Melatonin acts suppressively on pigment cells and the female gonads, and acts as a synchronous factor of biological clock while taking part in transmittance of photo-periodic code. Therefore, melatonin is expected to be usable for the treatment of diseases related to melatonin activity, such as reproductive and endocrinic disorders, sleep-awake rhythm disorders, jet-lag syndrome, various disorders related to aging and the like. It has been clarified that the production amount of melatonin decreases with aging and there is a report documenting that retention of the production amount of melatonin could prevent aging itself [Ann. N.Y. Acad. Sci., vol. 719, pages 456-460, (1994) (non-patent document 1)]. However, since melatonin is easily metabolized by metabolic enzymes in vivo [Clinical Examinations, vol. 38, No. 11, pages 282-284 (1994) (non-patent document 2)]. Therefore, melatonin is not entirely suitable as a drug.

WO 97/32871 (patent document 1) and U.S. Pat. No. 6,034,239 (patent document 2) disclose a compound represented by the formula:

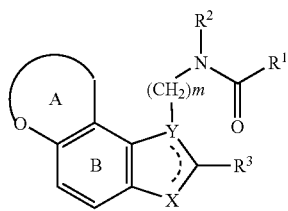

wherein $R^1$ represents an optionally substituted hydrocarbon group, an optionally substituted amino group or an optionally substituted heterocyclic group; $R^2$ represents a hydrogen atom or an optionally substituted hydrocarbon group; $R^3$ represents a hydrogen atom, an optionally substituted hydrocarbon group or an optionally substituted heterocyclic group; X represents $CHR^4$, $NR^4$, O or S wherein $R^4$ represents a hydrogen atom or an optionally substituted hydrocarbon group; Y represents C, CH or N, provided that when X is $CH_2$, Y is C or CH;

----- is a single bond or a double bond,
ring A represents an optionally substituted 5- to 7-membered oxygen-containing heterocyclic ring; ring B represents an optionally substituted benzene ring; and m represents an integer of 1 to 4, or a salt thereof and the like, which has an affinity for melatonin receptor and is useful as a therapeutic agent for sleep disorder and the like.

U.S. Pat. No. 5,633,276 (patent document 3) discloses a compound represented by the formula

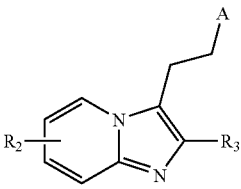

wherein $R^1$ represents hydrogen, halogen or $C_{1-6}$ alkyl; $R^2$ represents a group represented by $-CR^3R^4(CH_2)_p NR^5COR^6$; $R^3$, $R^4$ and $R^5$ are the same or different and each represents hydrogen or $C_{1-6}$ alkyl; $R^6$ represents $C_{1-6}$ alkyl or $C_{3-7}$ cycloalkyl; n represents 2, 3 or 4; and p represents 1, 2, 3 or 4, which is useful as a therapeutic agent for conditions associated with a disturbed functioning of the melatonin system and the like.

WO 2006/27474 (patent document 4) discloses a compound represented by the formula

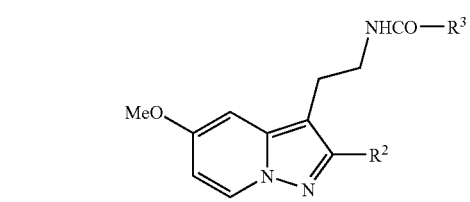

wherein A represents $-NHCOR_1$ or $-CONHR_1$; $R_1$ represents $C_{1-6}$ alkyl, $C_{3-6}$ cycloalkyl etc.; $R_2$ represents alkoxy; and $R_3$ represents aryl, arylalkyl or aroyl, which is useful as a therapeutic agent for conditions associated with a disturbed functioning of the melatonin system and the like.

Bioorganic & Medicinal Chemistry, vol. 14, pages 1949-1958 (2006) (non-patent document 3) discloses the following melatonin receptor agonist:

wherein $R^2$ represents H or Ph, and $R^3$ represents Me, Et or Pr.

U.S. Pat. No. 5,843,986 (patent document 5) and U.S. Pat. No. 5,998,461 (patent document 6) describe a tricyclic amide compound as a therapeutic agent for a disorder of the melatoninergic system.

patent document 1: WO 97/32871
patent document 2: U.S. Pat. No. 6,034,239
patent document 3: U.S. Pat. No. 5,633,276
patent document 4: WO 2006/27474
patent document 5: U.S. Pat. No. 5,843,986
patent document 6: U.S. Pat. No. 5,998,461
non-patent document 1: Ann. N.Y. Acad. Sci., vol. 719, pages 456-460 (1994)
non-patent document 2: Clinical Examinations, vol. 38, No. 11, pages 282-284 (1994)

non-patent document 3: Bioorganic & Medicinal Chemistry, vol. 14, pages 1949-1958 (2006)

DISCLOSURE OF THE INVENTION

Melatonin receptor agonists having different structures from that of melatonin, and having superior affinity for melatonin receptor, superior intracerebral mobility and superior metabolic stability are expected to be more effective for the treatment of sleep disorder and the like than melatonin. While the above-mentioned compounds and the like have been reported as melatonin receptor agonists, the development of a novel compound, which is different from the above-mentioned known compounds in the chemical structure, has superior agonistic activity for melatonin receptor, and is useful as a pharmaceutical product, is desired.

The present inventors have conducted various studies and first succeeded in the production of a novel compound represented by the following formula (I) and a salt thereof. They have further found that the compound and a salt thereof unexpectedly have superior properties as melatonin agonists and are useful as pharmaceutical agents and, based on these findings, completed the present invention.

Accordingly, the present invention relates to

[1] a compound represented by the formula:

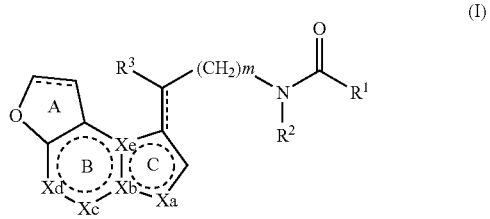

wherein $R^1$ is a hydrocarbon group optionally having substituent(s), amino optionally having substituent(s), hydroxy optionally having a substituent or a heterocyclic group optionally having substituent(s), $R^2$ is a hydrogen atom or a hydrocarbon group optionally having substituent(s), $R^3$ is a hydrogen atom, a halogen atom, a hydrocarbon group optionally having substituent(s), amino optionally having substituent(s), hydroxy optionally having a substituent or mercapto optionally having a substituent, Xa, Xb, Xc, Xd and Xe are each a carbon atom or a nitrogen atom, m is 0, 1 or 2, ring A is a 5-membered ring optionally having substituent(s),
ring B is a 6-membered ring optionally having substituent(s),
ring C is a 5-membered ring optionally having substituent(s), and ----- is a single bond or a double bond, provided at least one of Xb, Xc, Xd and Xe is a nitrogen atom and at least three of Xa, Xb, Xc, Xd and Xe are carbon atoms, or a salt thereof (hereinafter sometimes to be abbreviated as compound (I));

[2] the compound of the aforementioned [1], wherein the tricycle consisting of ring A, ring B and ring C is a ring represented by the formula

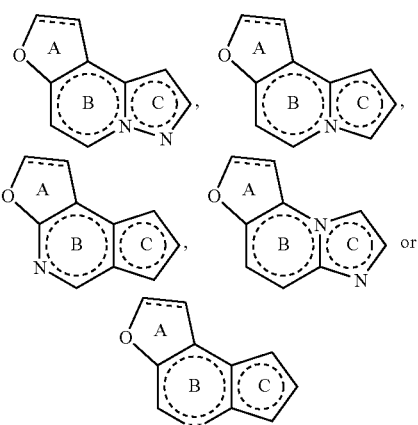

wherein each symbol is as defined in the aforementioned [1];

[3] the compound of the aforementioned [1], wherein $R^1$ is $C_{1-6}$ alkyl optionally having substituent(s), $C_{3-6}$ cycloalkyl optionally having substituent(s), $C_{2-6}$ alkenyl optionally having substituent(s), $C_{6-10}$ aryl optionally having substituent(s) or amino optionally having substituent(s);

[4] the compound of the aforementioned [1], wherein $R^2$ is a hydrogen atom or $C_{1-6}$ alkyl optionally having substituent(s);

[5] the compound of the aforementioned [1], wherein $R^3$ is a hydrogen atom or $C_{1-6}$ alkyl optionally having substituent(s);

[6] the compound of the aforementioned [1], wherein m is 1;

[7] the compound of the aforementioned [1], wherein ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;

[8] the compound of the aforementioned [1], wherein ring B is a 6-membered ring optionally having 1 or 2 substituents selected from a halogen atom, a hydrocarbon group optionally having substituent(s), amino optionally having substituent(s), hydroxy optionally having a substituent and mercapto optionally having a substituent;

[9] the compound of the aforementioned [1], wherein ring C is a 5-membered ring optionally having 1 or 2 substituents selected from a halogen atom, a hydrocarbon group optionally having substituent(s), hydroxy optionally having a substituent and a heterocyclic group optionally having substituent(s);

[10] the compound of the aforementioned [1], wherein $R^1$ is $C_{1-6}$ alkyl, $C_{3-6}$ cycloalkyl, $C_{6-10}$ aryl or mono-$C_{1-6}$ alkylamino;
$R^2$ is a hydrogen atom;
$R^3$ is a hydrogen atom or $C_{1-6}$ alkyl;
m is 1;
ring A is a 5-membered ring optionally having one $C_{1-6}$ alkyl;
ring B is an unsubstituted 6-membered ring;
ring C is a 5-membered ring optionally having one substituent selected from (1) $C_{1-6}$ alkyl optionally having 1 to 3 halogen atoms, (2) $C_{3-6}$ cycloalkyl and (3) $C_{6-10}$ aryl optionally having 1 to 3 halogen atoms;
Xa is CH, $CH_2$ or N;
Xb is C or N;
Xc is CH or N;
Xd is CH or N; and
Xe is C or N;

[11] N-[2-(8,9-dihydrofuro[3,2-c]pyrazolo[1,5-a]pyridin-1-yl)ethyl]acetamide, N-[2-(2-ethyl-8,9-dihydrofuro[3,2-c]

pyrazolo[1,5-a]pyridin-1-yl)ethyl]acetamide, N-[2-(2-ethyl-8,9-dihydrofuro[3,2-c]pyrazolo[1,5-a]pyridin-1-yl)ethyl]propanamide, N-[2-(2-methyl-8,9-dihydrofuro[3,2-c]pyrazolo[1,5-a]pyridin-1-yl)ethyl]acetamide, N-{2-[2-(trifluoromethyl)-8,9-dihydrofuro[3,2-c]pyrazolo[1,5-a]pyridin-1-yl]ethyl}acetamide, N-[2-(1,6,7,8-tetrahydro-2H-cyclopenta[d]furo[2,3-b]pyridin-8-yl)ethyl]acetamide, N-[2-(1,6,7,8-tetrahydro-2H-cyclopenta[d]furo[2,3-b]pyridin-8-yl)ethyl]propanamide, N-[2-(7-phenyl-1,2-dihydrofuro[2,3-e]imidazo[1,2-a]pyridin-8-yl)ethyl]acetamide, N-[2-(2-phenyl-8,9-dihydrofuro[3,2-c]pyrazolo[1,5-a]pyridin-1-yl)ethyl]acetamide, or N-[2-(2-ethyl-8,9-dihydrofuro[3,2-c]pyrazolo[1,5-a]pyridin-1-yl)propyl]acetamide, or a salt thereof;

[12] a prodrug of the compound of the aforementioned [1];

[13] a pharmaceutical composition comprising the compound of the aforementioned [1] or a prodrug thereof;

[14] the pharmaceutical composition of the aforementioned [13], which is a melatonin receptor agonist;

[15] the pharmaceutical composition of the aforementioned [13], which is an agent for the prophylaxis or treatment of sleep disorder;

[16] a compound represented by the formula

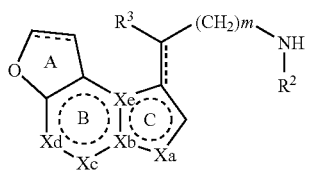

wherein
R² is a hydrogen atom or a hydrocarbon group optionally having substituent(s),
R³ is a hydrogen atom, a halogen atom, a hydrocarbon group optionally having substituent(s), amino optionally having substituent(s), hydroxy optionally having a substituent or mercapto optionally having a substituent,
Xa, Xb, Xc, Xd and Xe are each a carbon atom or a nitrogen atom,
m is 0, 1 or 2,
ring A is a 5-membered ring optionally having substituent(s),
ring B is a 6-membered ring optionally having substituent(s),
ring C is a 5-membered ring optionally having substituent(s), and
----- is a single bond or a double bond,
provided at least one of Xb, Xc, Xd and Xe is a nitrogen atom, and at least three of Xa, Xb, Xc, Xd and Xe are carbon atoms, or a salt thereof;

[17] a method for preventing or treating sleep disorder in a mammal, comprising administering an effective amount of the compound of the aforementioned [1] or a salt thereof or a prodrug thereof to the mammal;

[18] use of the compound of the aforementioned [1] or a salt thereof or a prodrug thereof for producing an agent for the prophylaxis or treatment of sleep disorder, and the like.

Moreover, the present invention relates to a melatonin receptor agonist, an agent for the prophylaxis or treatment of sleep disorder and the like, which comprise a compound represented by the formula

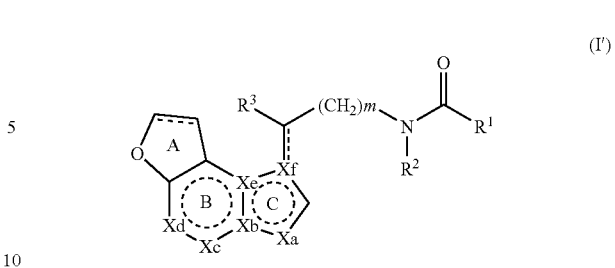

wherein R¹ is a hydrocarbon group optionally having substituent(s), amino optionally having substituent(s) or a heterocyclic group optionally having substituent(s),
R² is a hydrogen atom or a hydrocarbon group optionally having substituent(s),
R³ is a hydrogen atom, a halogen atom, a hydrocarbon group optionally having substituent(s), amino optionally having substituent(s), hydroxy optionally having a substituent or mercapto optionally having a substituent,
Xa, Xb, Xc, Xd, Xe and Xf are each a carbon atom or a nitrogen atom,
m is 0, 1 or 2,
ring A is a 5-membered ring optionally having substituent(s),
ring B is a 6-membered ring optionally having substituent(s),
ring C is a 5-membered ring optionally having substituent(s), and
----- is a single bond or a double bond,
or a salt thereof (hereinafter sometimes to be abbreviated as compound (I')).

Since compound (I) and compound (I') show superior affinity for melatonin receptors, superior pharmacokinetics (e.g., metabolic stability) and the like, a clinically useful agent for the prophylaxis or treatment of diseases related to the action of melatonin in the living body can be provided.

As the "halogen atom" used in the present specification, fluorine, chlorine, bromine or iodine can be mentioned.

As the "hydrocarbon group" of the term "hydrocarbon group optionally having substituent(s)" used in the present specification, for example, aliphatic hydrocarbon group, monocyclic saturated hydrocarbon group and aromatic hydrocarbon group and the like can be mentioned, with preference given to those having 1 to 16 carbon atoms. Specifically, for example, alkyl, alkenyl, alkynyl, cycloalkyl, aryl and the like are used.

The "alkyl" is preferably, for example, lower alkyl or the like, and, for example, $C_{1-6}$ alkyl such as methyl, ethyl, propyl, isopropyl, butyl, isobutyl, sec-butyl, tert-butyl, pentyl, hexyl etc., and the like are widely used.

The "alkenyl" is preferably, for example, lower alkenyl or the like, and, for example, $C_{2-6}$ alkenyl such as vinyl, 1-propenyl, allyl, isopropenyl, butenyl, isobutenyl etc., and the like are widely used.

The "alkynyl" is preferably, for example, lower alkynyl or the like, and, for example, $C_{2-6}$ alkynyl such as ethynyl, propargyl, 1-propynyl etc., and the like are widely used.

The "cycloalkyl" is preferably, for example, lower cycloalkyl or the like, and, for example, $C_{3-6}$ cycloalkyl such as cyclopropyl, cyclobutyl, cyclopentyl and cyclohexyl, and the like are widely used.

The "aryl" is preferably, for example, $C_{6-14}$ aryl such as phenyl, 1-naphthyl, 2-naphthyl, biphenylyl, 2-anthryl etc., or the like, more preferably $C_{6-10}$ aryl, and, for example, phenyl and the like are widely used.

As the substituent which the "hydrocarbon group" of the "hydrocarbon group optionally having substituent(s)" may have, for example, (1) halogen atom (e.g., fluorine, chlorine, bromine, iodine),
(2) nitro,
(3) cyano,
(4) hydroxy,
(5) lower alkyl optionally having substituent(s) (e.g., $C_{1-6}$ alkyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, methyl, chloromethyl, difluoromethyl, trichloromethyl, trifluoromethyl, ethyl, 2-bromoethyl, 2,2,2-trifluoroethyl, pentafluoroethyl, propyl, 3,3,3-trifluoropropyl, isopropyl, butyl, isobutyl, sec-butyl, tert-butyl, 4,4,4-trifluorobutyl, pentyl, isopentyl, neopentyl, 5,5,5-trifluoropentyl, hexyl, 6,6,6-trifluorohexyl and the like),
(6) lower alkoxy optionally having substituent(s) (e.g., $C_{1-6}$ alkoxy optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkoxy such as methoxy, ethoxy, propoxy, isopropoxy, butoxy, isobutoxy, pentyloxy, hexyloxy, trifluoromethoxy etc., and the like),
(7) amino,
(8) mono-lower alkylamino optionally having substituent(s) (e.g., mono-$C_{1-6}$ alkylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, mono-$C_{1-6}$ alkylamino such as methylamino, ethylamino, propylamino, isopropylamino, butylamino etc., and the like),
(9) di-lower alkylamino optionally having substituent(s) (e.g., di-$C_{1-6}$ alkylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkylamino such as dimethylamino, diethylamino, dipropylamino, diisopropylamino, dibutylamino, N-ethyl-N-methylamino etc., and the like),
(10) carboxy,
(11) lower alkylcarbonyl optionally having substituent(s) (e.g., $C_{1-6}$ alkyl-carbonyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{1-6}$ alkyl-carbonyl such as acetyl, propionyl etc., and the like),
(12) lower alkoxycarbonyl optionally having substituent(s) (e.g., $C_{1-6}$ alkoxy-carbonyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{1-6}$ alkoxy-carbonyl such as methoxycarbonyl, ethoxycarbonyl, propoxycarbonyl, butoxycarbonyl etc., and the like),
(13) carbamoyl,
(14) mono-lower alkylcarbamoyl optionally having substituent(s) (e.g., mono-$C_{1-6}$ alkyl-carbamoyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, mono-$C_{1-6}$ alkyl-carbamoyl such as methylcarbamoyl, ethylcarbamoyl etc., and the like),
(15) di-lower alkylcarbamoyl optionally having substituent(s) (e.g., di-$C_{1-6}$ alkyl-carbamoyl optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, di-$C_{1-6}$ alkyl-carbamoyl such as dimethylcarbamoyl, diethylcarbamoyl, ethylmethylcarbamoyl etc., and the like),
(16) arylcarbamoyl optionally having substituent(s) (e.g., $C_{6-10}$ aryl-carbamoyl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryl-carbamoyl such as phenylcarbamoyl, naphthylcarbamoyl etc., and the like),
(17) aryl optionally having substituent(s) (e.g., $C_{6-10}$ aryl optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, phenyl, naphthyl and the like),
(18) aryloxy optionally having substituent(s) (e.g., $C_{6-10}$ aryloxy optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, $C_{6-10}$ aryloxy such as phenyloxy, naphthyloxy etc., and the like),
(19) lower alkyl-carbonylamino optionally having substituent(s) (e.g., $C_{1-6}$ alkyl-carbonylamino optionally having 1 to 5 substituents selected from a halogen atom, nitro, cyano, hydroxy, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino and the like; for example, optionally halogenated $C_{1-6}$ alkyl-carbonylamino such as acetylamino, trifluoroacetylamino etc., and the like),

(20) oxo,

(21) cycloalkyl (e.g., $C_{3-6}$ cycloalkyl such as cyclopropyl, cyclobutyl, cyclopentyl, cyclohexyl etc., and the like),

(22) lower alkynyl (e.g., $C_{2-6}$ alkynyl such as ethynyl, 1-propynyl, propargyl etc., and the like),

(23) lower alkenyl (e.g., $C_{2-6}$ alkenyl such as vinyl, allyl, isopropenyl, butenyl, isobutenyl etc., and the like),

(24) aralkyl (e.g., $C_{7-12}$ aralkyl such as benzyl, α-methylbenzyl, phenethyl etc., and the like),

(25) formyl,

(26) arylcarbonyl (e.g., $C_{6-10}$ aryl-carbonyl such as benzoyl, naphthoyl etc., and the like),

(27) lower alkanoyloxy (e.g., formyloxy; $C_{1-6}$ alkyl-carbonyloxy such as acetyloxy, propionyloxy, butyryloxy, isobutyryloxy etc., and the like),

(28) arylcarbonyloxy (e.g., $C_{6-10}$ aryl-carbonyloxy such as benzoyloxy, naphthoyloxy etc., and the like),

(29) aralkyloxycarbonyl (e.g., $C_{7-12}$ aralkyloxy-carbonyl such as benzyloxycarbonyl etc., and the like),

(30) amidino,

(31) imino,

(32) 3- to 6-membered cyclic amino optionally containing, besides a carbon atom and one nitrogen atom, 1 to 3 hetero atoms selected from a nitrogen atom, an oxygen atom and a sulfur atom and optionally having substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom and optionally having 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),

(33) alkylenedioxy (e.g., $C_{1-3}$ alkylenedioxy such as methylenedioxy, ethylenedioxy etc., and the like),

(34) mercapto,

(35) sulfo,

(36) sulfino,

(37) phosphono,

(38) sulfamoyl,

(39) mono-lower alkylsulfamoyl (e.g., mono-$C_{1-6}$ alkylsulfamoyl such as N-methylsulfamoyl, N-ethylsulfamoyl, N-propylsulfamoyl, N-isopropylsulfamoyl, N-butylsulfamoyl etc., and the like),

(40) di-lower alkylsulfamoyl (e.g., di-$C_{1-6}$ alkylsulfamoyl such as N,N-dimethylsulfamoyl, N,N-diethylsulfamoyl, N,N-dipropylsulfamoyl, N,N-dibutylsulfamoyl etc., and the like),

(41) lower alkylthio (e.g., $C_{1-6}$ alkylthio such as methylthio, ethylthio, propylthio, isopropylthio, butylthio, sec-butylthio, tert-butylthio etc., and the like),

(42) arylthio (e.g., $C_{6-10}$ arylthio such as phenylthio, naphthylthio etc., and the like),

(43) lower alkylsulfinyl (e.g., $C_{1-6}$ alkylsulfinyl such as methylsulfinyl, ethylsulfinyl, propylsulfinyl, butylsulfinyl etc., and the like),

(44) arylsulfinyl (e.g., $C_{6-10}$ arylsulfinyl such as phenylsulfinyl, naphthylsulfinyl etc., and the like),

(45) lower alkylsulfonyl (e.g., $C_{1-6}$ alkylsulfonyl such as methylsulfonyl, ethylsulfonyl, propylsulfonyl, butylsulfonyl etc., and the like),

(46) arylsulfonyl (e.g., $C_{6-10}$ arylsulfonyl such as phenylsulfonyl, naphthylsulfonyl etc., and the like) and the like are used. The "hydrocarbon group" of the "hydrocarbon group optionally having substituent(s)" may have 1 to 5, preferably 1 to 3, substituents selected from the aforementioned substituents at substitutable position(s) of the hydrocarbon group. When the number of substituents is two or more, each substituent may be the same or different.

As the "heterocyclic group" of the term "heterocyclic group optionally having substituent(s)" used in the present specification, for example, a 5- to 14-membered (preferably 5- to 10-membered) (monocyclic, bicyclic or tricyclic, preferably monocyclic or bicyclic) heterocyclic group containing, besides a carbon atom, 1 to 4 (preferably 1 to 3) hetero atoms of one or two kinds selected from a nitrogen atom, an oxygen atom and a sulfur atom, can be mentioned. For example, a 5-membered ring group containing, besides a carbon atom, 1 to 4 hetero atoms selected from a nitrogen atom, an oxygen atom and a sulfur atom, such as 2- or 3-thienyl, 2- or 3-furyl, 1-, 2- or 3-pyrrolyl, 1-, 2- or 3-pyrrolidinyl, 2-, 4- or 5-oxazolyl, 3-, 4- or 5-isoxazolyl, 2-, 4- or 5-thiazolyl, 3-, 4- or 5-isothiazolyl, 3-, 4- or 5-pyrazolyl, 2-, 3- or 4-pyrazolidinyl, 2-, 4- or 5-imidazolyl, 2- or 4-imidazolinyl, 1,2,3-triazolyl, 1,2,4-triazolyl, 1H- or 2H-tetrazolyl and the like; for example, a 6-membered ring group containing, besides a carbon atom, 1 to 4 hetero atoms selected from a nitrogen atom, an oxygen atom and a sulfur atom, such as 2-, 3- or 4-pyridyl, N-oxido-2-, 3- or 4-pyridyl, 2-, 4- or 5-pyrimidinyl, N-oxido-2-, 4- or 5-pyrimidinyl, thiomorpholinyl, morpholinyl, piperidino, 2-, 3- or 4-piperidyl, thiopyranyl, 1,4-oxazinyl, 1,4-thiazinyl, 1,3-thiazinyl, 1- or 2-piperazinyl, triazinyl, 3- or 4-pyridazinyl, pyrazinyl, N-oxido-3- or 4-pyridazinyl and the like; for example, a bicyclic or tricyclic fused ring group containing, besides a carbon atom, 1 to 4 hetero atoms selected from a nitrogen atom, an oxygen atom and a sulfur atom (preferably, a group formed by condensation of the aforementioned 5- or 6-membered ring with one or two 5- or 6-membered ring group(s) optionally containing, besides a carbon atom, 1 to 4 hetero atoms selected from a nitrogen atom, an oxygen atom and a sulfur atom), such as indolyl, benzofuryl, benzothiazolyl, benzoxazolyl, benzimidazolyl, quinolyl, isoquinolyl, phthalazinyl, quinazolinyl, quinoxalinyl, indolizinyl, quinolizinyl, 1,8-naphthyridinyl, dibenzofuranyl, carbazolyl, acridinyl, phenanthridinyl, chromanyl, phenothiazinyl, phenoxazinyl and the like; and the like are used. Of these, a 5- to 7-membered (preferably 5- or 6-membered) heterocyclic group containing, besides a carbon atom, 1 to 3 hetero atoms selected from a nitrogen atom, an oxygen atom and a sulfur atom is preferable.

As the substituent that the "heterocyclic group" of the "heterocyclic group optionally having substituent(s)" may have, the aforementioned "hydrocarbon group optionally having substituent(s)", and the groups recited as examples of the substituents that the "hydrocarbon group optionally having substituent(s)" may have can be mentioned. Particularly preferably, for example, (1) a halogen atom (e.g., fluorine, chlorine, bromine, iodine), (2) lower alkyl (e.g., $C_{1-6}$ alkyl such as methyl, ethyl, propyl, isopropyl, butyl, isobutyl, sec-butyl, tert-butyl, pentyl, hexyl etc., and the like),
(3) cycloalkyl (e.g., $C_{3-6}$ cycloalkyl such as cyclopropyl, cyclobutyl, cyclopentyl, cyclohexyl, and the like),
(4) lower alkynyl (e.g., $C_{2-6}$ alkynyl such as ethynyl, 1-propynyl, propargyl etc., and the like),
(5) lower alkenyl (e.g., $C_{2-6}$ alkenyl such as vinyl, allyl, isopropenyl, butenyl, isobutenyl etc., and the like),
(6) aralkyl (e.g., $C_{7-12}$ aralkyl such as benzyl, α-methylbenzyl, phenethyl etc., and the like),
(7) aryl (e.g., $C_{6-10}$ aryl such as phenyl, naphthyl etc., and the like, preferably phenyl),
(8) lower alkoxy (e.g., $C_{1-6}$ alkoxy such as methoxy, ethoxy, propoxy, isopropoxy, butoxy, isobutoxy, sec-butoxy, tert-butoxy etc., and the like),
(9) aryloxy (e.g., $C_{6-10}$ aryloxy such as phenoxy etc., and the like),
(10) lower alkanoyl (e.g., formyl; $C_{1-6}$ alkyl-carbonyl such as acetyl, propionyl, butyryl, isobutyryl etc., and the like),
(11) arylcarbonyl (e.g., $C_{6-10}$ aryl-carbonyl such as benzoyl, naphthoyl etc., and the like),
(12) lower alkanoyloxy (e.g., formyloxy; $C_{1-6}$ alkyl-carbonyloxy such as acetyloxy, propionyloxy, butyryloxy, isobutyryloxy etc., and the like),
(13) arylcarbonyloxy (e.g., $C_{6-10}$ aryl-carbonyloxy such as benzoyloxy, naphthoyloxy etc., and the like),
(14) carboxy,
(15) lower alkoxycarbonyl (e.g., $C_{1-6}$ alkoxy-carbonyl such as methoxycarbonyl, ethoxycarbonyl, propoxycarbonyl, isopropoxycarbonyl, butoxycarbonyl, isobutoxycarbonyl, tert-butoxycarbonyl etc., and the like),
(16) aralkyloxycarbonyl (e.g., $C_{7-12}$ aralkyloxy-carbonyl such as benzyloxycarbonyl etc., and the like),
(17) carbamoyl,
(18) lower halogenoalkyl (e.g., mono-, di- or tri-halogeno-$C_{1-6}$ alkyl such as chloromethyl, dichloromethyl, trifluoromethyl, 2,2,2-trifluoroethyl etc., and the like),
(19) oxo,
(20) amidino,
(21) imino,
(22) amino,
(23) mono-lower alkylamino (e.g., mono-$C_{1-6}$ alkylamino such as methylamino, ethylamino, propylamino, isopropylamino, butylamino etc., and the like),
(24) di-lower alkylamino (e.g., di-$C_{1-6}$ alkylamino such as dimethylamino, diethylamino, dipropylamino, diisopropylamino, dibutylamino, N-ethyl-N-methylamino etc., and the like),
(25) 3- to 6-membered cyclic amino optionally containing, besides a carbon atom and one nitrogen atom, 1 to 3 hetero atoms selected from a nitrogen atom, an oxygen atom and a sulfur atom, which optionally has substituent(s) (e.g., 3- to 6-membered cyclic amino optionally containing, besides a carbon atom and one nitrogen atom, 1 to 3 hetero atoms selected from a nitrogen atom, an oxygen atom and a sulfur atom, which optionally has 1 to 5 substituents selected from a halogen atom, nitro, cyano, hydroxy, optionally halogenated $C_{1-6}$ alkyl, optionally halogenated $C_{1-6}$ alkoxy, amino, mono-$C_{1-6}$ alkylamino, di-$C_{1-6}$ alkylamino, carboxy, $C_{1-6}$ alkyl-carbonyl, $C_{1-6}$ alkoxy-carbonyl, carbamoyl, mono-$C_{1-6}$ alkyl-carbamoyl, di-$C_{1-6}$ alkyl-carbamoyl, $C_{6-10}$ aryl-carbamoyl, $C_{6-10}$ aryl, $C_{6-10}$ aryloxy, optionally halogenated $C_{1-6}$ alkyl-carbonylamino, oxo and the like; for example, aziridinyl, azetidinyl, pyrrolidinyl, pyrrolinyl, pyrrolyl, imidazolyl, pyrazolyl, imidazolidinyl, piperidyl, morpholinyl, dihydropyridyl, tetrahydropyridyl, piperazinyl, N-methylpiperazinyl, N-ethylpiperazinyl and the like),
(26) alkylenedioxy (e.g., $C_{1-3}$ alkylenedioxy such as methylenedioxy, ethylenedioxy etc., and the like),
(27) hydroxy,
(28) nitro,
(29) cyano,
(30) mercapto,
(31) sulfo,
(32) sulfino,
(33) phosphono,
(34) sulfamoyl,
(35) mono-lower alkylsulfamoyl (e.g., mono-$C_{1-6}$ alkylsulfamoyl such as N-methylsulfamoyl, N-ethylsulfamoyl, N-propylsulfamoyl, N-isopropylsulfamoyl, N-butylsulfamoyl etc., and the like),
(36) di-lower alkylsulfamoyl (e.g., di-$C_{1-6}$ alkylsulfamoyl such as N,N-dimethylsulfamoyl, N,N-diethylsulfamoyl, N,N-dipropylsulfamoyl, N,N-dibutylsulfamoyl etc., and the like),
(37) lower alkylthio (e.g., $C_{1-6}$ alkylthio such as methylthio, ethylthio, propylthio, isopropylthio, butylthio, sec-butylthio, tert-butylthio etc., and the like),
(38) arylthio (e.g., $C_{6-10}$ arylthio such as phenylthio, naphthylthio etc., and the like),
(39) lower alkylsulfinyl (e.g., $C_{1-6}$ alkylsulfinyl such as methylsulfinyl, ethylsulfinyl, propylsulfinyl, butylsulfinyl etc., and the like),
(40) arylsulfinyl (e.g., $C_{6-10}$ arylsulfinyl such as phenylsulfinyl, naphthylsulfinyl etc., and the like),
(41) lower alkylsulfonyl (e.g., $C_{1-6}$ alkylsulfonyl such as methylsulfonyl, ethylsulfonyl, propylsulfonyl, butylsulfonyl etc., and the like),
(42) arylsulfonyl (e.g., $C_{6-10}$ arylsulfonyl such as phenylsulfonyl, naphthylsulfonyl etc., and the like) and the like are used. The "heterocyclic group" of the "heterocyclic group optionally having substituent(s)" may have 1 to 5, preferably 1 to 3, substituents selected from the aforementioned substituents, at substitutable position(s) of the heterocyclic group. When the number of the substituents is two or more, each substituent may be the same or different.

The term used in the present specification "amino optionally having substituent(s)" means amino optionally having, as substituent, 1 or 2, the same or different groups selected from, for example, the aforementioned "hydrocarbon group optionally having substituent(s)", and the groups recited as examples of the substituent that the "hydrocarbon group optionally having substituent(s)" may have and the like. Preferable examples of the substituent that the "amino" may have include $C_{1-6}$ alkyl optionally having substituent(s), $C_{6-10}$ aryl optionally having substituent(s) and the like. As the substituent that the "$C_{1-6}$ alkyl" and "$C_{6-10}$ aryl" may have, those similar to the substituents that the aforementioned "hydrocarbon group" may have are used.

The term used in the present specification "hydroxy optionally having a substituent" means (1) hydroxy or (2) hydroxy having, instead of the hydrogen atom of hydroxy, one group selected from, for example, the aforementioned "hydrocarbon group optionally having substituent(s)", the groups recited as examples of the substituent that the "hydrocarbon group optionally having substituent(s)" may have and the like. As the "hydroxy optionally having a substituent", for example, hydroxy, $C_{1-6}$ alkoxy optionally having substituent(s), $C_{2-6}$ alkenyloxy optionally having substituent(s), $C_{2-6}$ alkynyloxy optionally having substituent(s), $C_{3-6}$ cycloalkyloxy optionally having substituent(s), $C_{6-14}$ aryloxy optionally having substituent(s) and the like can be mentioned.

Preferred are hydroxy, $C_{1-6}$ alkoxy optionally having substituent(s), $C_{6-14}$ aryloxy optionally having substituent(s) and the like. As the substituent that the "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, those similar to the substituents that the aforementioned "hydrocarbon group" may have are used.

The term used in the present specification "mercapto optionally having a substituent" means (1) mercapto or (2) mercapto having, instead of the hydrogen atom of mercapto, one group selected from, for example, the aforementioned "hydrocarbon group optionally having substituent(s)", the groups recited as examples of the substituent that the "hydrocarbon group optionally having substituent(s)" may have and the like. As the "mercapto optionally having a substituent", for example, mercapto, $C_{1-6}$ alkylthio optionally having substituent(s), $C_{2-6}$ alkenylthio optionally having substituent(s), $C_{2-6}$ alkynylthio optionally having substituent(s), $C_{3-6}$ cycloalkylthio optionally having substituent(s), $C_{6-14}$ arylthio optionally having substituent(s) and the like can be mentioned. Preferred are mercapto, $C_{1-6}$ alkylthio optionally having substituent(s), $C_{6-14}$ arylthio optionally having substituent(s) and the like. As the substituent that the "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, those similar to the substituents that the aforementioned "hydrocarbon group" may have are used.

As the "lower alkyl" of the term "lower alkyl optionally having substituent(s)" used in the present specification, for example, $C_{1-6}$ alkyl such as methyl, ethyl, propyl, isopropyl, butyl, isobutyl, sec-butyl, tert-butyl etc., and the like can be mentioned. The "lower alkyl" may have, as the substituent, for example, 1 to 3 substituents that the aforementioned "hydrocarbon group" may have, and the like.

In the aforementioned formulas, $R^1$ is a hydrocarbon group optionally having substituent(s), amino optionally having substituent(s), hydroxy optionally having a substituent or a heterocyclic group optionally having substituent(s).

Preferable examples of the "hydrocarbon group" of the "hydrocarbon group optionally having substituent(s)" for $R^1$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl, ethyl, propyl etc., and the like), alkenyl (e.g., $C_{2-6}$ alkenyl such as vinyl etc., and the like), cycloalkyl (e.g., $C_{3-6}$ cycloalkyl such as cyclopropyl etc., and the like), phenyl and the like. The "alkyl", "alkenyl", "alkynyl", "cycloalkyl" and "aryl" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; hydroxy; and the like), and the like.

As the substituent of the "amino optionally having substituent(s)" for $R^1$, preferably, for example, 1 or 2 from lower alkyl optionally having substituent(s), aryl optionally having substituent(s) and the like are used, and particularly, one from lower alkyl optionally having substituent(s) and the like is used. The "lower alkyl" optionally has, for example, 1 to 3 from the substituents that the aforementioned "hydrocarbon group" optionally has and the like. Examples of the "aryl" include $C_{6-10}$ aryl such as phenyl etc., and the like are used. The "aryl" optionally has, for example, 1 to 5, preferably 1 to 3, from the substituents that the aforementioned "hydrocarbon group" optionally has (preferably, a halogen atom such as fluorine, chlorine etc.; $C_{1-6}$ alkoxy such as methoxy, ethoxy etc.; and the like). Examples of the "amino optionally having substituent(s)" include $C_{6-10}$ arylamino (e.g., phenylamino and the like) optionally having 1 to 3 $C_{1-6}$ alkoxy (e.g., methoxy and the like), mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like, and mono-$C_{1-6}$ alkylamino (e.g., ethylamino and the like) is particularly preferably used.

Preferable examples of the "hydroxy optionally having a substituent" for $R^1$ include hydroxy, $C_{1-6}$ alkoxy (e.g., methoxy, ethoxy, propoxy, isopropoxy, tert-butoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like, particularly, $C_{1-6}$ alkoxy (e.g., methoxy, tert-butoxy and the like) optionally having substituent(s), $C_{2-6}$ alkenyloxy (e.g., vinyloxy and the like) optionally having substituent(s), $C_{3-6}$ cycloalkyloxy (e.g., cyclopropyloxy and the like) optionally having substituent(s) and the like can be mentioned. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" optionally have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

Preferable examples of the "heterocyclic group" of the "heterocyclic group optionally having substituent(s)" for $R^1$ include a 5- or 6-membered heterocyclic group containing, besides a carbon atom, 1 to 3 hetero atoms selected from a nitrogen atom, an oxygen atom and a sulfur atom, and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, 6-membered nitrogen-containing heterocyclic group (e.g., pyridyl and the like) and the like are used. Preferable examples of the substituent of the "heterocyclic group optionally having substituent(s)" for $R^1$ include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), aralkyloxycarbonyl (e.g., $C_{7-12}$ aralkyloxy-carbonyl such as benzyloxycarbonyl etc., and the like) and the like.

$R^1$ is, for example, (i) $C_{1-6}$ alkyl optionally having substituent(s), (ii) $C_{3-6}$ cycloalkyl optionally having substituent(s), (iii) $C_{2-6}$ alkenyl optionally having substituent(s), (iv) $C_{6-10}$ aryl optionally having substituent(s), (v) amino optionally having substituent(s) or the like. Particularly, (i) $C_{1-6}$ alkyl (e.g., methyl, ethyl, propyl) optionally having substituent(s), (ii) $C_{3-6}$ cycloalkyl (e.g., cyclopropyl) optionally having substituent(s), (iii) $C_{6-10}$ aryl (e.g., phenyl) optionally having substituent(s), and (iv) amino optionally having substituent (s) are more preferable. These groups optionally have, as substituents, for example, 1 to 5 from the substituents that the aforementioned "hydrocarbon group" optionally has and the like.

As $R^1$, particularly, (i) $C_{1-6}$ alkyl (e.g., methyl, ethyl, propyl), (ii) $C_{3-6}$ cycloalkyl (e.g., cyclopropyl), (iii) $C_{6-10}$ aryl (e.g., phenyl) or (iv) mono-$C_{1-6}$ alkylamino (e.g., ethylamino) is preferable.

In the aforementioned formulas, $R^2$ is a hydrogen atom or a hydrocarbon group optionally having substituent(s).

Preferable examples of the "hydrocarbon group" of the "hydrocarbon group optionally having substituent(s)" for $R^2$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl etc., and the like), aryl (e.g., $C_{6-14}$ aryl such as phenyl etc., and the like) and the like, particularly alkyl (e.g., $C_{1-6}$ alkyl such as methyl etc., and the like), aryl (e.g., $C_{6-14}$ aryl such as phenyl etc., and the like) and the like. The "alkyl", "alkenyl", "alkynyl", "cycloalkyl" and "aryl" optionally have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

As $R^2$, a hydrogen atom or $C_{1-6}$ alkyl optionally having substituent(s) is preferable, more preferably a hydrogen atom or $C_{1-6}$ alkyl, particularly preferably a hydrogen atom.

In the aforementioned formulas, $R^3$ is a hydrogen atom, a halogen atom, a hydrocarbon group optionally having substituent(s), amino optionally having substituent(s), hydroxy optionally having a substituent or mercapto optionally having a substituent.

As the "halogen atom" for $R^3$, fluorine, chlorine or bromine is preferable.

Preferable examples of the "hydrocarbon group" of the "hydrocarbon group optionally having substituent(s)" for $R^3$ include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl etc., and the like), aryl (e.g., $C_{6-14}$ aryl such as phenyl etc., and the like) and the like, particularly alkyl (e.g., $C_{1-6}$ alkyl such as methyl etc., and the like), alkenyl (e.g., $C_{2-6}$ alkenyl such as vinyl etc., and the like) and the like. The "alkyl", "alkenyl", "alkynyl", "cycloalkyl" and "aryl" optionally have, for example, 1 to 5, preferably 1 to 3, from the substituents that the aforementioned "hydrocarbon group" optionally has and the like.

Preferable examples of the substituent of the "amino optionally having substituent(s)" for $R^3$ include 1 or 2 from lower alkyl optionally having substituent(s), aryl optionally having substituent(s) and the like, particularly one from lower alkyl optionally having substituent(s) and the like. Examples of the "lower alkyl" include $C_{1-6}$ alkyl such as methyl, ethyl, propyl, isopropyl, butyl, isobutyl, sec-butyl, tert-butyl and the like, and the like. The "lower alkyl" optionally has, for example, 1 to 3 from the substituents that the aforementioned "hydrocarbon group" optionally has. Examples of the "aryl" include $C_{6-10}$ aryl such as phenyl and the like, and the like. The "aryl" optionally has, for example, 1 to 5, preferably 1 to 3, from the substituents that the aforementioned "hydrocarbon group" optionally has (preferably, a halogen atom such as fluorine, chlorine etc.; $C_{1-6}$ alkoxy such as methoxy, ethoxy etc.; and the like). General examples of the "amino optionally having substituent(s)" include $C_{6-10}$ arylamino (e.g., phenylamino and the like) optionally having 1 to 3 $C_{1-6}$ alkoxy (e.g., methoxy and the like), mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like) and the like.

Preferable examples of the "hydroxy optionally having a substituent" for $R^3$ include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like, particularly, hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" optionally have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

Preferable examples of the "mercapto optionally having a substituent" for $R^3$ include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. Specific examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; and the like), and the like.

$R^3$ is preferably a hydrogen atom or $C_{1-6}$ alkyl optionally having substituent(s), more preferably, a hydrogen atom or $C_{1-6}$ alkyl, particularly preferably, a hydrogen atom.

In the aforementioned formulas, ring A is a 5-membered ring optionally having substituent(s).

As the substituent of the "5-membered ring optionally having substituent(s)", for example, a halogen atom, a hydrocarbon group optionally having substituent(s), amino optionally having substituent(s), hydroxy optionally having a substituent, mercapto optionally having a substituent, a heterocyclic group optionally having substituent(s) and the like can be mentioned. Ring A may have 1 or 2 of the above-mentioned substituents at substitutable position(s).

Preferable examples of the "halogen atom" include fluorine, chlorine and bromine.

Preferable examples of the "hydrocarbon group" of the "hydrocarbon group optionally having substituent(s)" include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. Of these, preferable examples include alkyl (e.g., $C_{1-6}$ alkyl such as methyl etc., and the like), alkenyl (e.g., $C_{2-6}$ alkenyl such as vinyl etc., and the like) and the like. The "alkyl", "alkenyl", "alkynyl", "cycloalkyl" and "aryl" may have, for example, 1 to 5, preferably 1 to 3, substituents that the aforementioned "hydrocarbon group" may have, and the like.

Preferable examples of the "amino optionally having substituent(s)" include amino, $C_{1-6}$ alkylamino optionally having substituent(s), $C_{6-10}$ arylamino optionally having substituent(s) and the like. Of these, examples include amino, mono- or di-$C_{1-6}$ alkylamino (e.g., methylamino, ethylamino, propylamino, isopropylamino, butylamino, tert-butylamino, dimethylamino, diethylamino, N-ethyl-N-methylamino and the like), $C_{6-10}$ arylamino (e.g., phenylamino and the like) and the like.

Preferable examples of the "hydroxy optionally having a substituent" include hydroxy, $C_{1-6}$ alkoxy (e.g., methoxy, ethoxy, propoxy, isopropoxy and the like) optionally having substituent(s), $C_{2-6}$ alkenyloxy (e.g., vinyloxy and the like) optionally having substituent(s), $C_{2-6}$ alkynyloxy (e.g., ethynyloxy and the like) optionally having substituent(s), $C_{3-6}$ cycloalkyloxy (e.g., cyclopropyloxy, cyclobutyloxy, cyclopentyloxy, cyclohexyloxy and the like) optionally having substituent(s), $C_{6-14}$ aryloxy (e.g., phenoxy and the like) optionally having substituent(s) and the like. Of these, preferable examples include hydroxy, $C_{1-6}$ alkoxy (e.g., methoxy and the like) optionally having substituent(s), $C_{6-14}$ aryloxy (e.g., phenoxy and the like) optionally having substituent(s) and the like. The "$C_{1-6}$ alkoxy", "$C_{2-6}$ alkenyloxy", "$C_{2-6}$ alkynyloxy", "$C_{3-6}$ cycloalkyloxy" and "$C_{6-14}$ aryloxy" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; and the like), and the like.

Preferable examples of the "mercapto optionally having a substituent" include mercapto, $C_{1-6}$ alkylthio (e.g., methylthio, ethylthio, propylthio, isopropylthio and the like) optionally having substituent(s), $C_{2-6}$ alkenylthio (e.g., vinylthio and the like) optionally having substituent(s), $C_{2-6}$ alkynylthio (e.g., ethynylthio and the like) optionally having substituent(s), $C_{3-6}$ cycloalkylthio (e.g., cyclopropylthio, cyclobutylthio, cyclopentylthio, cyclohexylthio and the like) optionally having substituent(s), $C_{6-14}$ arylthio (e.g., phenylthio and the like) optionally having substituent(s) and the like. Of these, preferable examples include mercapto, $C_{1-6}$ alkylthio (e.g., methylthio and the like) optionally having substituent(s), $C_{6-14}$ arylthio (e.g., phenylthio and the like) optionally having substituent(s) and the like. The "$C_{1-6}$ alkylthio", "$C_{2-6}$ alkenylthio", "$C_{2-6}$ alkynylthio", "$C_{3-6}$ cycloalkylthio" and "$C_{6-14}$ arylthio" may have, for example, 1 to 5, preferably 1 to 3, from the substituents that the aforementioned "hydrocarbon group" may have (preferably, a halogen atom such as chlorine, fluorine etc.; $C_{1-6}$ alkoxy such as methoxy, ethoxy etc.; and the like), and the like.

Preferable examples of the "heterocyclic group" of the "heterocyclic group optionally having substituent(s)" include a 5- or 6-membered heterocyclic group containing, besides a carbon atom, 1 to 3 hetero atoms selected from a nitrogen atom, an oxygen atom and a sulfur atom and the like. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Specific preferable examples include a 6-membered nitrogen-containing heterocyclic group (e.g., pyridyl and the like) and the like. Preferable examples of the substituent of the "heterocyclic group optionally having substituent(s)" include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), aralkyloxycarbonyl (e.g., $C_{7-12}$ aralkyloxy-carbonyl such as benzyloxycarbonyl etc., and the like), amino, mono-$C_{1-6}$ alkylamino (e.g., methylamino, ethylamino and the like), di-$C_{1-6}$ alkylamino (e.g., dimethylamino, diethylamino and the like) and the like.

Ring A is preferably a 5-membered ring optionally having one substituent selected from $C_{1-6}$ alkyl optionally having substituent(s) and $C_{2-6}$ alkenyl optionally having substituent(s). Particularly, a 5-membered ring optionally having one $C_{1-6}$ alkyl optionally having substituent(s) is preferable. Specifically, a 5-membered ring optionally having one $C_{1-6}$ alkyl is preferable. Moreover, an unsubstituted 5-membered ring is preferable.

In the aforementioned formulas, ring B is a 6-membered ring optionally having substituent(s).

As the substituent of the "6-membered ring optionally having substituent(s)", a halogen atom, a hydrocarbon group optionally having substituent(s), amino optionally having substituent(s), hydroxy optionally having a substituent, mercapto optionally having a substituent, a heterocyclic group optionally having substituent(s) and the like can be mentioned. Ring B optionally has 1 or 2 substituents mentioned above at substitutable position(s). Preferable examples of these substituents include preferable examples of the substituent of ring A and the like.

Ring B is preferably a 6-membered ring optionally having one substituent selected from a halogen atom, hydroxy optionally having a substituent and $C_{1-6}$ alkyl optionally having substituent(s). Particularly, a 6-membered ring optionally having one halogen atom is preferable. Moreover, an unsubstituted 6-membered ring is preferable.

In the aforementioned formulas, ring C is a 5-membered ring optionally having substituent(s).

As the substituent of the "5-membered ring optionally having substituent(s)", for example, a halogen atom, a hydrocarbon group optionally having substituent(s), hydroxy optionally having a substituent, a heterocyclic group optionally having substituent(s) and the like can be mentioned. Ring C optionally has 1 or 2 substituents mentioned above at substitutable position(s).

Preferable examples of the "halogen atom" include fluorine, chlorine and bromine.

Preferable examples of the "hydrocarbon group" of the "hydrocarbon group optionally having substituent(s)" include alkyl (e.g., $C_{1-6}$ alkyl such as methyl, ethyl, propyl, isopropyl etc., and the like), alkenyl (e.g., $C_{2-6}$ alkenyl such as vinyl etc., and the like), alkynyl (e.g., $C_{2-6}$ alkynyl such as ethynyl etc., and the like), cycloalkyl (e.g., $C_{3-6}$ cycloalkyl such as cyclopropyl, cyclobutyl, cyclopentyl, cyclohexyl, and the like), aryl (e.g., $C_{6-14}$ aryl such as phenyl etc., and the like) and the like. More preferable examples include alkyl (e.g., $C_{1-6}$ alkyl such as methyl etc., and the like), aryl (e.g., $C_{6-14}$ aryl such as phenyl etc., and the like) and the like. The "alkyl", "alkenyl", "alkynyl", "cycloalkyl" and "aryl" may have, for example, 1 to 5, preferably 1 to 3, from the substituents that the aforementioned "hydrocarbon group" optionally has (preferably, a halogen atom such as chlorine, fluorine etc.; $C_{1-6}$ alkoxy such as methoxy, ethoxy etc.; and the like) and the like.

As a preferable example of the "heterocyclic group" of the "heterocyclic group optionally having substituent(s)", for example, a 5- or 6-membered heterocyclic group containing, besides a carbon atom, 1 to 3 hetero atoms selected from a nitrogen atom, an oxygen atom and a sulfur atom and the like can be mentioned. Specifically, for example, 1-, 2- or 3-pyrrolidinyl, 2- or 4-imidazolinyl, 2-, 3- or 4-pyrazolidinyl, piperidino, 2-, 3- or 4-piperidyl, 1- or 2-piperazinyl, morpholinyl, 2- or 3-thienyl, 2-, 3- or 4-pyridyl, 2- or 3-furyl, pyrazinyl, 2-pyrimidinyl, 3-pyrrolyl, 3-pyridazinyl, 3-isothiazolyl, 3-isoxazolyl and the like can be mentioned. Particularly preferably, a 6-membered nitrogen-containing heterocyclic group (e.g., pyridyl and the like) and the like can be mentioned. Preferable examples of the substituent of the "heterocyclic group optionally having substituent(s)" include a halogen atom (e.g., chlorine, fluorine and the like), $C_{1-6}$ alkyl (e.g., methyl, ethyl and the like), $C_{1-6}$ alkoxy (e.g., methoxy, ethoxy and the like), aralkyloxycarbonyl (e.g., $C_{7-12}$ aralkyloxy-carbonyl such as benzyloxycarbonyl etc., and the like), amino, mono-$C_{1-6}$ alkylamino (e.g., methylamino, ethylamino and the like), di-$C_{1-6}$ alkylamino (e.g., dimethylamino, diethylamino and the like) and the like.

Ring C is preferably a 5-membered ring optionally having 1 or 2 substituents selected from $C_{1-6}$ alkyl optionally having substituent(s), $C_{3-6}$ cycloalkyl optionally having substituent(s), $C_{6-10}$ aryl optionally having substituent(s), hydroxy optionally having a substituent and a 5- or 6-membered heterocyclic group optionally having substituent(s). Examples of the substituent include 1 or 2 substituents selected from a halogen atom, $C_{1-6}$ alkyl, $C_{1-6}$ alkoxy, amino, mono-$C_{1-6}$ alkylamino, di-$C_{1-6}$ alkylamino and the like. Ring C is more preferably a 5-membered ring optionally having one substituent selected from optionally halogenated $C_{1-6}$ alkyl, optionally halogenated $C_{3-6}$ cycloalkyl and optionally halogenated $C_{6-10}$ aryl (preferably phenyl), more preferably, a 5-membered ring optionally having one substituent selected from (1) $C_{1-6}$ alkyl optionally having 1 to 3 halogen atoms, (2) $C_{3-6}$ cycloalkyl and (3) $C_{6-10}$ aryl optionally having 1 to 3 halogen atoms, particularly preferably, a 5-membered ring optionally having one substituent selected from (1) $C_{1-6}$ alkyl optionally substituted by fluorine atom (e.g., methyl, trifluoromethyl, ethyl, isopropyl), (2) $C_{3-6}$ cycloalkyl (e.g., cyclopropyl), and (3) $C_{6-10}$ aryl optionally substituted by fluorine atom (e.g., phenyl, 4-fluorophenyl).

Examples of the tricycle consisting of ring A, ring B and ring C include rings represented by the formulas

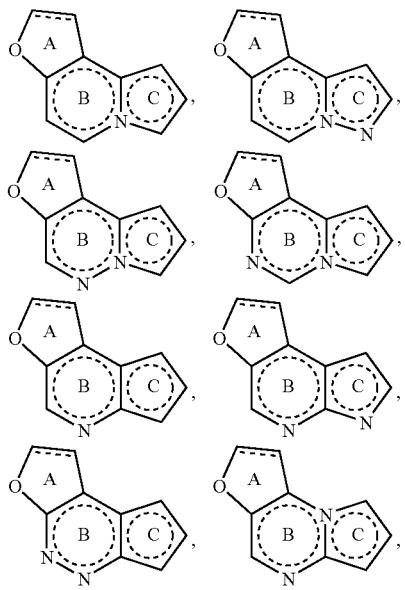

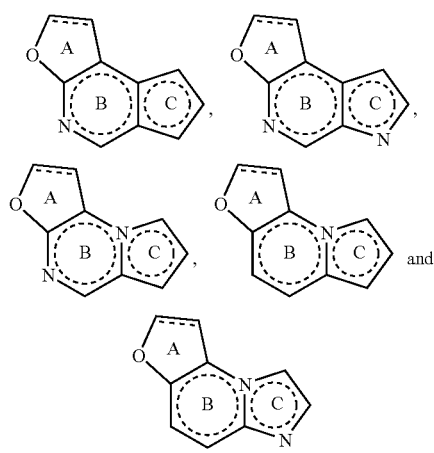

wherein each symbol is as defined above, and the like.

Preferable examples include rings represented by the formulas

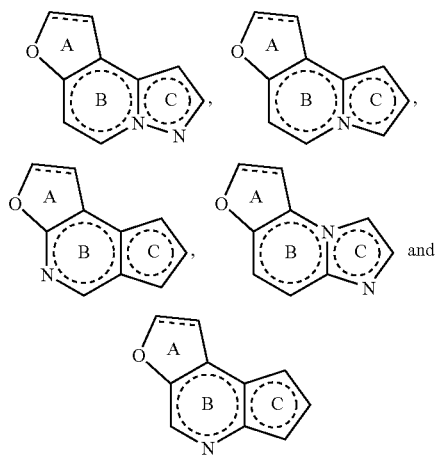

wherein each symbol is as defined above, and the like.

More preferable examples include rings represented by the formulas

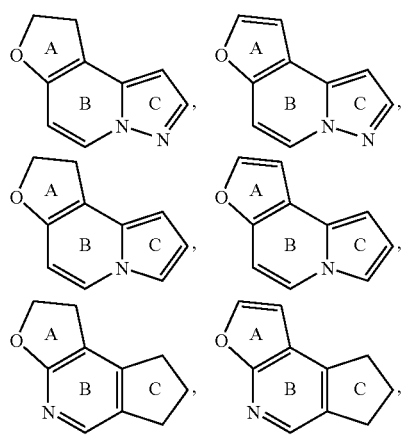

wherein each symbol is as defined above, and the like. Particularly preferably, in the above-mentioned formulas, ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent; ring B is a 6-membered ring optionally having 1 or 2 substituents selected from a halogen atom, a hydrocarbon group optionally having substituent(s), amino optionally having substituent(s), hydroxy optionally having a substituent and mercapto optionally having a substituent; and ring C is a 5-membered ring optionally having 1 or 2 substituents selected from a halogen atom, a hydrocarbon group optionally having substituent(s), hydroxy optionally having a substituent and a heterocyclic group optionally having substituent(s) and the like.

In the above-mentioned formulas, m is 0, 1 or 2, preferably 1.

As compound (I), a compound wherein
$R^1$ is $C_{1-6}$ alkyl optionally having substituent(s), $C_{3-6}$ cycloalkyl optionally having substituent(s), $C_{2-6}$ alkenyl optionally having substituent(s), $C_{6-10}$ aryl optionally having substituent(s) or amino optionally having substituent(s);
$R^2$ is a hydrogen atom or $C_{1-6}$ alkyl optionally having substituent(s);
$R^3$ is a hydrogen atom or $C_{1-6}$ alkyl optionally having substituent(s);
m is 1;
ring A is a 5-membered ring optionally having 1 or 2 substituents selected from a halogen atom, a hydrocarbon group optionally having substituent(s), amino optionally having substituent(s), hydroxy optionally having a substituent and mercapto optionally having a substituent;
ring B is a 6-membered ring optionally having 1 or 2 substituents selected from a halogen atom, a hydrocarbon group optionally having substituent(s), amino optionally having substituent(s), hydroxy optionally having a substituent and mercapto optionally having a substituent; and
ring C is a 5-membered ring optionally having 1 or 2 substituents selected from a halogen atom, a hydrocarbon group optionally having substituent(s), hydroxy optionally having a substituent and a heterocyclic group optionally having substituent(s) and the like are preferable, and particularly, a compound wherein
$R^1$ is $C_{1-6}$ alkyl, $C_{3-6}$ cycloalkyl, $C_{6-10}$ aryl or mono-$C_{1-6}$ alkylamino;
$R^2$ is a hydrogen atom;
$R^3$ is a hydrogen atom or $C_{1-6}$ alkyl;
m is 1;
ring A is a 5-membered ring optionally having one $C_{1-6}$ alkyl;
ring B is an unsubstituted 6-membered ring;
ring C is a 5-membered ring optionally having one substituent selected from (1) $C_{1-6}$ alkyl optionally having 1 to 3 halogen atoms, (2) $C_{3-6}$ cycloalkyl and (3) $C_{6-10}$ aryl optionally having 1 to 3 halogen atoms;
Xa is CH, $CH_2$ or N;
Xb is C or N;
Xc is CH or N;
Xd is CH or N; and
Xe is C or N, and the like are preferable.

Preferable examples of compound (I) include compounds represented by the formulas

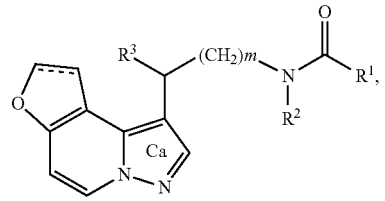

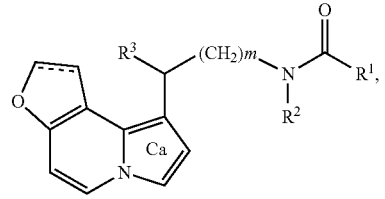

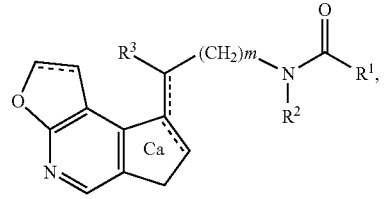

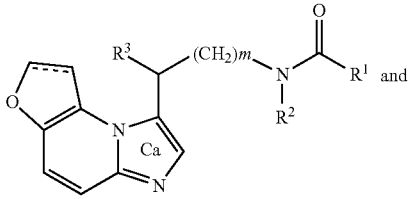 and

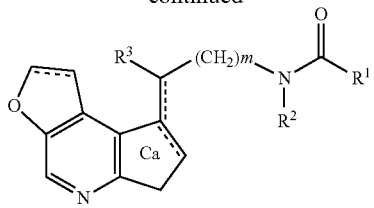

wherein ring Ca is as defined for the above-mentioned ring C, and other symbols are as defined above, and the like.

Particularly, a compound wherein $R^1$ is $C_{1-6}$ alkyl, $C_{3-6}$ cycloalkyl, $C_{6-10}$ aryl or $C_{1-6}$ alkylamino; $R^2$ is a hydrogen atom; $R^3$ is a hydrogen atom; m is 1; and ring Ca is a 5-membered ring having optionally halogenated $C_{1-6}$ alkyl, $C_{3-6}$ cycloalkyl or optionally halogenated phenyl, and the like can be mentioned.

As compound (I), the compounds described in Examples 1 to 39 are specifically preferable. Particularly, N-[2-(8,9-dihydrofuro[3,2-c]pyrazolo[1,5-a]pyridin-1-yl)ethyl]acetamide, N-[2-(2-ethyl-8,9-dihydrofuro[3,2-c]pyrazolo[1,5-a]pyridin-1-yl)ethyl]acetamide, N-[2-(2-ethyl-8,9-dihydrofuro[3,2-c]pyrazolo[1,5-a]pyridin-1-yl)ethyl]propanamide, N-[2-(2-methyl-8,9-dihydrofuro[3,2-c]pyrazolo[1,5-a]pyridin-1-yl)ethyl]acetamide, N-{2-[2-(trifluoromethyl)-8,9-dihydrofuro[3,2-c]pyrazolo[1,5-a]pyridin-1-yl]ethyl}acetamide, N-[2-(1,6,7,8-tetrahydro-2H-cyclopenta[d]furo[2,3-b]pyridin-8-yl)ethyl]acetamide, N-[2-(1,6,7,8-tetrahydro-2H-cyclopenta[d]furo[2,3-b]pyridin-8-yl)ethyl]propanamide, N-[2-(7-phenyl-1,2-dihydrofuro[2,3-e]imidazo[1,2-a]pyridin-8-yl)ethyl]acetamide, N-[2-(2-phenyl-8,9-dihydrofuro[3,2-c]pyrazolo[1,5-a]pyridin-1-yl)ethyl]acetamide, N-[2-(2-ethyl-8,9-dihydrofuro[3,2-c]pyrazolo[1,5-a]pyridin-1-yl)propyl]acetamide, and salts thereof are preferable.

As a salt of compound (I), for example, a pharmacologically acceptable salt and the like are used. For example, a salt with inorganic base, a salt with organic base, a salt with inorganic acid, a salt with organic acid, a salt with basic or acidic amino acid and the like can be mentioned. Preferable examples of salts with inorganic base include alkali metal salt such as sodium salt, potassium salt and the like, alkaline earth metal salt such as calcium salt, magnesium salt and the like, and aluminum salt, ammonium salt and the like. Preferable examples of salts with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acid include salts with hydrochloric acid, hydrobromic acid, nitric acid, sulfuric acid, phosphoric acid and the like. Preferable examples of salts with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acid include salts with arginine, lysine, ornithine and the like, and preferable examples of salts with acidic amino acid include salts with aspartic acid, glutamic acid and the like. Of these, a pharmaceutically acceptable salt is preferable. Examples thereof when compound (I) has a basic functional group include salts with inorganic acid such as hydrochloric acid, hydrobromic acid, nitric acid, sulfuric acid, phosphoric acid and the like, and salts with organic acid such as acetic acid, phthalic acid, fumaric acid, tartaric acid, maleic acid, citric acid, succinic acid, methanesulfonic acid, p-toluenesulfonic acid and the like. Examples thereof when compound (I) has an acidic functional group include alkali metal salts such as sodium salt, potassium salt and the like, alkaline earth metal salts such as calcium salt, magnesium salt and the like, ammonium salt and the like.

The production methods of compound (I) are described in the following. The production methods of compound (I') are analogous to those of compound (I).

The following compounds (II)-(LII) include salts thereof. As the salt, for example, one similar to the salt of compound (I) and the like are used.

The compound obtained in each step can be directly used as a reaction mixture or a crude product for the next reaction. It can be isolated from a reaction mixture according to a conventional method, and can be easily purified by a separation means such as recrystallization, distillation, chromatography and the like.

The reaction schemes thereof are shown below, wherein each symbol of the compound is as defined above. In the formulas, $R^{4a-4k}$ are each a hydrogen atom, a hydrocarbon group optionally having substituent(s) or a heterocyclic group optionally having substituent(s), $R^{5a-5o}$ are each a hydrogen atom or a hydrocarbon group optionally having substituent(s), Y is a halogen atom, and Xf and Xg are each a carbon atom or a nitrogen atom.

From among those recited as examples of the solvents used for the production methods of compound (I), the following solvents are specifically used.
Alcohols:
methanol, ethanol, 1-propanol, 2-propanol, tert-butyl alcohol and the like
Ethers:
diethyl ether, diisopropyl ether, diphenyl ether, tetrahydrofuran, 1,4-dioxane, 1,2-dimethoxyethane and the like
Aromatic Hydrocarbons:
benzene, chlorobenzene, toluene, xylene and the like
Saturated Hydrocarbons:
cyclohexane, hexane and the like
Amides:
N,N-dimethylformamide, N,N-dimethylacetamide, hexamethylphosphoric triamide and the like
Halogenated Hydrocarbons:
dichloromethane, chloroform, carbon tetrachloride, 1,2-dichloroethane and the like
Nitriles:
acetonitrile, propionitrile and the like
Sulfoxides:
dimethyl sulfoxide and the like
Aromatic Organic Bases:
pyridine, lutidine and the like
Acid Anhydrides:
acetic anhydride and the like
Organic Acids:
formic acid, acetic acid, propionic acid, trifluoroacetic acid, methanesulfonic acid and the like
Inorganic Acids:
sulfuric acid and the like
Esters:
methyl acetate, ethyl acetate, butyl acetate and the like
Ketones:
acetone, methyl ethyl ketone and the like From among those recited as examples of the base and deacidifying agent used for the production methods of compound (I), the following bases are specifically used.
Inorganic Bases:

sodium hydroxide, potassium hydroxide, magnesium hydroxide and the like
Basic Salts:
sodium carbonate, potassium carbonate, cesium carbonate, calcium carbonate, sodium hydrogen carbonate and the like
Organic Bases:
triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like
Metal Alkoxides:
sodium methoxide, sodium ethoxide, potassium tert-butoxide and the like
Alkali Metal Hydrides:
sodium hydride, potassium hydride and the like
Metal Amides:
sodium amide, lithium diisopropylamide, lithium hexamethyldisilazide and the like
Organic Lithiums:
methyllithium, n-butyllithium, sec-butyllithium, tert-butyllithium and the like From among those recited as examples of the acid catalysts used for the production methods of compound (I), the following acid catalysts are specifically used.
Inorganic Acids:
hydrochloric acid, sulfuric acid, nitric acid, hydrobromic acid, phosphoric acid and the like
Organic Acids:
acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid and the like
Lewis Acid:
boron trifluoride ether complex, zinc iodide, anhydrous aluminum chloride, anhydrous zinc chloride, anhydrous iron chloride and the like From among those recited as examples of the halogenating agents used for the production methods of compound (I), the following halogenating agents are specifically used.
Phosphorus Halide:
phosphorus trichloride, phosphorus oxychloride, phosphorus pentachloride, phosphorus tribromide, phosphorus triiodide and the like Succinimides:
bromosuccinimide, iodosuccinimide and the like
Halogen:
chlorine, bromine, iodine, iodine fluoride, iodine chloride and the like From among those recited as examples of the metal catalysts used for the production methods of compound (I), the following metal catalysts are specifically used.
Palladium Compound:
palladium(II) acetate, tetrakis(triphenylphosphine)palladium(0), bis(triphenylphosphine)palladium(II) chloride, dichlorobis(triethylphosphine)palladium(II), tris(dibenzylideneacetone)dipalladium(0), [2,2'-bis(diphenylphosphino)-1,1'-binaphthyl]palladium(II) chloride, complex of palladium(II) acetate and 1,1'-bis(diphenylphosphino)ferrocene, and the like
Nickel Compound:
tetrakis(triphenylphosphine)nickel(0), bis(triethylphosphine)nickel(II) chloride, bis(triphenylphosphine)nickel(II) chloride and the like
Rhodium Compound:
tris(triphenylphosphine)rhodium(III) chloride and the like
copper compound:
copper oxide, copper(II) chloride and the like From among those recited as examples of the reducing agents used for the production methods of compound (I), the following reducing agents are specifically used.
Metal Hydride:
aluminum hydride, diisobutylaluminum hydride, tributyltin hydride and the like
Metal Hydride Complex Compound:
sodium cyanoborohydride, sodium triacetoxyborohydride, sodium borohydride, lithium aluminum hydride and the like
Borane Complex:
borane tetrahydrofuran complex, borane dimethyl sulfide complex and the like
Alkylboranes:
thexylborane, disiamylborane and the like
Metals:
zinc, aluminum, tin, iron and the like

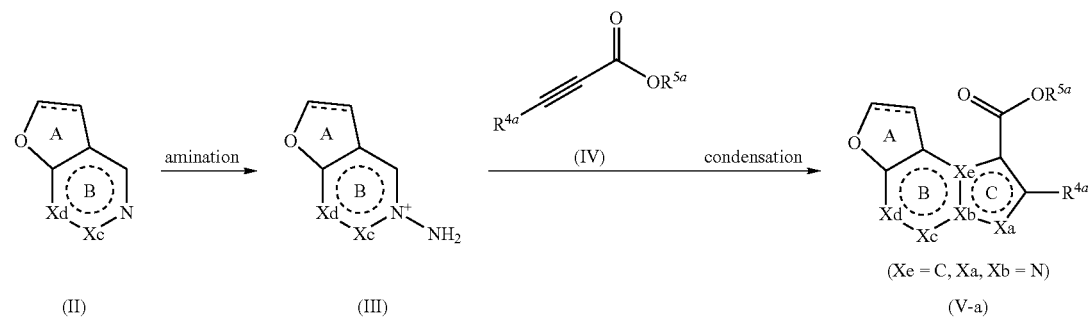

(Reaction 01)

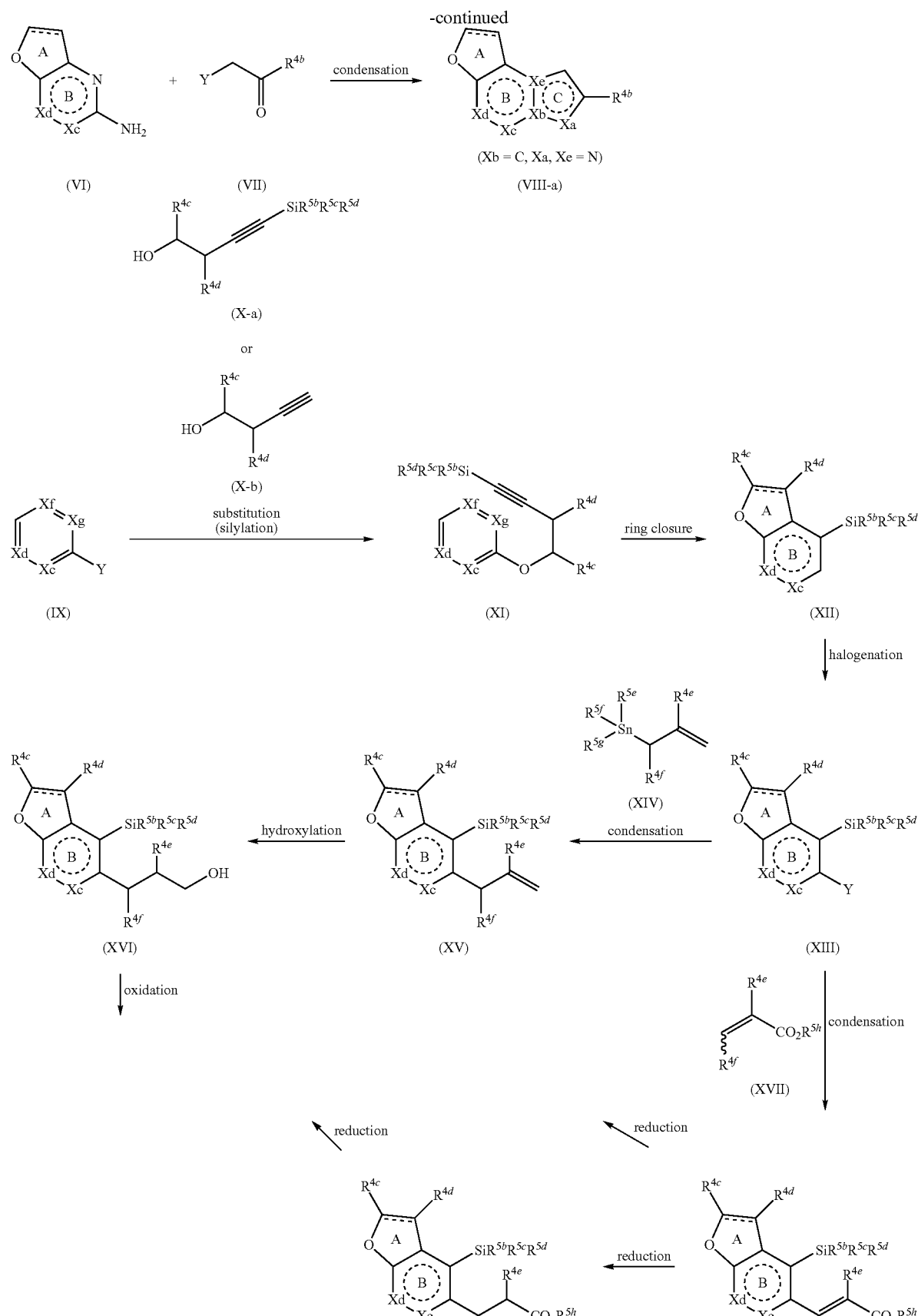

Compound (II) can be produced according to a method known per se, for example, the method described in Heterocycles, vol. 45, page 976 (1997), J. Heterocyclic Chem., vol. 8, page 57 (1971), J. Heterocyclic Chem., vol. 34, page 941 (1997) and the like, or a method analogous thereto.

Compound (VI) can be produced according to a method known per se, for example, the method described in Chem. Pharm. Bull., vol. 32, page 4914 (1984), Heterocycles, vol. 45, page 976 (1997) and the like, or a method analogous thereto.

Compound (IX) can be produced according to a method known per se, for example, the method described in Tetrahedron, vol. 45, page 803 (1989), Tetrahedron, vol. 44, page 2977 (1988), Tetrahedron, vol. 43, page 5145 (1987) and the like, or a method analogous thereto according to.

Compound (XXIII) can be produced according to a method known per se, for example, the method described in Synth. Commun., vol. 20, page 1819 (1990) and the like, or a method analogous thereto.

Compound (XXIV) can be produced according to a method known per se, for example, the method described in Tetrahedron Lett., vol. 41, page 4165 (2000) and the like, or a method analogous thereto.

Compound (XLIII) can be produced according to a method known per se, for example, the method described in Heterocycles, vol. 45, page 976 (1997), WO2004/100947, J. Heterocyclic Chem., vol. 8, page 57 (1971) and the like, or a method analogous thereto.

Compounds (IV), (VII), (X-a), (X-b), (XIV), (XVII), (XXIX), (XLIV) and (XLVI) can be produced according to a method known per se, or a method analogous thereto.

When the compounds used in the explanation of the present production methods are commercially available, such commercially available products can also be used directly.

Compound (III) can be produced by reacting compound (II) with an amination reagent. Examples of the amination reagent include o-mesitylenesulfonylhydroxylamine, o-(2,4-dinitrophenyl)hydroxylamine, and a mixture thereof. These reagents can be produced according to a method described in, for example, J. Org. Chem., vol. 38, page 1239 (1973), J. Org. Chem., vol. 68, page 7119 (2003) and the like, or a method analogous thereto. The amination reagent is used in an amount of about 1.0 to 20 mol, preferably about 1.0 to 3.0 mol, per 1 mol of compound (II). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min to 170 hr, preferably 1 hr to 80 hr. The reaction temperature is generally 0° C. to 150° C., preferably 20° C. to 80° C.

Compound (V-a) wherein Xe is a carbon atom and Xa and Xb are nitrogen atoms can be produced by a condensation reaction of compound (III) and compound (IV) in the presence of a base. Examples of the base include inorganic bases, basic salts, organic bases, metal alkoxides and the like. The base is used in an amount of about 1.0 to 20 mol, preferably about 1.0 to 5.0 mol, per 1 mol of compound (III). Compound (IV) is used in an amount of about 1.0 to 20 mol, preferably about 1.0 to 5.0 mol, per 1 mol of compound (III). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min to 50 hr, preferably 1 hr to 25 hr. The reaction temperature is generally −20° C. to 150° C., preferably 0° C. to 80° C.

Compound (VIII-a) wherein Xb is a carbon atom and Xa and Xe are nitrogen atoms can be produced by a condensation reaction of compound (VI) and compound (VII). Compound (VII) is used in an amount of about 0.5 to 20 mol, preferably about 0.8 to 5.0 mol, per 1 mol of compound (VI). To promote the reaction, the reaction can be performed in the presence of a base. Examples of the base include inorganic bases, basic salts, organic bases, metal alkoxides and the like. The base is used in an amount of about 0.1 to 30 mol, preferably about 1.0 to 10 mol, per 1 mol of compound (VI). This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, aromatic organic bases and the like or a mixed solvent thereof and the like are preferable. While the reaction time varies depending on the reagent and solvent to be used, it is generally 5 min to 100 hr, preferably 30 min to 24 hr. The reaction temperature is generally −20° C. to 200° C., preferably 0° C. to 150° C.

Compound (XI) can be produced by subjecting compound (IX) to a substitution reaction with compound (X-a). Compound (X-a) is used in an amount of about 1.0 to 10 mol, preferably about 1.0 to 5 mol, per 1 mol of compound (IX). To promote the reaction, the reaction can also be performed in the presence of a base. Examples of the base include inorganic bases, basic salts, organic bases, metal alkoxides, alkali metal hydrides, metal amides, organic lithiums and the like. The base is used in an amount of about 1.0 to 10 mol, preferably about 1.0 to 5.0 mol, per 1 mol of compound (IX). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 10 min to 100 hr, preferably 30 min to 24 hr. The reaction temperature is generally −78° C. to 150° C., preferably −20° C. to 100° C.

Compound (XI) can also be produced by subjecting compound (IX) to a substitution reaction with compound (X-b), and then a reaction with a silylating agent in the presence of a base. The substitution reaction of compound (IX) with compound (X-b) can be performed in the same manner as in the substitution reaction of compound (IX) with compound (X-a). Examples of the silylating agent include trimethylsilyl chloride, triethylsilyl chloride, triisopropylsilyl chloride, tert-butyldimethylsilyl chloride, tert-butyldiphenylsilyl chloride and the like. The silylating agent is used in an amount of about 1.0 to 5.0 mol, preferably about 1.0 to 2.0 mol, per 1 mol of compound (IX). Examples of the base include inorganic bases, basic salts, organic bases, metal alkoxides, alkali metal hydrides, metal amides, organic lithiums and the like. The base is used in an amount of about 1.0 to 5.0 mol, preferably about 1.0 to 2.5 mol, per 1 mol of compound (IX). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides and the like or a mixed solvent thereof and the like are preferable. While the reaction time varies depending on the reagent and solvent to be used, it is generally 30 min to 48 hr, preferably 30 min to 5 hr. The reaction temperature is generally −78° C. to 200° C., preferably −78° C. to 150° C.

Compound (XII) can be produced by subjecting compound (XI) to a ring closure reaction. The ring closure reaction is performed by a heat treatment. To promote the reaction, the reaction can also be performed using an acidic catalyst. Examples of the acidic catalyst include inorganic acids, organic acids, Lewis acid and the like. The acidic catalyst is used in an amount of about 0.01 to 100 mol, preferably about 0.01 to 5.0 mol, per 1 mol of compound (XI). This reaction is advantageously performed without solvent or in a solvent inert to the reaction. While the solvent is not particularly limited as long as the reaction proceeds, for example, solvents such as ethers, aromatic hydrocarbons, saturated hydrocarbons, amides, halogenated hydrocarbons, organic acids and the like or a mixed solvent thereof and the like are preferable. While the reaction time varies depending on the reagent and solvent to be used, it is generally 30 min to 200 hr, preferably 1 hr to 50 hr. The reaction temperature is generally 0° C. to 300° C., preferably 50° C. to 250° C.

Compound (XIII) can be produced by reacting compound (XII) with a halogenating agent. Examples of the halogenating agent include phosphorus halide, succinimides, halogen, thionyl chloride, and mixtures thereof and the like. The halogenating agent is used in an amount of about 1.0 to 100 mol, preferably about 1.0 to 10 mol, per 1 mol of compound (XII). To promote the reaction, the reaction can be performed in the presence of a base. Examples of the base include inorganic bases, basic salts and the like. This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, acid anhydrides, organic acids, inorganic acids, water and the like or a mixed solvent thereof and the like are preferable. While the reaction time varies depending on the reagent and solvent to be used, it is generally 10 min to 50 hr, preferably 30 min to 12 hr. The reaction temperature is generally 0° C. to 200° C., preferably 10° C. to 100° C.

Compound (XV) can be produced by condensing compound (XIII) and compound (XIV) in the presence of a metal catalyst. As the metal catalyst, various metal complexes having ligand are used and, for example, palladium compound, nickel compound, rhodium compound, cobalt compound, copper compound, platinum compound and the like can be mentioned. Among these, palladium compound, nickel compound and copper compound are preferable. Compound (XIV) is used in an amount of about 0.8 to 10 mol, preferably about 1.0 to 3.0 mol, per 1 mol of compound (XIII). The metal catalyst is used in an amount of about 0.000001 to 5 mol, preferably about 0.0001 to 1 mol, per 1 mol of compound (XIII). When a metal catalyst unstable to oxygen is used for this reaction, the reaction is preferably performed, for example, in an inert gas stream such as argon gas, nitrogen gas and the like. This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, esters, water and the like or a mixed solvent thereof and the like are preferable. While the reaction time varies depending on the reagent and solvent to be used, it is generally 10 min to 100 hr, preferably 30 min to 50 hr. The reaction temperature is −10° C. to 250° C., preferably 0° C. to 150° C.

Compound (XVI) can be produced by adding a water molecule to compound (XV) in the presence of an acid catalyst. Examples of the acid catalyst include inorganic acids, organic acids, boron trifluoride ether complex and the like can be mentioned. This reaction is advantageously performed using a solvent inert to the reaction. While the solvent is not particularly limited as long as the reaction proceeds, for example, solvents such as alcohols, amides, sulfoxides, organic acids, inorganic acids, water and the like or a mixed solvent thereof and the like are preferable. While the reaction time varies depending on the reagent and solvent to be used, it is generally 10 min to 150 hr, preferably 30 min to 100 hr. The reaction temperature is 0° C. to 200° C., preferably 0° C. to 150° C.

Compound (XVI) can also be produced by hydroboration of compound (XV), and subsequent oxidation reaction. Examples of the hydroboration reagent include borane tetrahydrofuran complex, dicyclohexylborane, 9-borabicyclo[3.3.1]nonane and the like. The hydroboration reagent is used in an amount of about 0.8 to 20.0 mol, preferably about 1.0 to 5.0 mol, per 1 mol of compound (XV). To promote the reaction, the hydroboration reaction can also be performed in the presence of an acid. Examples of the acid include inorganic acids, organic acids, boron trifluoride ether complex and the like. The acid is used in an amount of about 0.01 to 100 mol, preferably about 0.01 to 5.0 mol, per 1 mol of compound (XV). This reaction is preferably performed, for example, in an inert gas stream such as argon gas, nitrogen gas and the like. This reaction is advantageously performed using a solvent inert to the reaction. While the solvent is not particularly limited as long as the reaction proceeds, for example, solvents such as ethers, saturated hydrocarbons, halogenated hydrocarbons and the like and a mixed solvent thereof and the like are preferable. While the reaction time varies depending on the reagent and solvent to be used, it is generally 10 min to 48 hr, preferably 30 min to 10 hr. The reaction temperature is −78° C. to 150° C., preferably −78° C. to 50° C.

Examples of the oxidizing agent in the subsequent oxidation reaction include organic peracids such as perbenzoic acid, m-chloroperbenzoic acid, peracetic acid and the like, oxygen, hydrogen peroxide and the like. The oxidizing agent is used in an amount of about 0.8 to 100 mol, preferably about 1.0 to 10 mol, per 1 mol of compound (XV). The oxidation reaction is preferably performed in the presence of a base. Examples of the base include inorganic bases, basic salts, metal alkoxides and the like. The base is used in an amount of about 1.0 to 100 mol, preferably about 1.0 to 20 mol, per 1 mol of compound (XV). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, aromatic organic bases, water and the like and a mixed solvent thereof and the like are preferable. While the reaction time varies depending on the reagent and solvent to be used, it is generally 10 min to 100 hr, preferably 30 min to 50 hr. The reaction temperature is −20° C. to 150° C., preferably 0° C. to 100° C.

In addition, compound (XVI) can also be produced by hydroxylating compound (XV) according to a method known per se, for example, the method described in 4th Ed. Jikken Kagaku Koza (Courses in Experimental Chemistry), vol. 20, pages 69-110 (The Chemical Society of Japan Ed.) and the like, or a method analogous thereto.

Compound (XVIII) can be produced by condensing compound (XIII) and compound (XVII) in the presence of a metal catalyst. As the metal catalyst, various metal complexes having ligand are used and, for example, palladium compound, nickel compound, cobalt compound, copper compound, platinum compound and the like can be mentioned. Among these, palladium compound, nickel compound and copper compound are preferable. The compound (XVII) is used in an amount of about 0.8 to 10 mol, preferably about 1.0 to 3.0 mol, per 1 mol of compound (XIII). The metal catalyst is used in an amount of about 0.000001 to 5 mol, preferably about 0.0001 to 1 mol, per 1 mol of compound (XIII). This reaction is preferably performed in the presence of a base. Examples of the base include inorganic bases, basic salts, organic bases, metal alkoxides, alkali metal hydrides, metal amides and the like. The base is used in an amount of about 1.0 to 20 mol, preferably about 1.0 to 5.0 mol, per 1 mol of compound (XIII). When a metal catalyst unstable to oxygen is used for this reaction, the reaction is preferably performed, for example, in an inert gas stream such as argon gas, nitrogen gas and the like. This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, esters, water and the like or a mixed solvent thereof and the like are preferable. While the reaction time varies depending on the reagent and solvent to be used, it is generally 10 min to 100 hr, preferably 30 min to 50 hr. The reaction temperature is $-10°$ C. to $250°$ C., preferably $0°$ C. to $150°$ C.

Compound (XVI) can also be produced by subjecting compound (XVIII) to a reduction reaction. Alternatively, compound (XVIII) is subjected to a reduction reaction to give compound (XIX), which is subjected to a different reduction reaction to give compound (XVI). The reduction reaction is performed according to a conventional method and generally using a reducing agent. Examples of the reducing agent include metal hydride, metal hydride complex compound, borane complex, alkylboranes, diborane, metals, alkali metal (e.g., sodium, lithium and the like)/liquid ammonia (Birch reduction) and the like. The amount of the reducing agent to be used is appropriately determined according to the kind of the reducing agent. For example, metal hydride, metal hydride complex compound, borane complex, alkylboranes or diborane is used in an amount of about 0.25 to 10 mol, preferably about 0.5 to 5 mol, per 1 mol of compound (XVIII) or compound (XIX), and metal (including alkali metal to be used for Birch reduction) is used in an amount of about 1.0 to 20 mol, preferably about 1.0 to 5.0 mol, per 1 mol of compound (XVIII) or compound (XIX). This reaction is advantageously performed using a solvent inert to the reaction. While the solvent is not particularly limited as long as the reaction proceeds, for example, solvent such as alcohols, ethers, aromatic hydrocarbons, saturated hydrocarbons, amides, halogenated hydrocarbons, organic acids, water and the like or a mixed solvent thereof and the like are preferable. While the reaction time varies depending on the reagent and solvent to be used, generally 10 min to 100 hr, preferably 30 min to 50 hr. The reaction temperature is $-20°$ C. to $100°$ C., preferably $0°$ C. to $80°$ C.

In addition, the reduction reaction can also be performed by a hydrogenation reaction. In this case, for example, a catalyst such as palladium carbon, platinum(IV) oxide, Raney nickel, Raney cobalt etc., or the like is used. The catalyst is used in an amount of about 1.0 to 300 wt %, preferably about 10 to 20 wt %, relative to compound (XVIII) or compound (XIX). Various hydrogen sources can also be used instead of gaseous hydrogen. As the hydrogen source, for example, formic acid, ammonium formate, triethylammonium formate, sodium phosphinate, hydrazine and the like are used. The hydrogen source is used in an amount of about 1.0 to 10 mol, preferably about 1.0 to 5.0 mol, per 1 mol of compound (XVIII) or compound (XIX). This reaction is advantageously performed using a solvent inert to the reaction. For example, solvents such as alcohols, ethers, aromatic hydrocarbons, saturated hydrocarbons, amides, halogenated hydrocarbons, esters, organic acids, water and the like or a mixed solvent thereof and the like are preferable. While the reaction time varies depending on the kind and amount of the reducing agent or the activity and amount of the catalyst to be used, it is generally 30 min to 100 hr, preferably 1 hr to 50 hr. The reaction temperature is generally $-20°$ C. to $120°$ C., preferably $0°$ C. to $80°$ C. When a hydrogenation catalyst is used, the pressure of hydrogen is generally 1 to 100 atm.

Compound (XX) can be produced by subjecting compound (XVI) to oxidation reaction. The oxidation reaction can be performed according to a method known per se, for example, the method described in 4th Ed. Jikken Kagaku Koza (Courses in Experimental Chemistry), vol. 23, pages 1-550 (The Chemical Society of Japan Ed.) and the like, or a method analogous thereto. For example, oxidation reaction using an oxidizing agent, Swern oxidation reaction using oxalyl chloride and dimethyl sulfoxide, Jones oxidation reaction using pyridine and chromic acid, oxidation reaction using tetra-n-propylammonium perruthenate(VII) and N-methylmorpholine N-oxide and the like can be mentioned. Examples of the oxidizing agent include organic peracids such as perbenzoic acid, m-chloroperbenzoic acid (MCPBA), peracetic acid and the like, perchlorates such as lithium perchlorate, silver perchlorate, tetrabutylammonium perchlorate and the like, periodic acids such as sodium periodate, Dess-Martin periodinane, o-iodoxybenzoic acid (IBX) and the like, manganic acids such as manganese dioxide, potassium permanganate and the like, leads such as lead tetraacetate and the like, chromate such as pyridinium chlorochromate, pyridinium dichromate and the like, inorganic nitrogen compounds such as acyl nitrate, dinitrogen tetroxide and the like, halogen compounds such as halogen, N-bromosuccinimide (NBS), N-chlorosuccinimide (NCS) and the like, sulfuryl chloride, chloramine T, oxygen, hydrogen peroxide and the like can be mentioned. The oxidizing agent is used in an amount of about 0.8 to 20 mol, preferably about 1.0 to 5.0 mol, per 1 mol of compound (XVI). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons, nitrites, sulfoxides, esters, water and the like or a mixed solvent thereof and the like are preferable. While the reaction time varies depending on the reagent and solvent to be used, generally 10 min to 100 hr, preferably 30 min to 50 hr. The reaction temperature is $-78°$ C. to $150°$ C., preferably $-78°$ C. to $100°$ C.

Compound (XXI) can be produced by subjecting compound (XX) to a ring closure reaction. The ring closure reaction is generally performed in the presence of a fluoride. Examples of the fluoride include tetrabutylammonium fluoride, potassium fluoride, tetrabutylammonium difluorotriphenylsilicate and the like. The fluoride is used in an amount of about 0.000001 to 5.0 mol, preferably about 0.0001 to 2.0 mol, per 1 mol of compound (XX). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, esters, water and the like or a mixed solvent thereof and the like are preferable. While the reaction time varies depending on the reagent and solvent to be used, generally 10 min to 100 hr, preferably 30 min to 50 hr. The reaction temperature is −10° C. to 250° C., preferably 0° C. to 150° C.

Compound (XXII-a) wherein Xa, Xb and Xe are each a carbon atom can be produced by subjecting compound (XXI) to an oxidation reaction. The oxidation reaction can be performed by a method similar to the production method of compound (XX) from compound (XVI).

Compound (XXV) can be produced by reacting compound (XXIII) with carboxylic acid represented by the formula (XXIV), a salt thereof or a reactive derivative thereof. As the reactive derivative of the carboxylic acid, for example, acid halides such as acid chloride, acid bromide and the like, acid amides with pyrazole, imidazole, benzotriazole and the like, acid anhydrides such as acetic anhydride, propionic anhydride, butyric anhydride and the like, acid azides, active esters such as diethoxyphosphoric acid ester, diphenoxyphosphoric acid ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone and the like, active thioesters such as 2-pyridyl thioester, 2-benzothiazolyl thioester etc., and the like can be mentioned. Instead of using the reactive derivative, the carboxylic acid or a salt thereof may be directly reacted with compound (XXIII) in the presence of a suitable condensation agent. As the condensation agent, for example, N,N'-disubstituted carbodiimides such as N,N'-dicyclohexylcarbodiimide, 1-ethyl-3-(3-dimethylaminopropyl)carbodiimide (WSC) hydrochloride and the like, azolides such as N,N'-carbonyldiimidazole and the like, dehydrating agents such as N-ethoxycarbonyl-2-ethoxy-1,2-dihydroquinoline, phosphorus oxychloride, alkoxyacetylene and the like, 2-halogenopyridinium salts such as 2-chloromethylpyridinium iodide, 2-fluoro-1-methylpyridinium iodide etc., and the like can be mentioned. When the condensation agent is used, the reaction is considered to proceed via a reactive derivative of carboxylic acid. The carboxylic acid, a salt thereof or a reactive derivative thereof is generally used in an amount of about 1.0 to 5.0 mol, preferably about 1.0 to 2.0 mol, per 1 mol of compound (XXIII). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons, nitriles, sulfoxides, aromatic organic bases and the like or a mixed solvent thereof and the like are preferable. When an acidic substance is released by the reaction, the reaction can be performed in the presence of a deacidifying agent to remove the acidic substance from the reaction system. Examples of the deacidifying agent include inorganic bases, basic salts, organic bases and the like. While the reaction time varies depending on the reagent and solvent to be used, it is generally 10 min to 50 hr, preferably 30 min to 10 hr. The reaction temperature is generally 0° C. to 150° C., preferably 0° C. to 100° C.

Compound (XXVI) can be produced by reacting compound (XXV) with a dehydrating agent. Examples of the dehydrating agent include diphosphorus pentoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, trifluoroacetic anhydride and the like. The dehydrating agent is used in an amount of about 1.0 to 1000 mol, preferably about 1.0 to 100 mol, per 1 mol of compound (XXV). This reaction is advantageously performed without solvent or in a solvent inert to the reaction. While the solvent is not particularly limited as long as the reaction proceeds, solvents such as ethers, aromatic hydrocarbons, saturated hydrocarbons, halogenated hydrocarbons, nitrites and the like or a mixed solvent thereof and the like are preferable. When an acidic substance is released by the reaction, the reaction can be performed in the presence of a deacidifying agent to remove the acidic substance from the reaction system. Examples of the deacidifying agent include inorganic bases, basic salts, organic bases and the like. While the reaction time varies depending on the reagent and solvent to be used, it is generally 10 min to 50 hr, preferably 30 min to 24 hr. The reaction temperature is generally 0° C. to 150° C., preferably 20° C. to 80° C.

Compound (XXVII) can be produced by reacting compound (XXVI) with maleic anhydride. The maleic anhydride is used in an amount of about 1.0 to 100 mol, preferably about 1.0 to 10 mol, per 1 mol of compound (XXVI). This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides and the like or a mixed solvent thereof and the like are preferable. While the reaction time varies depending on the reagent and solvent to be used, it is generally 10 min to 50 hr, preferably 30 min to 24 hr. The reaction temperature is generally −20° C. to 150° C., preferably 0° C. to 50° C.

Compound (XXVIII) can be produced by subjecting compound (XXVII) to an isomerization reaction, followed by esterification. The isomerization reaction can be performed by a heat treatment or a reaction using an acidic substance. Examples of the acidic substance include inorganic acids, organic acids, boron trifluoride ether complex and the like. The amount of the acidic substance to be used is about 0.01 to 100 mol, preferably about 0.01 to 5.0 mol, per 1 mol of compound (XXVII). This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, water and the like or a mixed solvent thereof and the like are preferable. When alcohol is used as a solvent, an esterification reaction with the solvent used may proceed subsequent to isomerization reaction. While the reaction time varies depending on the reagent and solvent to be used, it is generally 10 min to 100 hr, preferably 30 min to 24 hr. The reaction temperature is generally −10° C. to 200° C., preferably −10° C. to 150° C. The esterification reaction is performed by, for example, the method described in 4th Ed. Jikken Kagaku Koza (Courses in Experimental Chemistry), vol. 22, pages 43-54 (The Chemical Society of Japan Ed.), or a method analogous thereto.

Compound (XXX) can be produced by an alkylation reaction of compound (XXVIII) with an alkyl halide represented by the formula (XXIX) in the presence of a base. The alkyl halide is used in an amount of about 1.0 to 100 mol, preferably about 1.0 to 10 mol, per 1 mol of compound (XXVIII). Examples of the base include inorganic bases, basic salts, organic bases, metal alkoxides, alkali metal hydrides, metal amides and the like. The base is used in an amount of about 1.0 to 20 mol, preferably about 1.0 to 5.0 mol, per 1 mol of compound (XXVIII). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, ketones, aromatic organic bases and the like or a mixed solvent thereof and the like are preferable. While the reaction time varies depending on the reagent and solvent to be used, it is generally 10 min to 100 hr, preferably 30 min to 24 hr. The reaction temperature is generally −20° C. to 200° C., preferably −10° C. to 150° C.

Compound (XXXI) can be produced by subjecting compound (XXX) to a cyclization reaction in the presence of a base. Examples of the base include metal alkoxides, alkali metal hydrides, metal amides and the like. The base is used in an amount of about 0.0001 to 20 mol, preferably about 0.01 to 5.0 mol, per 1 mol of compound (XXX). In addition, a metal alkoxide may be prepared by reacting metal hydrides with, for example, methanol, ethanol and the like in the reaction system and used. This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, sulfoxides, aromatic organic bases and the like or a mixed solvent thereof and the like are preferable. While the reaction time varies depending on the reagent and solvent to be used, it is generally 10 min to 100 hr, preferably 30 min to 24 hr. The reaction temperature is generally −20° C. to 200° C., preferably 0° C. to 150° C.

Compound (XXXII) can be produced by subjecting compound (XXXI) to a decarboxylation reaction. The decarboxylation reaction can be performed by a method known per se, or a method analogous thereto and, for example, a method using an acidic substance or a method analogous thereto and the like can be mentioned. Examples of the acidic substance include inorganic acids, organic acids and the like. The acidic substance is used in an amount of about 0.0001 to 20 mol, preferably about 0.01 to 5.0 mol, per 1 mol of compound (XXXI). This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, sulfoxides, organic acids, inorganic acids, water and the like or a mixed solvent thereof and the like are preferable. While the reaction time varies depending on the reagent and solvent to be used, it is generally 10 min to 200 hr, preferably 30 min to 100 hr. The reaction temperature is generally 0° C. to 200° C., preferably 0° C. to 150° C.

Compound (XXXIII) can be produced by subjecting compound (XXXII) to a reduction reaction. The reduction reaction can be performed by a method similar to the production method of compound (XVI) from compound (XVIII). Compound (XXXVI) can be produced by subjecting compound (XXXIII) to a cyclization reaction in the presence of a base. The cyclization reaction can be performed by a method similar to the production method of compound (XXXI) from compound (XXX). Compounds (XXXII) and (XXXIII) wherein $R^{51}$ or $R^{5j}$ is a hydrogen atom, or both are hydrogen atoms, are esterified to produce ester forms thereof. The esterification reaction can be performed by, for example, the method described in 4th Ed. Jikken Kagaku Koza (Courses in Experimental Chemistry), vol. 22, pages 43-54 (The Chemical Society of Japan Ed.), or a method analogous thereto. Compound (XXII-b) wherein Xa, Xb, Xd and Xe are each a carbon atom, and Xc is a nitrogen atom can be produced by subjecting compound (XXXVI) to a decarboxylation reaction. The decarboxylation reaction can be performed by a method similar to the production method of compound (XXXII) from compound (XXXI). Compounds (XXXVI) and (XXII-b) can also be produced by subjecting compound (XXX) to a cyclization reaction, followed by a decarboxylation reaction and a reduction reaction. The cyclization reaction can be performed by a method similar to the production method of compound (XXXI) from compound (XXX), the decarboxylation reaction can be performed by a method similar to the production method of compound (XXXII) from compound (XXXI), and the reduction reaction can be performed by a method similar to the production method of compound (XVI) from compound (XVIII).

Compound (XXII-e) can be produced by subjecting compound (XXII-c) to an aldol condensation with an aldehyde or ketone derivative to give compound (XXII-d), followed by a reduction reaction. The aldol condensation is performed by condensation of compound (XXII-c) and an aldehyde or ketone derivative represented by the formula $R^{4i}COR^{4j}$ in the presence of a base to give a single configuration isomer of E form or Z form or a mixture of E and Z isomers. The aldehyde or ketone derivative is used in an amount of about 1.0 to 50 mol, preferably about 1.0 to 5.0 mol, per 1 mol of compound (XXII-c). Examples of the base include inorganic bases, basic salts, organic bases, metal alkoxides, alkali metal hydrides, metal amides and the like. The base is used in an amount of about 1.0 to 5.0 mol, preferably about 1.0 to 2.5 mol, per 1 mol of compound (XXII-c). In addition, basic alumina and the like (e.g., ICN Alumina B, Akt. 1 manufactured by ICN and the like) can also be used as a base. In this case, alumina and the like are used in an amount of about 1 g to 500 g, preferably about 5 g to 100 g, per 1 g of compound (XXII-c). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, aromatic organic bases and the like or a mixed solvent thereof and the like are preferable. While the reaction time varies depending on the reagent and solvent to be used, it is generally 30 min to 48 hr, preferably 30 min to 5 hr. The reaction temperature is generally −78° C. to 200° C., preferably −10° C. to 150° C. In addition, compound (XXII-d) can also be produced by dehydrating aldol type intermediate, which is obtained in the presence of a base such as lithium diisopropylamide and the like, in the presence of an acid catalyst such as p-toluenesulfonic acid and the like at room temperature to under heating. The reduction reaction can be performed by a method similar to the production method of compound (XVI) from compound (XVIII).

As the aldehyde or ketone derivative represented by the formula $R^{4i}COR^{4j}$, a commercially available product may be used or it can be produced according to a method known per se or a method analogous thereto.

Compound (XXXVII-a) wherein m is 1 can be produced by subjecting nitrile to a base treatment to give carbanion, which is reacted with compound (XXII) to give compound (XXXVI), which is then subjected to a dehydrating reaction. Compound (XXXVII-a) can be obtained as a single isomer or a mixture of isomers. Examples of the nitrile include a compound represented by the formula $R^3$—$CH_2CN$. The nitrile is used in an amount of about 1.0 to 10 mol, preferably about 1.0 to 1.5 mol, per 1 mol of compound (XXII). Examples of the base include metal alkoxides, alkali metal hydrides, metal amides and the like. The base is used in an amount of about 1.0 to 10 mol, preferably about 1.0 to 1.5 mol, per 1 mol of compound (XXII). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 48 hr, preferably 30 min to 5 hr. The reaction temperature is generally −78° C. to 100° C., preferably −78° C. to 50° C. Examples of the catalyst to be used for the dehydrating reaction include acidic catalysts such as inorganic acids, organic acids, boron trifluoride ether complex and the like, basic catalysts such as inorganic bases, basic salts and the like, and the like. In addition, for example, a dehydrating agent such as diphosphorus pentoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, trifluoroacetic anhydride and the like may be used. This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, sulfoxides and the like or a mixed solvent thereof and the like are preferable. While the reaction time varies depending on the reagent and solvent to be used, it is generally 30 min to 24 hr, preferably 30 min to 5 hr. The reaction temperature is generally 0° C. to 200° C., preferably 0° C. to 150° C.

As the nitrile derivative represented by the formula $R^3$—$CH_2CN$, a commercially available product may be used, or it can be produced according to a method known per se or a method analogous thereto.

Compound (XXXVII-a) wherein m is 1 can also be produced by reacting phosphonate carbanion, produced by a base treatment of alkylphosphonic acid diester, with compound (XXII). Compound (XXXVII-a) can be obtained as a single isomer or a mixture of isomers. Examples of the alkylphosphonic acid diester include diethyl cyanomethylphosphonate, diethyl (1-cyanoethyl)phosphonate and the like. The alkylphosphonic acid diester is used in an amount of about 1.0 to 5.0 mol, preferably about 1.0 to 2.0 mol, per 1 mol of compound (XXII). Examples of the base include metal alkoxides, alkali metal hydrides, metal amides and the like. The base is used in an amount of about 1.0 to 5.0 mol, preferably about 1.0 to 1.5 mol, per 1 mol of compound (XXII). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 30 min to 50 hr, preferably 1 hr to 10 hr. The reaction temperature is generally −78° C. to 200° C., preferably 0° C. to 150° C.

Compound (XXXVIII) can be produced by treating compound (XXII) with trimethylsilyl cyanide in the presence of Lewis acid, and eliminating the resulting trimethylsilyloxy with an acid. Lewis acid is used in an amount of about 0.01 to 10 mol, preferably about 0.01 to 1.0 mol, per 1 mol of compound (XXII). This reaction is advantageously performed without solvent or in a solvent inert to the reaction. While the solvent is not particularly limited as long as the reaction proceeds, for example, solvents such as ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 10 min to 12 hr, preferably 30 min to 3 hr. The reaction temperature is generally −10° C. to 200° C., preferably −10° C. to 100° C. Examples of the acid to be used for eliminating trimethylsilyloxy include inorganic acids, organic acids, boron trifluoride ether complex and the like. The acid is used in an amount of about 1 to 100 mol, preferably about 1 to 10 mol, per 1 mol of compound (XXII). This reaction is advantageously performed without solvent or in a solvent inert to the reaction. While the solvent is not particularly limited as long as the reaction proceeds, for example, solvents such as ethers, aromatic hydrocarbons, saturated hydrocarbons, amides, halogenated hydrocarbons, sulfoxides and the like or a mixed solvent thereof and the like are preferable. While the reaction time varies depending on the reagent and solvent to be used, it is generally 30 min to 12 hr, preferably 30 min to 5 hr. The reaction temperature is generally 0° C. to 200° C., preferably 20° C. to 150° C.

Compound (XXXVII-b) wherein m is 2 can be produced from compound (XXXVII-a) according to a known carbon chain extension reaction. For example, a cyano form may be hydrolyzed under alkaline or acidic conditions to give a carboxy form, which is led to an ester form, subjected to a reduction reaction to give an alcohol form, then a reaction via halogenation and cyanation and the like.

Compound (XXXIX) can be produced by subjecting compound (V) to a reduction reaction. The reduction reaction can be performed by a method similar to the production method of compound (XVI) from compound (XVIII).

Compound (VIII) can be produced by subjecting compound (V) to a decarboxylation reaction. The decarboxylation reaction can be performed by a method similar to the production method of compound (XXXII) from compound (XXXI).

Compound (XL) can be produced by a Mannich reaction of compound (VIII) with dimethylamine and aldehyde. Examples of the aldehyde include a compound represented by the formula $R^3$—CHO. Dimethylamine and the aldehyde are each generally used in an amount of about 0.8 to 5.0 mol, preferably about 1.0 to 2.0 mol, per 1 mol of compound (VIII). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, water and the like or a mixed solvent thereof and the like are preferable. While the reaction time varies depending on the reagent and solvent to be used, it is generally 10 min to 50 hr, preferably 30 min to 24 hr. The reaction temperature is generally 0° C. to 150° C., preferably 0° C. to 100° C.

As the aldehyde represented by the formula $R^3$—CHO, a commercially available product may be used, or it can be produced according to a method known per se or a method analogous thereto.

Compound (XLI) can be produced by an alkylation reaction of compound (XL) with iodomethane. Iodomethane is used in an amount of about 1.0 to 100 mol, preferably about 1.0 to 10 mol, per 1 mol of compound (XL). To promote the reaction, the reaction can be performed in the presence of a base. Examples of the base include inorganic bases, basic salts, metal alkoxides and the like can be mentioned. The base is used in an amount of about 1.0 to 20 mol, preferably about 1.0 to 5.0 mol, per 1 mol of compound (XL). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides, ketones, aromatic organic bases and the like or a mixed solvent thereof and the like are preferable. While the reaction time varies depending on the reagent and solvent to be used, it is generally 10 min to 50 hr, preferably 30 min to 24 hr. The reaction temperature is generally −20° C. to 100° C., preferably 0° C. to 80° C.

Compound (XXXVII-a) can be produced by reacting compound (XXXIX) with trimethylsilyl cyanide in the presence of Lewis acid. Lewis acid is used in an amount of about 0.01 to 10 mol, preferably about 0.01 to 1.0 mol, per 1 mol of compound (XXXIX). This reaction is advantageously performed without solvent or in a solvent inert to the reaction. While the solvent is not particularly limited as long as the reaction proceeds, for example, solvents such as ethers, aromatic hydrocarbons, saturated hydrocarbons, amides, halogenated hydrocarbons and the like or a mixed solvent thereof and the like are preferable. While the reaction time varies depending on the reagent and solvent to be used, it is generally 10 min to 12 hr, preferably 30 min to 3 hr. The reaction temperature is generally −10° C. to 200° C., preferably −10° C. to 100° C.

Compound (XXXVII-a) can be produced by reacting compound (XLI) with cyano compound. As the cyano compound, for example, sodium cyanide, potassium cyanide, and mixtures thereof and the like can be mentioned. In addition, it can be prepared by reacting hydrogen cyanide with, for example, a basic substance such as sodium hydroxide, potassium hydroxide, sodium carbonate, potassium carbonate and the like in the reaction system and used. The cyano compound is used in an amount of about 0.8 to 10 mol, preferably about 1.0 to 2.0 mol, per 1 mol of compound (XLI). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons, sulfoxides and the like or a mixed solvent thereof and the like are preferable. In addition, water and the above-mentioned organic solvent insoluble or hardly soluble in water can also be used in the presence of a phase-transfer catalyst. Examples of the phase-transfer catalyst include quaternary ammonium salts such as tetrabutylammonium bromide, benzyltriethylammonium chloride and the like, and quaternary phosphonium salts. The amount of the phase-transfer catalyst to be used is about 0.001 to 10 mol, preferably about 0.005 to 0.5 mol, per 1 mol of compound (XLI). While the reaction time varies depending on the reagent and solvent to be used, it is generally 5 min to 10 hr, preferably 20 min to 5 hr. The reaction temperature is generally −10° C. to 200° C., preferably 0° C. to 150° C.

Compound (XLII) can be produced as a single isomer or a mixture of isomers by subjecting compound (XXXVIII) or (XXXVII) wherein m is 1 or 2 to a reduction reaction. Examples of the reducing agent include metal hydrides and metal hydride complex compounds. Examples of the hydrogenation catalyst include catalysts such as Raney nickel, Raney cobalt and the like, and the like. The reducing agent, when it is, for example, metal hydride, is used in an amount of about 1.0 to 10 mol, preferably about 1.0 to 3.0 mol, per 1 mol of compound (XXXVIII) or (XXXVII). When the reducing agent is a metal hydride complex compound, it is used in an amount of about 1.0 to 10 mol, preferably about 1.0 to 3.0 mol, per 1 mol of compound (XXXVIII) or (XXXVII). In the case of hydrogenation, a catalyst such as Raney nickel, Raney cobalt and the like is used in an amount of about 10 to 5000 wt %, preferably about 100 to 2000 wt %, relative to compound (XXXVIII) or (XXXVII). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, esters, organic acids, water and the like or a mixed solvent thereof and the like are preferable. When a catalyst such as Raney nickel and Raney cobalt is used, amines such as ammonia and the like may be further added to suppress the side reaction. The reaction time varies depending on the activity and amount of the catalyst to be used, and is generally 30 min to 200 hr, preferably 1 hr to 50 hr. The reaction temperature is generally 0° C. to 120° C., preferably 20° C. to 80° C. When a catalyst such as Raney nickel, Raney cobalt and the like is used, the hydrogen pressure is generally 1 to 100 atm.

Compound (I) can be produced by reacting compound (XLII) with carboxylic acid, a salt thereof or a reactive derivative thereof or isocyanate. Examples of the carboxylic acid include a compound represented by the formula $R^1$—COOH. Examples of the reactive derivative of carboxylic acid include acid halides such as acid chloride, acid bromide and the like, acid amides with pyrazole, imidazole, benzotriazole and the like, acid anhydrides such as acetic anhydride, propionic anhydride, butyric anhydride and the like, acid azides, active esters such as diethoxyphosphoric acid ester, diphenoxyphosphoric acid ester, p-nitrophenyl ester, 2,4-dinitrophenyl ester, cyanomethyl ester, pentachlorophenyl ester, ester with N-hydroxysuccinimide, ester with N-hydroxyphthalimide, ester with 1-hydroxybenzotriazole, ester with 6-chloro-1-hydroxybenzotriazole, ester with 1-hydroxy-1H-2-pyridone and the like, active thioesters such as 2-pyridyl thioester, 2-benzothiazolyl thioester and the like, and the like. Instead of using the reactive derivatives, carboxylic acid or a salt thereof may be directly reacted with compound (XLII) in the presence of a suitable condensation agent. Examples of the condensation agent include N,N'-disubstituted carbodiimides such as N,N'-dicyclohexylcarbodiimide, 1-ethyl-3-(3-dimethylaminopropyl)carbodiimide (WSC) hydrochloride and the like, azolides such as N,N'-carbonyldiimidazole and the like, dehydrating agents such as N-ethoxycarbonyl-2-ethoxy-1,2-dihydroquinoline, phosphorus oxychloride, alkoxyacetylene and the like, 2-halogenopyridinium salts such as 2-chloromethylpyridinium iodide, 2-fluoro-1-methylpyridinium iodide and the like, and the like. When these condensation agents are used, the reaction is considered to proceed via a reactive derivative of carboxylic acid. As the isocyanate, for example, a compound represented by the formula $R^1$—NCO can be mentioned. The carboxylic acid, a salt thereof or a reactive derivative thereof, or the isocyanate is used in an amount of generally about 1.0 to 5.0 mol, preferably about 1.0 to 2.0 mol, per 1 mol of compound (XLII). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons, nitrites, sulfoxides, aromatic organic bases and the like or a mixed solvent thereof and the like are preferable. When an acidic substance is released by the reaction, the reaction can be performed in the presence of a deacidifying agent to remove the acidic substance from the reaction system. Examples of the deacidifying agent include basic salts, organic bases and the like. While the reaction time varies depending on the reagent and solvent to be used, it is generally 10 min to 24 hr, preferably 30 min to 4 hr. The reaction temperature is generally 0° C. to 100° C., preferably 0° C. to 70° C.

A carboxylic acid represented by the formula $R^1$—COOH, a salt thereof or a reactive derivative thereof, or an isocyanate represented by the formula $R^1$—NCO may be a commercially available product, or can also be produced by a method known per se, or a method analogous thereto.

A single isomer of compound (I) or a mixture of isomers of compound (I) can be converted to a different single isomer or a mixture of isomers at different ratio by a heat treatment, a treatment with an acid or a treatment with a base. Examples of the acid include inorganic acids, organic acids, boron trifluoride ether complex and the like. Examples of the base include inorganic bases, basic salts, organic bases, metal alkoxides, alkali metal hydrides, metal amides, organic lithiums and the like. The acid or base is used in an amount of about 0.01 to 100 mol, preferably about 0.01 to 5.0 mol, per 1 mol of compound (I). This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, water and the like or a mixed solvent thereof and the like are preferable. While the reaction time varies depending on the reagent and solvent to be used, it is generally 10 min to 100 hr, preferably 30 min to 24 hr. The reaction temperature is generally $-10°$ C. to $200°$ C., preferably $-10°$ C. to $150°$ C.

Compounds (XXXVII-a), (XXXVII-b) and (XLII) can be obtained by a method similar to the isomerization method of compound (I), as their different single isomer or a mixture of isomers at different ratios.

When a compound (I) wherein the double bond moiety is reduced is to be produced, the compound can be produced by subjecting the double bond moiety of compound (I) to a reduction reaction. The reduction reaction is generally carried out using a reducing agent according to a conventional method. Examples of the reducing agent include metal hydride, metal hydride complex compound, borane complex, alkylboranes, diborane, metals, alkali metal (e.g., sodium, lithium and the like)/liquid ammonia (Birch reduction) and the like. The amount of the reducing agent to be used is appropriately determined according to the kind of the reducing agent. For example, metal hydride, metal hydride complex compound, borane complex, alkylboranes or diborane is used in an amount of about 0.25 to 10 mol, preferably about 0.5 to 5 mol, per 1 mol of compound (I), and metal (including alkali metal to be used for Birch reduction) is used in an amount of about 1.0 to 20 mol, preferably about 1.0 to 5.0 mol, per 1 mol of compound (I). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, organic acids, water and the like, or a mixed solvent thereof and the like are preferable. While the reaction time varies depending on the reagent and solvent to be used, it is generally 10 min to 100 hr, preferably 30 min to 50 hr. The reaction temperature is generally $-20°$ C. to $100°$ C., preferably $0°$ C. to $80°$ C. In addition, a hydrogenation reaction enables reduction. In this case, for example, a catalyst such as palladium carbon, platinum(IV) oxide, Raney nickel, Raney cobalt etc., or the like is used. The catalyst is used in an amount of about 1.0 to 300 wt %, preferably about 10 to 20 wt % relative to compound (I). Various hydrogen sources can also be used instead of gaseous hydrogen. As the hydrogen source, for example, formic acid, ammonium formate, triethylammonium formate, sodium phosphinate, hydrazine and the like are used. The hydrogen source is used in an amount of about 1.0 to 10 mol, preferably about 1.0 to 5.0 mol, per 1 mol of compound (I). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, esters, organic acids and the like or a mixed solvent thereof and the like are preferable. While the reaction time varies depending on the kind and amount of the reducing agent and the activity and amount of the catalyst to be used, it is generally 30 min to 100 hr, preferably 1 hr to 50 hr. The reaction temperature is generally $-20°$ C. to $120°$ C., preferably $0°$ C. to $80°$ C. When hydrogenation catalyst is used, the pressure of hydrogen is generally 1 to 100 atm. When compound (XXXVII-a), (XXXVII-b) or (XLII) wherein the double bond moiety is reduced is to be produced, it can be produced by a method similar to the method of subjecting the double bond moiety of compound (I) to a reduction reaction.

Compound (I) wherein $R^2$ is a hydrocarbon group optionally having substituent(s) can be produced by an alkylation reaction of compound (I) wherein $R^2$ is hydrogen using a corresponding alkylating agent (e.g., alkyl halide, sulfonic acid ester of alcohol and the like) in the presence of a base. Examples of the base include inorganic bases, basic salts, organic bases, metal alkoxides, alkali metal hydrides, metal amides and the like. The base is used in an amount of about 1.0 to 5.0 mol, preferably about 1.0 to 2.0 mol, per 1 mol of compound (I). This reaction is advantageously performed using a solvent inert to the reaction. While the solvent is not particularly limited as long as the reaction proceeds, for example, solvents such as ethers, aromatic hydrocarbons, saturated hydrocarbons, amides, halogenated hydrocarbons, nitrites, sulfoxides and the like or a mixed solvent thereof and the like are preferable. While the reaction time varies depending on the reagent and solvent to be used, it is generally 30 min to 48 hr, preferably 30 min to 6 hr. The reaction temperature is generally $-20°$ C. to $200°$ C., preferably $-10°$ C. to $150°$ C.

Compound (XLV) can be produced by condensing compound (XLIII) and compound (XLIV) in the presence of a metal catalyst. The condensation reaction can be performed by a method similar to the production method of compound (XVIII) from compound (XIII) and compound (XVII). Compound (XLVII) can be produced by condensing compound (XLIII) and compound (XLVI) in the presence of a metal catalyst. The condensation reaction can be performed by a method similar to the production method of compound (XVIII) from compound (XIII) and compound (XVII). Compound (XLVII) can also be produced by subjecting compound (XLV) and ammonia to a condensation reaction. The condensation reaction can be performed by a method similar to the production method of compound (XXV) from compound (XXIII) and compound (XXIV). Compound (XLVIII) can be produced by subjecting compound (XLVII) to a reduction reaction. The reduction reaction can be performed by a method similar to the production method of compound (XVI) from compound (XVIII). Compound (XLIX) can be produced by reacting compound (XLVIII) with a dehydrating agent. Examples of the dehydrating agent include diphosphorus pentoxide, phosphorus oxychloride, phosphorus pentachloride, triphenylphosphine, phosgene, N,N'-dicyclohexylcarbodiimide, alumina, sodium dioxide, thionyl chloride, methanesulfonyl chloride, trifluoroacetic anhydride and the like. The dehydrating agent is used in an amount of about 1.0 to 1000 mol, preferably about 1.0 to 100 mol, per 1 mol of compound (XLVIII). This reaction is advantageously performed without solvent or in a solvent inert to the reaction.

While the solvent is not particularly limited as long as the reaction proceeds, solvents such as ethers, aromatic hydrocarbons, saturated hydrocarbons, halogenated hydrocarbons, nitrites and the like or a mixed solvent thereof and the like are preferable. When an acidic substance is released by the reaction, the reaction can be performed in the presence of a deacidifying agent to remove the acidic substance from the reaction system. Examples of the deacidifying agent include inorganic bases, basic salts, organic bases and the like. While the reaction time varies depending on the reagent and solvent to be used, it is generally 10 min to 50 hr, preferably 30 min to 24 hr. The reaction temperature is generally 0° C. to 150° C., preferably 20° C. to 80° C. Compound (L) wherein m is 1 or 2 can be produced by subjecting compound (XLVII) to a reduction reaction. The reduction reaction can be performed by a method similar to the production method of compound (XVI) from compound (XVIII). Compound (L) can also be produced by subjecting compound (XLIX) to a reduction reaction. The reduction reaction can be performed by a method similar to the production method of compound (XVI) from compound (XVIII). In addition, a known carbon chain extension reaction of compound (XLIX) can also be performed before subjecting the compound to a reduction reaction. For carbon chain extension reaction, for example, a cyano form may be hydrolyzed under alkaline or acidic conditions to give a carboxy form, which is led to an ester form, subjected to a reduction reaction to give an alcohol form, then a reaction via halogenation and cyanation and the like. Compound (LI) wherein m is 1 or 2 can be produced by reacting compound (L) with carboxylic acid, a salt thereof or a reactive derivative thereof or isocyanate. These reactions can be performed by a method similar to the production method of compound (I) from compound (XLII). Compound (LII) wherein m is 1 or 2 can be produced by an alkylation reaction of compound (LI) using alkyl halide represented by the formula (VII). Compound (VII) is used in an amount of about 1.0 to 10 mol, preferably about 1.0 to 5 mol, per 1 mol of compound (LI). To promote the reaction, the reaction can be performed in the presence of a base. Examples of the base include inorganic bases, basic salts, metal alkoxides and the like can be mentioned. The base is used in an amount of about 1.0 to 10 mol, preferably about 1.0 to 5.0 mol, per 1 mol of compound (LI). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, ketones, aromatic organic bases and the like or a mixed solvent thereof and the like are preferable. While the reaction time varies depending on the reagent and solvent to be used, it is generally 10 min to 50 hr, preferably 30 min to 24 hr. The reaction temperature is generally −20° C. to 150° C., preferably 0° C. to 100° C.

Compound (I-a) wherein Xa and Xe are each a carbon atom, Xb is a nitrogen atom, and m is 1 or 2 can be produced by subjecting compound (LII) to a cyclization reaction in the presence of a base. Examples of the base include inorganic bases, basic salts, metal alkoxides and the like can be mentioned. The base is used in an amount of about 1.0 to 30 mol, preferably about 1.0 to 5.0 mol, per 1 mol of compound (LII). This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, sulfoxides, esters, ketones, aromatic organic bases and the like or a mixed solvent thereof and the like are preferable. While the reaction time varies depending on the reagent and solvent to be used, it is generally 10 min to 50 hr, preferably 30 min to 12 hr. The reaction temperature is generally 0° C. to 150° C., preferably 0° C. to 120° C.

Compound (XLII), (L), (LI), (LII) or (I-a), wherein $R^2$ is a hydrocarbon group optionally having substituent(s), can be produced by a method similar to the production method of compound (I) wherein $R^2$ is a hydrocarbon group optionally having substituent(s).

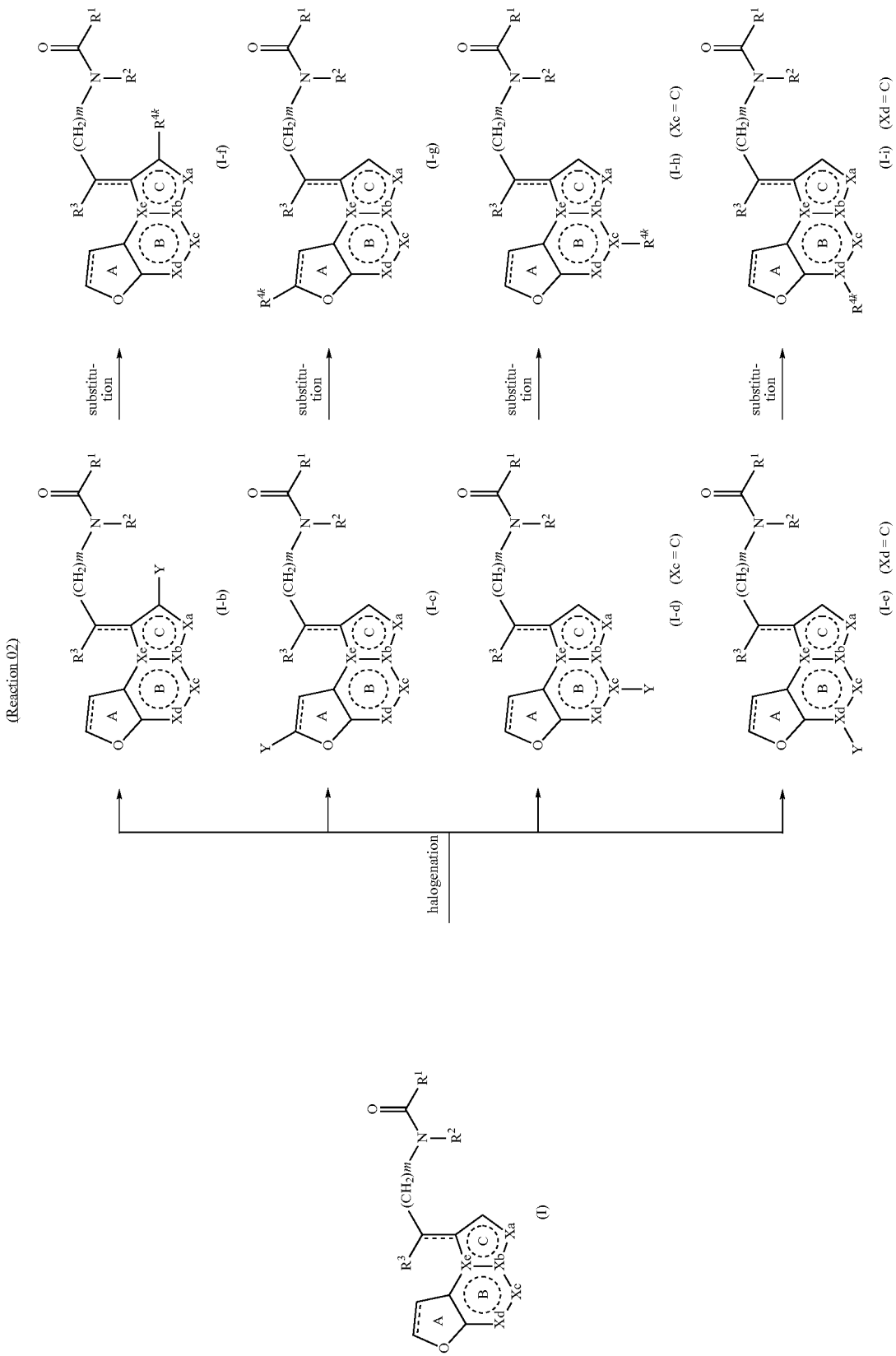

Compound (I-f) can be produced by reacting compound (I) with a halogenating agent to give compound (I-b), then subjecting the compound to a condensation reaction using organic boronic acid or organic boronic acid ester and a metal catalyst. Examples of the halogenating agent include phosphorus halide, succinimides, halogen, thionyl chloride, and mixtures thereof and the like. The halogenating agent is used in an amount of about 1.0 to 100 mol, preferably about 1.0 to 10 mol, per 1 mol of compound (I). To promote the reaction, the reaction can be performed in the presence of a base. Examples of the base include inorganic bases, basic salts and the like. This reaction is advantageously performed without solvent or in a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitriles, sulfoxides, acid anhydrides, organic acids, inorganic acids, water and the like or a mixed solvent thereof and the like are preferable. While the reaction time varies depending on the reagent and solvent to be used, it is generally 10 min to 50 hr, preferably 30 min to 12 hr. The reaction temperature is generally 0° C. to 200° C., preferably 10° C. to 100° C.

The condensation reaction is performed by reacting compound (I-b) with organic boronic acid or organic boronic acid ester in the presence of a metal catalyst. Examples of the organic boronic acid and organic boronic acid ester include a compound represented by the formula $R^{4k}$-M wherein M is the boron atom part of the organic boronic acid or organic boronic acid ester. Examples of the M include dihydroxyboranyl, 4,4,5,5-tetramethyl-1,3,2-dioxaborolan-2-yl and the like are preferable. As the metal catalyst, palladium compound is preferable. The reaction is generally performed in the presence of a base. Examples of the base include inorganic bases, basic salts and the like. The organic boronic acid or organic boronic acid ester is used in an amount of about 0.1 to 10 mol, preferably about 0.8 to 2.0 mol, per 1 mol of compound (I-b). The metal catalyst is used in an amount of about 0.000001 to 5.0 mol, preferably about 0.0001 to 1.0 mol, per 1 mol of compound (I-b). The base is used in an amount of about 1.0 to 20 mol, preferably about 1.0 to 5.0 mol, per 1 mol of compound (I-b). When a metal catalyst unstable to oxygen is used for these reactions, the reaction is preferably performed, for example, in an inert gas stream such as argon gas, nitrogen gas and the like. This reaction is advantageously performed using a solvent inert to the reaction. While the solvent is not particularly limited as long as the reaction proceeds, for example, solvents such as alcohols, ethers, aromatic hydrocarbons, saturated hydrocarbons, amides, halogenated hydrocarbons, nitrites, esters, water and the like or a mixed solvent thereof and the like are preferable. While the reaction time varies depending on the reagent and solvent to be used, it is generally 1 min to 200 hr, preferably 5 min to 100 hr. The reaction temperature is −10° C. to 250° C., preferably 0° C. to 150° C.

An organic boronic acid or an organic boronic acid ester represented by the formula $R^{4k}$-M may be a commercially available one, or can also be produced by a method known per se, or a method analogous thereto. Compound (I-f) can also be produced by subjecting compound (I-b) to a desired substituent exchange reaction known per se. The reaction can be carried out, for example, by the method described in Shin Jikken Kagaku Koza (New Experimental Chemistry Course), vols. 14 and 15 (edited by the Chemical Society of Japan) and the like, or a method analogous thereto. Compounds (I-g), (I-h) and (I-i) can be produced by a method similar to the method for producing compound (I-f) from compound (I).

A compound represented by the formula

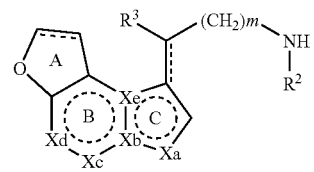

wherein each symbol is as defined above, or a salt thereof (hereinafter sometimes to be abbreviated as compound (A)), which is obtained in the reaction step to give the aforementioned compound (I), is a novel compound, and can be used as a starting material of the compound of the present invention.

In Compound (A), $R^2$ is preferably a hydrogen atom.
As $R^3$, a hydrogen atom is preferable.
As Xa, N or $CH_2$ is preferable.
As Xb, N or C is preferable.
As Xc, CH or N is preferable.
As Xd, CH or N is preferable.
As Xe, C is preferable.
As m, 1 is preferable.
As tricycle consisting of ring A, ring B and ring C, a tricycle represented by the following formula is preferable.

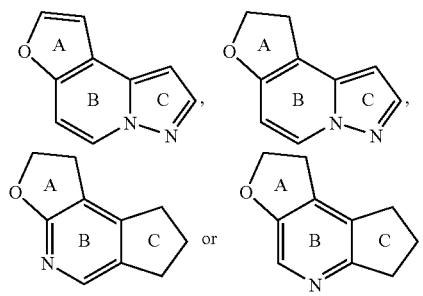

It may have, on ring C, one substituent selected from (1) $C_{1-6}$ alkyl optionally having 1 to 3 halogen atoms, (2) $C_{3-6}$ cycloalkyl, (3) $C_{6-10}$ aryl optionally having 1 to 3 halogen atoms and (4) hydroxy.

Of these, preferable compounds are 2-furo[3,2-c]pyrazolo[1,5-a]pyridin-1-ylethanamine (Reference Example 36), 2-(2-phenylfuro[3,2-c]pyrazolo[1,5-a]pyridin-1-yl)ethanamine hydrochloride (Reference Example 37), 2-(8,9-dihydrofuro[3,2-c]pyrazolo[1,5-a]pyridin-1-yl)ethanamine (Reference Example 38), 2-(2-ethyl-8,9-dihydrofuro[3,2-c]pyrazolo[1,5-a]pyridin-1-yl)ethanamine (Reference Example 39), 2-(2-phenyl-8,9-dihydrofuro[3,2-c]pyrazolo[1,5-a]pyridin-1-yl)ethanamine hydrochloride (Reference Example 40), 2-(2-methyl-8,9-dihydrofuro[3,2-c]pyrazolo[1,5-a]pyridin-1-yl)ethanamine (Reference Example 41), 2-(2-cyclopropyl-8,9-dihydrofuro[3,2-c]pyrazolo[1,5-a]pyridin-1-yl)ethanamine (Reference Example 42), 2-[2-(trifluoromethyl)-8,9-dihydrofuro[3,2-c]pyrazolo[1,5-a]pyridin-1-yl]ethanamine (Reference Example 43), 2-[2-(4-fluorophenyl)-8,9-dihydrofuro[3,2-c]pyrazolo[1,5-a]pyridin-1-yl]ethanamine hydrochloride (Reference Example 44), 2-(1,2,6,7-tetrahydro-8H-cyclopenta[d]furo[2,3-b]pyridin-8-ylidene)ethanamine (Reference Example 62), 2-(1,6,7,8-tetrahydro-2H-cyclopenta[d]furo[2,3-b]pyridin-8-yl)ethanamine (Reference Example 63), 8-(2-aminoethyl)-7-isopropyl-1,6,7,8-tetrahydro-2H-cyclopenta[d]furo[2,3-b]pyridin-8-ol (Reference Example 64), (2E)-2-(1,2,6,7- tetrahydro-8H-cyclopenta[b]furo[3,2-d]pyridin-8-ylidene)ethanamine (Reference Example 73), optically active forms thereof, salts thereof and the like.

In the aforementioned respective reactions, when the starting compound has amino, carboxy or hydroxy, these groups may be protected by a protecting group generally used in the peptide chemistry and the like. In this case, the object compound can be obtained by removing the protecting group as necessary after the reaction. Introduction and removal of these protecting groups can be performed by a method known per se, for example, the method described in "Protective Groups in Organic Synthesis, $3^{rd}$ Ed." (Theodora W. Greene, Peter G. M. Wuts, Wiley-Interscience, 1999) and the like.

The configuration isomers of the aforementioned compounds (II)-(LII) can be isolated and purified by, for example, a conventional separation means such as extraction, recrystallization, distillation, chromatography and the like, when isomerization occurs, whereby a pure compound can be produced. In addition, isomerization of double bond may be promoted by heating, acid catalyst, transition metal complex, metal catalyst, radical species catalyst, photoirradiation or strong basic catalyst and the like according to the method described in Shin Jikken Kagaku Koza (New Experimental Chemistry Course), vol. 14, pp. 251-253 (edited by the Chemical Society of Japan), Jikken Kagaku Koza (Courses in Experimental Chemistry), 4th Ed., vol. 19, pp. 273-274 (edited by the Chemical Society of Japan) or a method analogous thereto, whereby a corresponding pure isomer can be obtained. While compound (I) has a stereoisomer depending on the kind of the substituent, not only the isomer itself but also a mixture thereof are encompassed in the present invention. In the above-mentioned reaction steps, where desired, compound (I) can be produced by a known hydrolysis, deprotection, acylation reaction, alkylation reaction, hydrogenation reaction, oxidation reaction, reduction reaction, carbon chain extension reaction or substituent exchange reaction, conducted individually or by a combination of two or more thereof. These reactions can be carried out, for example, according to the method described in Shin Jikken Kagaku Koza (New Experimental Chemistry Course), vols. 14 and 15, published in 1977, 1978 (edited by the Chemical Society of Japan) and the like.

Compound (I) can be isolated and purified by a known means, for example, phase transfer, concentration, solvent extraction, fractional distillation, liquid conversion, crystallization, recrystallization, chromatography and the like.

When compound (I) is obtained as a free compound, it can be converted into a desired salt by a method known per se or a modification thereof; conversely, when compound (I) is obtained as a salt, it can be converted into a free form or another desired salt by a method known per se or a modification thereof.

Compound (I) may be used as a prodrug. A prodrug of compound (I) means a compound which is converted to compound (I) with a reaction due to an enzyme, gastric acid, etc. under the physiological condition in the living body, that is, a compound which is converted to compound (I) by oxidation, reduction, hydrolysis, etc. according to an enzyme; a compound which is converted to compound (I) by hydrolysis etc. due to gastric acid, etc.

A prodrug of compound (I) may be a compound obtained by subjecting amino in compound (I) to an acylation, alkylation or phosphorylation (e.g., a compound obtained by subjecting amino in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and tert-butylation, etc.); a compound obtained by subjecting hydroxy in compound (I) to an acylation, alkylation, phosphorylation or boration (e.g., a compound obtained by subjecting hydroxy in compound (I) to an acetylation, palmitoylation, propanoylation, pivaloylation, succinylation, fumarylation, alanylation, dimethylaminomethylcarbonylation, etc.); a compound obtained by subjecting carboxy in compound (I) to an esterification or amidation (e.g., a compound obtained by subjecting carboxy in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification and methylamidation, etc.) and the like. Any of these compounds can be produced from compound (I) by a method known per se.

A prodrug for compound (I) may also be one which is converted into compound (I) under a physiological condition, such as those described in IYAKUHIN no KAIHATSU (Development of Pharmaceuticals), Vol. 7, Design of Molecules, p. 163-198, Published by HIROKAWA SHOTEN.

When compound (I) has isomers such as optical isomer, stereoisomer, positional isomer, rotational isomer and the like, and any isomers and mixtures are encompassed in compound (I). For example, when compound (I) has an optical isomer, an optical isomer separated from a racemate is also encompassed in compound (I). These isomers can be obtained as independent products by a synthesis means or a separation means (e.g., concentration, solvent extraction, column chromatography, recrystallization and the like), optical resolution methods (e.g., fractional recrystallization, chiral column method, diastereomer method and the like) and the like known per se.

Compound (I) may be a crystal, and both a single crystal and crystal mixtures are encompassed in compound (I) of the present invention. Crystals can be produced by crystallization according to crystallization methods known per se.

Compound (I) may be a solvate (e.g., hydrate etc.) or a non-solvate (e.g., non-hydrate etc.), both of which are encompassed in compound (I) of the present invention.

A compound labeled with an isotope (e.g., $^2H$, $^3H$, $^{14}C$, $^{35}S$, $^{125}I$ and the like) is also encompassed in compound (I) of the present invention.

Compound (I) and compound (I') of the present invention show high affinity for melatonin receptors ($MT_1$ receptor, $MT_2$ receptor). Since compound (I) acts as a melatonin agonist, has physiological activities such as melatonin receptor affinity and the like, shows low toxicity (e.g., acute toxicity, chronic toxicity, genetic toxicity, reproductive toxicity, cardiotoxicity, drug interaction, carcinogenicity and the like), and is superior in the stability and in vivo kinetics (absorption, distribution, metabolism, excretion and the like), it is useful as a pharmaceutical product. Compound (I) and compound (I') act as a melatonin agonist in mammals (e.g., mouse, rat, hamster, rabbit, cat, dog, bovine, sheep, monkey, human and the like), is useful as a composition with a binding affinity for melatonin receptor, particularly, a melatonin receptor agonist, and can be used as a prophylactic or therapeutic drug for a disease possibly influenced by melatonin. As the "disease possibly influenced by melatonin", for example, sleep disorders [e.g., intrinsic sleep disorders (e.g., psychophysiological insomnia and the like), extrinsic sleep disorders, circadian rhythm disorders (e.g., time-zone change syndrome (jet lag), shift work sleep disorder, irregular sleep-wake pattern, delayed sleep phase syndrome, advanced sleep phase syndrome, non-24 hour sleep-wake syndrome and the like), parasomnias, sleep disorder associated with internal or psychic disorders (e.g., chronic obstructive pulmonary disease, Alzheimer's disease, Parkinson's disease, cerebrovascular dementia, schizophrenia, depression, anxiety neurosis), insomnia and the like], neurodegenerative diseases (e.g., senile dementia, Alzheimer's disease, Parkinson's disease, Creutzfeldt-Jakob disease, amyotrophic lateral sclerosis (ALS), Huntington's disease, spinocerebellar degeneration, multiple sclerosis (MS) and the like), psychoneurotic diseases (e.g., depression, anxiety, bipolar disorder, posttraumatic stress disorder (PTSD), seasonal melancholia, schizophrenia and the like), memory disorders (e.g., senile dementia, mild cognitive impairment (MCI), amnesia and the like), ischemic central nerve disorders (e.g., cerebral infarction, cerebral hemorrhage, brain edema and the like), central nervous system injury (e.g., head trauma, spinal cord injury, whiplash injury and the like), vascular dementia (e.g., multi-infarct dementia, Binswanger's disease and the like), cancer (e.g., brain tumor, pituitary adenoma, glioma, acoustic schwannoma, retinoblastoma, thyroid cancer, pharyngeal cancer, laryngeal cancer, cancer of the tongue, thymoma, mesothelial tumor, breast cancer, lung cancer, non-small cell lung cancer, small cell lung cancer, gastric cancer, esophageal cancer, duodenal cancer, colorectal cancer, colon cancer, rectal cancer, liver cancer, hepatocellular carcinoma, pancreatic cancer, pancreatic endocrine tumor, biliary tract cancer, gallurinary bladder cancer, penile cancer, kidney cancer, renal pelvic cancer, ureteral cancer, renal cell cancer, testis tumor, prostate cancer, urinary bladder cancer, vulvar cancer, uterus cancer, cancer of uterine cervix, cancer of uterine body, uterine sarcoma, chorionic disease, vaginal cancer, ovary cancer, ovarian germ cell tumor, skin cancer, malignant melanoma, mycosis fungoides, basal cell tumor, soft tissue sarcoma, malignant lymphoma, Hodgkin's disease, osteomyelodysplasia syndrome, multiple myeloma, leukemia, acute myelocytic leukemia, chronic myelocytic leukemia, acute lymphatic leukemia, chronic lymphatic leukemia, adult T cell leukemia, chronic myeloproliferative disease, pancreatic endocrine tumor, fibrous histiocytoma, leiomyosarcoma, rhabdomyosarcoma, unknown primary cancer and the like), hyperinsulinemia, metabolic syndrome, obesity (obesity), diabetes, diabetic complications (e.g., diabetic retinopathy, diabetic neuropathy, diabetic nephropathy and the like), hypertriglyceridemia (hyperlipidemia), hypertension, circulatory disease [e.g., ischemic cardiac diseases (e.g., myocardial infarction, angina pectoris and the like), cerebral apoplexy, arteriosclerosis, arterial restenosis after PTCA and the like], lower urinary tract disease or disorder (e.g., dysuria, incontinence and the like), osteoporosis, reproductive and neuroendocrine diseases, convulsion, glaucoma, headache, irritable bowel syndrome and the like can be mentioned. In addition, it is effective for immunoregulation, cognitive enhancement, tranquilization, stress or regulation of ovulation (e.g., contraception and the like).

Compound (I) and compound (I') [sometimes to be abbreviated as "the compound of the present invention"] can be safely administered orally or parenterally (e.g., subcutaneous, topical, rectal, intravenous administrations etc.) by itself, or in the form of a pharmaceutical composition containing a pharmacologically acceptable carrier according to a conventional method (e.g., the method described in the Japanese Pharmacopoeia etc.), such as tablet (including sugar-coated tablet, film-coated tablet and the like), powder, granule, capsule, liquid, emulsion, suspension, injection, suppository, sustained-release preparation (e.g., sublingual tablet, microcapsule etc.), plaster, orally disintegrating tablet, orally disintegrating film and the like.

As pharmacologically acceptable carriers, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidizing agent, colorant, sweetening agent, adsorbent, wetting agent and the like can be used appropriately.

As the excipient, for example, lactose, sucrose, D-mannitol, starch, cornstarch, crystalline cellulose, light anhydrous silicic acid and the like can be mentioned. As the lubricant, for example, magnesium stearate, calcium stearate, talc, colloidal silica and the like can be mentioned. As the binder, for example, crystalline cellulose, sucrose, D-mannitol, dextrin, hydroxypropylcellulose, hydroxypropylmethylcellulose, polyvinylpyrrolidone, starch, sucrose, gelatin, methylcellulose, sodium carboxymethylcellulose and the like can be mentioned. As the disintegrant, for example, starch, carboxymethylcellulose, calcium carboxymethylcellulose, croscarmellose sodium, sodium carboxymethyl starch, L-hydroxypropylcellulose and the like can be mentioned. As the solvent, for example, water for injection, alcohol, propylene glycol, macrogol, sesame oil, corn oil, olive oil and the like can be mentioned. As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned. As the suspending agent, for example, surfactants such as stearyltriethanolamine, sodium lauryl sulfate, lauryl aminopropionate, lecithin, benzalkonium chloride, benzethonium chloride, glyceryl monostearate, and the like; for example, hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose etc., and the like can be mentioned. As the isotonicity agent, for example, glucose, D-sorbitol, sodium chloride, glycerol, D-mannitol and the like can be mentioned. As the buffer, for example, buffer such as phosphate, acetate, carbonate, citrate etc., and the like can be mentioned. As the soothing agent, for example, benzyl alcohol and the like can be mentioned. As the preservative, for example, p-hydroxybenzoates, chlorobutanol, benzyl alcohol, phenethyl alcohol, dehydroacetic acid, sorbic acid and the like can be mentioned. As the antioxidizing agent, for example, sulfite, ascorbic acid, α-tocopherol and the like can be mentioned.

While the dose of the compound of the present invention varies depending on the subject of administration, administration route and symptom and is not particularly limited, for example, for oral administration to adult patients for the treatment of insomnia, it is about 0.001 to about 3 mg/kg body weight, preferably about 0.005 to about 2 mg/kg body weight, more preferably about 0.01 to about 1 mg/kg body weight, as the compound of the present invention, which is the active ingredient. The dose is desirably administered about 1 to 3 times a day according to the symptom.

The content of the compound of the present invention in the above-mentioned "agent (pharmaceutical composition)" is about 0.01 to 100 wt % of the whole composition.

When the compound of the present invention is applied to each of the above-mentioned diseases, it can be used in appropriate combination with a pharmaceutical agent or a treatment method generally employed for the disease.

In the following, a combined use of the compound of the present invention with a concomitant drug is referred to as "the combination agent of the present invention".

As such concomitant drug, for example, sleep inducing agents (e.g., GABA system sleep inducing agent such as brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol etc.; non-GABA system sleep inducing agent such as eplivaserin, pruvanserin, diphenhydramine, trazodone, doxepin etc., and the like), antidepressants (e.g., fluoxetine, sertraline, paroxetine, venlafaxine, nefazodone, reboxetine, mirtazapine, imipramine hydrochloride, duloxetine, escitalopram, mifepristone, doxepin, etc.), antianxiety agents (e.g., alprazolam, bromazepam, chlordiazepoxide, diazepam, etizolam, flutoprazepam, lorazepam, etc.), therapeutic agents for Alzheimer's disease (e.g., cholinesterase inhibitors such as donepezil, rivastigmine, galanthamine, zanapezil etc.; cerebral function activators such as idebenone, memantine, vinpocetine etc.; agents for suppressing progression such as Alzhemed etc., and the like), antiparkinson agents (e.g., L-DOPA, deprenyl, carbidopa+levodopa, pergolide, ropinirole, cabergoline, pramipexole, entacaprone, lazabemide etc.), therapeutic agents for amyotrophic lateral sclerosis (e.g., riluzole, mecasermin, gabapentin, etc.), neurotrophic factors, therapeutic agents for schizophrenia (e.g., olanzapine, risperidone, quetiapine, iloperidone, etc.), hypolipidemic agents (e.g., simvastatin, fluvastatin, pravastatin, atorvastatin, etc.), antihypertensive agents (e.g., captopril, delapril, enalapril, nifedipine, nicardipine, amlodipine, alprenolol, propranolol, metoprolol, losartan, valsartan, candesartan, etc.), therapeutic agents for diabetes (e.g., pioglitazone, rosiglitazone, metformin, glibenclamide, nateglinide, voglibose, etc.), antiplatelet agents (e.g., ticlopidine, heparin, urokinase, alteplase, tisokinase, nasaruplase, cilostazol, etc.), antioxidizing agents (e.g., linolenic acid, ascorbic acid, icosapentaenoic acid, docosahexaenoic acid, tocopherol, etc.), vitamins (e.g., tocopherol, ascorbic acid, etc.), sex hormones (e.g., estrogen, estrone, estradiol, etc.), antiinflammatory agents (e.g., prednisolone, betamethasone, dexamethasone, etc.), nonsteroidal antiinflammatory agents (e.g., indomethacin, ibuprofen, acetylsalicylic acid, diclofenac, naproxen, piroxicam, etc.), COX-2 inhibitors (e.g., celecoxib, rofecoxib, etc.), cerebral circulation metabolism improving agents (e.g., nicergoline, ibudilast, ifenprodil, etc.), anticonvulsants (e.g., carbamazepine, valproic acid, clonazepam, vigabatrin, lamotrigine, gabapentin, etc.) and pharmacologically acceptable salts thereof and the like can be mentioned.

By combining the compound of the present invention and a concomitant drug, a superior effect such as
(1) the dose can be reduced as compared to single administration of the compound of the present invention or a concomitant drug,
(2) the concomitant drug can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

A combination agent of the present invention has low toxicity, and for example, the compound of the present invention and/or the above-mentioned concomitant drug can be mixed, according to a method known per se, with a pharmacologically acceptable carrier to give pharmaceutical compositions, such as tablets (including sugar-coated tablet, film-coated tablet), powders, granules, capsules, solutions, emulsions, suspensions, injections, suppositories, sustained release preparations (e.g., sublingual tablet, microcapsule etc.), plasters, orally disintegrating tablets, orally disintegrating films and the like, which can be safely administered orally or parenterally (e.g., subcutaneous, topical, rectal, intravenous administrations etc.).

As pharmacologically acceptable carriers usable for the production of the combination agent of the present invention, various organic or inorganic carrier substances conventionally used as preparation materials can be mentioned. For example, suitable amounts of additives such as excipient, lubricant, binder and disintegrant for solid preparations, or solvent, solubilizing agent, suspending agent, isotonicity agent, buffer and soothing agent for liquid preparations, and where necessary, conventional preservative, antioxidizing agent, colorant, sweetening agent, adsorbent, wetting agent and the like can be used appropriately.

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the compound of the present invention and the concomitant drug is not particularly restricted, and it is sufficient that the compound of the present invention and the concomitant drug are combined in administration. Examples of such administration mode include the following:
(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug in the combination agent of the present invention can be appropriately selected depending on an administration subject, administration route, diseases and the like.

For example, the content of the compound of the present invention in the combination agent of the present invention varies depending on the form of a preparation, and usually from about 0.01 to 100 wt %, preferably from about 0.1 to 50 wt %, further preferably from about 0.5 to 20 wt %, based on the whole preparation.

While the content of the concomitant drug in the combination agent of the present invention varies depending on the form of a preparation, it is usually from about 0.01 to 100 wt %, preferably from about 0.1 to 50 wt %, further preferably from about 0.5 to 20 wt %, based on the whole preparation.

While the content of the additives such as carrier and the like in the combination agent of the present invention varies depending on the form of a preparation, it is generally about 1 to 99.99 wt %, preferably about 10 to 90 wt %, based on the whole preparation.

Similar contents can be employed for individual preparations of the compound of the present invention and the concomitant drug.

The SEQ ID NOs in the sequence listing in the present specification shows the following sequences. SEQ ID NO: 1 shows the base sequence of cDNA fragment encoding the full-length human melatonin 1 receptor (human $MT_1$ receptor). (see Gen Bank ACCESSION No. NM_005958) SEQ ID NO: 2 shows the base sequence of cDNA fragment encoding the full-length human melatonin 2 receptor (human $MT_2$ receptor). (see Gen Bank ACCESSION No. NM_005959)

EXAMPLE

The present invention is explained in detail in the following by referring to Reference Examples, Examples, Formulation Examples and Experimental Examples. However, the examples are mere exemplifications and do not limit the present invention. The present invention may be modified without departing from the scope of the invention. In the following Reference Examples and Examples, the "room temperature" means generally about 10° C. to about 35° C., % means mol/mol % for the yield, % by volume for the solvent used for chromatography, and wt % for others. M means mol/L.

Other abbreviations used in the text mean the following.
s: singlet
d: doublet
t: triplet
q: quartet
m: multiplet
br: broad
J: coupling constant
Hz: Hertz
$CDCl_3$: deuteriochloroform
DMSO-$d_6$: deuteriodimethyl sulfoxide
METHANOL-$d_4$: deuteriomethanol
$^1$H-NMR: proton nuclear magnetic resonance The elution for the column chromatography in the Examples was performed under observation by TLC (Thin Layer Chromatography). In the TLC observation, 60F254 manufactured by Merck or NH (DM1020) manufactured by Fuji Silysia Chemical Ltd. was used as a TLC plate. Unless otherwise specified, the silica gel packed in the column was silica gel 60 (70-230 mesh) (manufactured by Merck) or PURIF-pack (SI 60 μm) (manufactured by Moritex Corporation). When described as silica gel chromatography (NH), CHROMATOREX-NH DM1020 (100-200 mesh) (manufactured by Fuji Silysia Chemical Ltd.) or PURIF-pack (NH 60 μm) (manufactured by Moritex Corporation) was used. Unless otherwise specified, moreover, the elution solvent for silica gel column chromatography is in volume ratio. As Raney cobalt, Raney cobalt catalyst ODHT-60 (manufactured by Kawaken Fine Chemicals Co., Ltd.) was used after washing with water and ethanol. Unless otherwise specified, as the palladium-carbon powder, a 10% palladium-carbon powder (50% water-containing product NX type, manufactured by N.E. Chemcat Corporation) was used.

In Reference Examples and Examples, $^1$H-NMR spectrum was measured using tetramethylsilane as the internal standard and the chemical shift is expressed in δ value and the coupling constant is expressed in Hz.

In the following Reference Examples and Examples, melting point, mass spectrum (MS) and nuclear magnetic resonance spectrum (NMR) were measured under the following conditions. Melting point apparatus: Yanagimoto micromelting point apparatus, or Buchi B-545 melting point apparatus MS measurement instrument: Waters ZMD, or Waters ZQ, ionization method: Electron Spray Ionization (ESI) NMR measurement instrument: Varian, Inc., Varian Mercury 300 (300 MHz), Bruker BioSpin AVANCE 300 (300 MHz)

Reference Example 1

(2E)-3-(2-furyl)acrylic acid

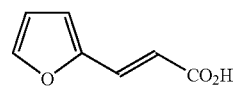

To a mixture of 2-furfural (500 g, 5.20 mol) and malonic acid (595 g, 5.72 mol) in pyridine (500 mL) was added piperidine (50 mL, 0.505 mol) at room temperature, and the mixture was stirred at 100° C. for 3 hr. The reaction solution was poured into water (1 L) and acidified with 6M hydrochloric acid. The resulting precipitate was collected by filtration to give the title compound (660 g, yield 92%).

$^1$H-NMR (DMSO-$d_6$) δ: (1H, d, J=15.9 Hz), 6.62 (1H, dd, J=3.6, 1.6 Hz), 6.92 (1H, d, J=3.6 Hz), 7.39 (1H, d, J=15.9 Hz), 7.83 (1H, d, J=1.6 Hz), 12.38 (1H, s).

Reference Example 2

(2E)-3-(2-furyl)acryloyl azide

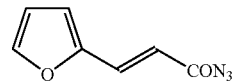

To a mixture of (2E)-3-(2-furyl)acrylic acid (660 g, 4.78 mol) and triethylamine (800 mL, 5.74 mol) in tetrahydrofuran (960 mL) was added diphenylphosphoryl azide (1.13 L, 5.26 mol) under ice-cooling. After stirring at room temperature for 4 hr, the reaction solution was poured into a mixture of ethyl acetate and saturated aqueous sodium hydrogen carbonate solution, and the mixture was extracted with ethyl acetate. The extract was dried over anhydrous sodium sulfate, and the solvent was evaporated under reduced pressure. The residue was washed with methanol to give the title compound (580 g, yield 74%).

$^1$H-NMR (DMSO-d$_6$) δ: (1H, d, J=15.7 Hz), 6.67 (1H, dd, J=3.4, 1.8 Hz), 7.10 (1H, d, J=3.4 Hz), 7.56 (1H, d, J=15.7 Hz), 7.88-7.94 (1H, m).

Reference Example 3 furo[3,2-c]pyridin-4(5H)-one

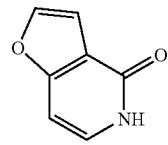

(2E)-3-(2-Furyl)acryloyl azide (150 g, 920 mmol) was added to toluene (800 mL) heated to 100° C., and the mixture was stirred for 30 min. The solvent was evaporated under reduced pressure. The residue was dissolved in orthodichlorobenzene (800 mL), and iodine (1 g) was added. The mixture was stirred at 180° C. for 2 hr, and the solvent was evaporated under reduced pressure. The residue was dissolved in methanol, the precipitate was filtered off, and the filtrate was concentrated under reduced pressure. The residue was washed with diisopropyl ether to give the title compound (100 g, yield 80%).

$^1$H-NMR (DMSO-d$_6$) δ: (1H, dd, J=7.1, 1.0 Hz), 6.92 (1H, dd, J=1.9, 1.0 Hz), 7.29 (1H, d, J=7.1 Hz), 7.86 (1H, d, J=1.9 Hz), 11.42 (1H, brs).

Reference Example 4

4-chlorofuro[3,2-c]pyridine

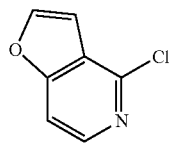

Furo[3,2-c]pyridin-4(5H)-one (72.2 g, 534 mmol) was added to phosphorus oxychloride (100 mL) heated to 120° C., and the mixture was stirred for 30 min. The solvent was evaporated under reduced pressure. Ice-cooled water was added to the residue, and the mixture was basified with 8M aqueous sodium hydroxide solution and extracted with ethyl acetate. The extract was washed with saturated brine and dried over anhydrous sodium sulfate. The solvent was evaporated under reduced pressure and the residue was purified by silica gel column chromatography (ethyl acetate/hexane=30/70) to give the title compound (66.1 g, yield 81%).

$^1$H-NMR (CDCl$_3$) δ: 7.13 (1H, dd, J=2.2, 1.0 Hz), 7.79 (1H, dd, J=5.8, 1.0 Hz), 8.27 (1H, d, J=2.2 Hz), 8.32 (1H, d, J=5.8 Hz).

Reference Example 5 furo[3,2-c]pyridine

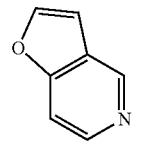

To a solution of 4-chlorofuro[3,2-c]pyridine (10.0 g, 65.1 mmol) in acetic acid (130 mL) was added zinc (10.0 g, 153 mmol), and the mixture was heated under reflux for 2 hr and filtered. The filtrate was concentrated under reduced pressure. The residue was basified with 1M aqueous sodium hydroxide solution and extracted with ethyl acetate. The extract was dried over anhydrous sodium sulfate. The solvent was evaporated under reduced pressure and the residue was purified by silica gel column chromatography (ethyl acetate) to give the title compound (5.67 g, yield 73%).

$^1$H-NMR (CDCl$_3$) δ: 6.86 (1H, dd, J=2.2, 0.8 Hz), 7.43-7.47 (1H, m), 7.65 (1H, d, J=2.2 Hz), 8.49 (1H, d, J=5.8 Hz), 8.94 (1H, d, J=0.8 Hz).

Reference Example 6

2,3-dihydrofuro[3,2-c]pyridine

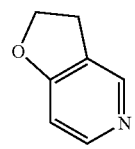

To a solution of furo[3,2-c]pyridine (500 mg, 4.20 mmol) in acetic acid (8 mL) was added 5% palladium-carbon powder (manufactured by WAKO, 250 mg), and the mixture was stirred at room temperature for 24 hr under a hydrogen atmosphere. The catalyst was filtered off, and the filtrate was concentrated under reduced pressure. The residue was dissolved in ethyl acetate, saturated aqueous sodium hydrogen carbonate solution was added, and the mixture was extracted with ethyl acetate. The extract was dried over anhydrous sodium sulfate, and the solvent was evaporated under reduced pressure to give the title compound (365 mg, yield 72%).

¹H-NMR (CDCl₃) δ: 3.25 (2H, t, J=8.8 Hz), 4.65 (2H, t, J=8.8 Hz), 6.73 (1H, d, J=5.5 Hz), 8.28 (1H, d, J=5.5 Hz), 8.34-8.35 (1H, m).

Reference Example 7

5-aminofuro[3,2-c]pyridin-5-ium 2,4-dinitrobenzenolate

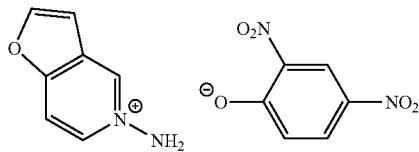

To a solution of furo[3,2-c]pyridine (960 mg, 8.06 mmol) in acetonitrile (5.0 mL) was added 1-(aminooxy)-2,4-dinitrobenzene (1.77 g, 8.89 mmol) at room temperature, and the mixture was stirred at 40° C. for 15 hr. Diethyl ether was added, and the resulting precipitate was collected by filtration and washed with diethyl ether to give the title compound (2.06 g, yield 80%).

¹H-NMR (DMSO-d₆) δ: 6.30 (1H, d, J=9.9 Hz), 7.42 (1H, dd, J=2.2, 0.8 Hz), 7.76 (1H, dd, J=9.9, 3.3 Hz), 8.21 (2H, s), 8.35 (1H, d, J=7.2 Hz), 8.55 (1H, d, J=2.2 Hz), 8.58 (1H, d, J=3.3 Hz), 8.72 (1H, dd, J=7.2, 1.6 Hz), 9.33 (1H, d, J=1.6 Hz).

Reference Example 8

5-amino-2,3-dihydrofuro[3,2-c]pyridin-5-ium 2,4-dinitrobenzenolate

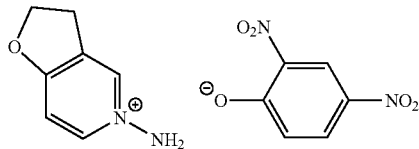

To a solution of 2,3-dihydrofuro[3,2-c]pyridine (23.8 g, 200 mmol) in acetonitrile (130 mL) was added 1-(aminooxy)-2,4-dinitrobenzene (55.0 g, 240 mmol), and the mixture was stirred at room temperature for 3 days. Diethyl ether was added, and the resulting precipitate was collected by filtration to give the title compound (57.0 g, yield 89%).

¹H-NMR (DMSO-d₆) δ: 3.33-3.43 (2H, m), 4.94 (2H, t, J=8.9 Hz), 6.33 (1H, d, J=9.6 Hz), 7.37 (1H, d, J=6.9 Hz), 7.65 (2H, s), 7.78 (1H, dd, J=9.6, 3.2 Hz), 8.49-8.53 (1H, m), 8.56-8.61 (2H, m).

Reference Example 9 ethyl furo[3,2-c]pyrazolo[1,5-a]pyridine-1-carboxylate

To a mixture of 5-aminofuro[3,2-c]pyridin-5-ium 2,4-dinitrobenzenolate (1.00 g, 3.14 mmol) and potassium carbonate (608 mg, 4.40 mmol) in dimethylformamide (20 mL) was added ethyl propiolate (350 μL, 3.45 mmol) under ice-cooling, and the mixture was stirred at room temperature for 12 hr. The reaction solution was diluted with water and extracted with ethyl acetate. The extract was dried over anhydrous sodium sulfate. The solvent was evaporated under reduced pressure and the residue was purified by silica gel column chromatography (ethyl acetate/hexane=10/90→440/60) to give the title compound (451 mg, yield 62%).

¹H-NMR (CDCl₃) δ: 1.45 (3H, t, J=7.1 Hz), 4.22 (2H, q, J=7.1 Hz), 7.19 (1H, dd, J=7.4, 0.8 Hz), 7.72-7.75 (1H, m), 7.75-7.77 (1H, m), 8.37-8.42 (2H, m).

Reference Example 10 methyl 2-phenylfuro[3,2-c]pyrazolo[1,5-a]pyridine-1-carboxylate

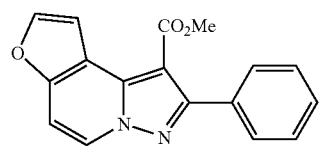

To a mixture of 5-aminofuro[3,2-c]pyridin-5-ium 2,4-dinitrobenzenolate (1.00 g, 3.14 mmol) and potassium carbonate (608 mg, 4.40 mmol) in dimethylformamide (20 mL) was added methyl 3-phenylpropiolate (509 μL, 3.45 mmol) under ice-cooling, and the mixture was stirred at room temperature for 15 hr. The reaction solution was diluted with water and extracted with ethyl acetate. The extract was dried over anhydrous sodium sulfate. The solvent was evaporated under reduced pressure and the residue was purified by silica gel column chromatography (ethyl acetate/hexane=10/90→40/60) to give the title compound (467 mg, yield 51%).

¹H-NMR (CDCl₃) δ: 3.82 (3H, s), 7.23 (1H, dd, J=7.4, 0.8 Hz), 7.42-7.50 (3H, m), 7.67-7.74 (3H, m), 7.75 (1H, d, J=2.2 Hz), 8.41 (1H, d, J=7.4 Hz),

MS (ESI+): 293 (M+H).

Reference Example 11 ethyl 8,9-dihydrofuro[3,2-c]pyrazolo[1,5-a]pyridine-1-carboxylate

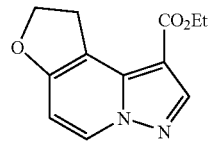

To a mixture of 5-amino-2,3-dihydrofuro[3,2-c]pyridin-5-ium 2,4-dinitrobenzenolate (8.00 g, 25.0 mmol) and potassium carbonate (4.84 g, 35.0 mmol) in dimethylformamide (100 mL) was added ethyl propiolate (2.80 mL, 27.6 mmol) under ice-cooling, and the mixture was stirred at room temperature for 20 hr. The reaction solution was diluted with water and extracted with ethyl acetate. The extract was dried over anhydrous sodium sulfate. The solvent was evaporated under reduced pressure and the residue was purified by silica gel column chromatography (ethyl acetate/hexane=10/90→40/60) to give the title compound (980 mg, yield 17%).

$^1$H-NMR (CDCl$_3$) δ: 1.38 (3H, t, J=7.1 Hz), 3.77 (2H, t, J=9.3 Hz), 4.31 (2H, q, J=7.1 Hz), 4.76 (2H, t, J=9.3 Hz), 6.61 (1H, d, J=7.4 Hz), 8.27-8.32 (2H, m), melting point: 138-139° C. (recrystallized from ethyl acetate),

MS (ESI+): 233 (M+H),

Elemental analysis: for C$_{12}$H$_{12}$N$_2$O$_3$

Calculated (%): C, 62.06; H, 5.21; N, 12.06

Found (%): C, 62.05; H, 5.16; N, 12.12.

Reference Example 12 ethyl 2-ethyl-8,9-dihydrofuro[3,2-c]pyrazolo[1,5-a]pyridine-1-carboxylate

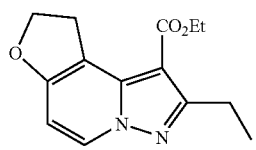

To a mixture of 5-amino-2,3-dihydrofuro[3,2-c]pyridin-5-ium 2,4-dinitrobenzenolate (8.00 g, 25.0 mmol) and potassium carbonate (4.84 g, 35.0 mmol) in dimethylformamide (100 mL) was added ethyl 2-pentynoate (3.63 mL, 27.5 mmol) under ice-cooling, and the mixture was stirred at room temperature for 20 hr. The reaction solution was diluted with water and extracted with ethyl acetate. The extract was dried over anhydrous sodium sulfate. The solvent was evaporated under reduced pressure and the residue was purified by silica gel column chromatography (ethyl acetate/hexane=10/90→40/60) to give the title compound (794 mg, yield 12%).

$^1$H-NMR (CDCl$_3$) δ: 1.33 (3H, t, J=7.4 Hz), 1.39 (3H, t, J=7.2 Hz), 3.05 (2H, q, J=7.4 Hz), 3.73 (2H, t, J=9.1 Hz), 4.32 (2H, q, J=7.2 Hz), 4.72 (2H, t, J=9.1 Hz), 6.54 (1H, d, J=7.1 Hz), 8.19-8.23 (1H, m), melting point: 110-111° C. (recrystallized from ethyl acetate),

MS (ESI+): 261 (M+H),

Elemental analysis: for C$_{14}$H$_{16}$N$_2$O$_3$

Calculated (%): C, 64.60; H, 6.20; N, 10.76

Found (%): C, 64.41; H, 6.11; N, 10.91.

Reference Example 13 methyl 2-phenyl-8,9-dihydrofuro[3,2-c]pyrazolo[1,5-a]pyridine-1-carboxylate

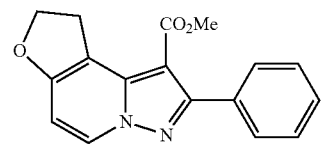

To a mixture of 5-amino-2,3-dihydrofuro[3,2-c]pyridin-5-ium 2,4-dinitrobenzenolate (1.00 g, 3.12 mmol) and potassium carbonate (640 mg, 4.37 mmol) in dimethylformamide (20 mL) was added methyl 3-phenylpropiolate (506 μL, 3.43 mmol) under ice-cooling, and the mixture was stirred at room temperature for 14 hr. The reaction solution was diluted with water and extracted with ethyl acetate. The extract was dried over anhydrous sodium sulfate. The solvent was evaporated under reduced pressure and the residue was purified by silica gel column chromatography (ethyl acetate/hexane=30/70→40/60) to give the title compound (166 mg, yield 18%).

$^1$H-NMR (CDCl$_3$) δ: 3.71 (3H, s), 3.75 (2H, t, J=9.4 Hz), 4.77 (2H, t, J=9.4 Hz), 6.64 (1H, d, J=7.1 Hz), 7.40-7.46 (3H, m), 7.64-7.69 (2H, m), 8.32 (1H, d, J=7.1 Hz).

Reference Example 14 ethyl 2-methyl-8,9-dihydrofuro[3,2-c]pyrazolo[1,5-a]pyridine-1-carboxylate

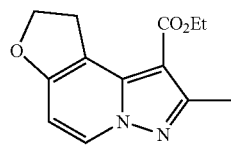

In the same manner as in Reference Example 12, the title compound was obtained (yield 12%) from 5-amino-2,3-dihydrofuro[3,2-c]pyridin-5-ium 2,4-dinitrobenzenolate and ethyl 2-butynoate.

$^1$H-NMR (CDCl$_3$) δ: 1.39 (3H, t, J=7.2 Hz), 2.60 (3H, s), 3.73 (2H, t, J=9.2 Hz), 4.32 (2H, q, J=7.2 Hz), 4.72 (2H, t, J=9.2 Hz), 6.54 (1H, d, J=7.4 Hz), 8.16-8.21 (1H, m), melting point: 132-133° C. (recrystallized from ethyl acetate), MS (ESI+): 247 (M+H), Elemental analysis: for C$_{13}$H$_{14}$N$_2$O$_3$ Calculated (%): C, 63.40; H, 5.73; N, 11.38

Found (%): C, 63.44; H, 5.70; N, 11.48.

Reference Example 15 methyl 2-cyclopropyl-8,9-dihydrofuro[3,2-c]pyrazolo[1,5-a]pyridine-1-carboxylate

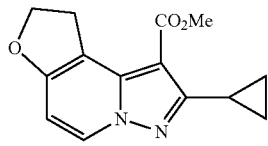

In the same manner as in Reference Example 12, the title compound was obtained (yield 12%) from 5-amino-2,3-dihydrofuro[3,2-c]pyridin-5-ium 2,4-dinitrobenzenolate and methyl 3-cyclopropylprop-2-ynoate.

$^1$H-NMR (CDCl$_3$) δ: 1.00-1.06 (4H, m), 2.71-2.82 (1H, m), 3.70 (2H, t, J=9.2 Hz), 3.85 (3H, s), 4.71 (2H, t, J=9.2 Hz), 6.51 (1H, d, J=7.1 Hz), 8.10-8.15 (1H, m), melting point: 171-172° C. (recrystallized from ethyl acetate),

MS (ESI+): 259 (M+H),

Elemental analysis: for C$_{14}$H$_{14}$N$_2$O$_3$

Calculated (%): C, 65.11; H, 5.46; N, 10.85

Found (%): C, 65.09; H, 5.44; N, 10.93.

Reference Example 16 ethyl 2-(trifluoromethyl)-8,9-dihydrofuro[3,2-c]pyrazolo[1,5-a]pyridine-1-carboxylate

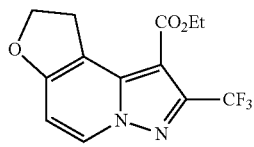

In the same manner as in Reference Example 12, the title compound was obtained (yield 38%) from 5-amino-2,3-dihydrofuro[3,2-c]pyridin-5-ium 2,4-dinitrobenzenolate and ethyl 4,4,4-trifluoro-2-butynoate.

$^1$H-NMR (CDCl$_3$) δ: 1.39 (3H, t, J=7.2 Hz), 3.78 (2H, t, J=9.3 Hz), 4.35 (2H, q, J=7.2 Hz), 4.78 (2H, t, J=9.3 Hz), 6.74 (1H, d, J=7.5 Hz), 8.33 (1H, d, J=7.5 Hz), melting point: 162-163° C. (recrystallized from ethyl acetate/hexane),

MS (ESI+): 301 (M+H),

Elemental analysis: for C$_{13}$H$_{11}$N$_2$O$_3$F$_3$

Calculated (%): C, 52.01; H, 3.69; N, 9.33

Found (%): C, 51.95; H, 3.53; N, 9.39.

Reference Example 17 methyl 2-(4-fluorophenyl)-8,9-dihydrofuro[3,2-c]pyrazolo[1,5-a]pyridine-1-carboxylate

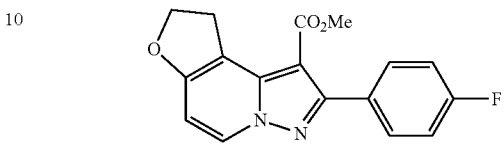

In the same manner as in Reference Example 13, the title compound was obtained (yield 17%) from 5-amino-2,3-dihydrofuro[3,2-c]pyridin-5-ium 2,4-dinitrobenzenolate and methyl 3-(4-fluorophenyl)prop-2-ynoate.

$^1$H-NMR (CDCl$_3$) δ: 3.74 (2H, t, J=9.1 Hz), 3.73 (3H, s), 4.77 (2H, t, J=9.1 Hz), 6.65 (1H, d, J=7.4 Hz), 7.09-7.17 (2H, m), 7.64-7.71 (2H, m), 8.30-8.33 (1H, m).

Reference Example 18 furo[3,2-c]pyrazolo[1,5-a]pyridin-1-ylmethanol

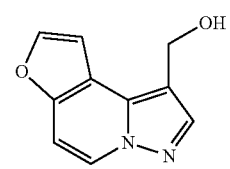

To a suspension of 80% lithium aluminum hydride (250 mg, 5.40 mmol) in tetrahydrofuran (10 mL) was added a solution of ethyl furo[3,2-c]pyrazolo[1,5-a]pyridine-1-carboxylate (310 mg, 1.35 mmol) in tetrahydrofuran (10 mL) at room temperature, and the mixture was stirred at 50° C. for 5 min. Sodium sulfate decahydrate (4.3 g) was added under ice-cooling, and the insoluble material was filtered off. The filtrate was concentrated under reduced pressure, and the residue was purified by silica gel column chromatography (ethyl acetate) and further washed with diisopropyl ether to give the title compound (125 mg, yield 49%).

$^1$H-NMR (CDCl$_3$) δ: 1.68 (1H, t, J=4.9 Hz), 4.96 (2H, d, J=4.9 Hz), 7.03 (1H, d, J=7.7 Hz), 7.16 (1H, d, J=1.9 Hz), 7.71 (1H, d, J=1.9 Hz), 7.92 (1H, s), 8.30 (1H, d, J=7.7 Hz).

Reference Example 19

(2-phenylfuro[3,2-c]pyrazolo[1,5-a]pyridin-1-yl)methanol

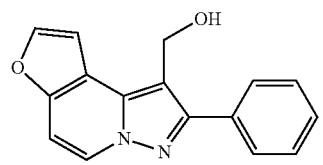

To a suspension of 80% lithium aluminum hydride (294 mg, 6.35 mmol) in tetrahydrofuran (10 mL) was added a solution of methyl 2-phenylfuro[3,2-c]pyrazolo[1,5-a]pyridine-1-carboxylate (465 mg, 1.59 mmol) in tetrahydrofuran (10 mL) at room temperature, and the mixture was stirred at 50° C. for 5 min. Sodium sulfate decahydrate (4.3 g) was added under ice-cooling, and the insoluble material was filtered off. The filtrate was concentrated under reduced pressure and the residue was purified by recrystallization (ethyl acetate) to give the title compound (367 mg, yield 87%).

$^1$H-NMR (CDCl$_3$) δ: 1.66 (1H, t, J=4.9 Hz), 5.05 (2H, d, J=4.9 Hz), 7.06 (1H, dd, J=7.7, 1.0 Hz), 7.21 (1H, dd, J=2.2, 1.0 Hz), 7.39-7.53 (3H, m), 7.74 (1H, d, J=2.2 Hz), 7.82-7.87 (2H, m), 8.35 (1H, d, J=7.7 Hz),

MS (ESI+): 265 (M+H).

Reference Example 20

8,9-dihydrofuro[3,2-c]pyrazolo[1,5-a]pyridin-1-yl-methanol

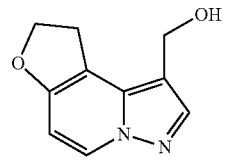

To a suspension of 80% lithium aluminum hydride (760 mg, 16.4 mmol) in tetrahydrofuran (40 mL) was added a solution of ethyl 8,9-dihydrofuro[3,2-c]pyrazolo[1,5-a]pyridine-1-carboxylate (950 mg, 4.09 mmol) in tetrahydrofuran (40 mL) under ice-cooling, and the mixture was stirred at room temperature for 30 min. Sodium sulfate decahydrate (10 g) was added under ice-cooling, and the insoluble material was filtered off. The filtrate was concentrated under reduced pressure, and the residue was washed with diisopropyl ether to give the title compound (650 mg, yield 83%).

$^1$H-NMR (CDCl$_3$) δ: 1.42 (1H, t, J=5.5 Hz), 3.53 (2H, t, J=9.1 Hz), 4.72-4.82 (4H, m), 6.52 (1H, d, J=7.4 Hz), 7.87 (1H, s), 8.23-8.29 (1H, m), melting point: 152-154° C. (recrystallized from ethanol/diisopropyl ether), Elemental analysis: for C$_{10}$H$_{10}$N$_2$O$_2$
Calculated (%): C, 63.15; H, 5.30; N, 14.73
Found (%): C, 63.04; H, 5.27; N, 14.79.

Reference Example 21

(2-ethyl-8,9-dihydrofuro[3,2-c]pyrazolo[1,5-a]pyridin-1-yl)methanol

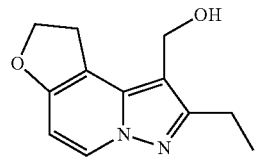

To a suspension of 80% lithium aluminum hydride (548 mg, 11.8 mmol) in tetrahydrofuran (30 mL) was added a solution of ethyl 2-ethyl-8,9-dihydrofuro[3,2-c]pyrazolo[1,5-a]pyridine-1-carboxylate (770 mg, 2.96 mmol) in tetrahydrofuran (30 mL) under ice-cooling, and the mixture was stirred at room temperature for 30 min. Sodium sulfate decahydrate (10 g) was added under ice-cooling, and the insoluble material was filtered off. The filtrate was concentrated under reduced pressure, and the residue was washed with diisopropyl ether to give the title compound (485 mg, yield 75%).

$^1$H-NMR (CDCl$_3$) δ: 1.35 (3H, t, J=7.7 Hz), 2.83 (2H, q, J=7.7 Hz), 3.48 (2H, t, J=9.1 Hz), 4.70-4.79 (4H, m), 6.42 (1H, d, J=7.4 Hz), 8.17 (1H, d, J=7.4 Hz), hidden (1H), melting point: 119-120° C. (recrystallized from ethyl acetate/diisopropyl ether), Elemental analysis: for C$_{11}$H$_{14}$N$_2$O$_2$.0.1H$_2$O
Calculated (%): C, 65.50; H, 6.50; N, 12.73
Found (%): C, 65.28; H, 6.40; N, 12.73.

Reference Example 22

(2-phenyl-8,9-dihydrofuro[3,2-c]pyrazolo[1,5-a]pyridin-1-yl)methanol

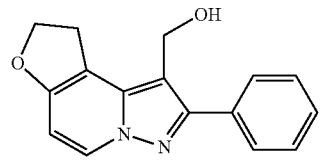

To a suspension of 80% lithium aluminum hydride (100 mg, 2.16 mmol) in tetrahydrofuran (5 mL) was added a solution of methyl 2-phenyl-8,9-dihydrofuro[3,2-c]pyrazolo[1,5-a]pyridine-1-carboxylate (160 mg, 0.544 mmol) in tetrahydrofuran (5 mL) at room temperature, and the mixture was stirred for 30 min. Sodium sulfate decahydrate (1.7 g) was added under ice-cooling, and the insoluble material was filtered off. The filtrate was concentrated under reduced pressure, purified by silica gel column chromatography (ethyl acetate), and further washed with diisopropyl ether to give the title compound (132 mg, yield 90%).

$^1$H-NMR (CDCl$_3$) δ: 1.66 (1H, s), 3.54 (2H, t, J=9.1 Hz), 4.77 (2H, t, J=9.1 Hz), 4.83 (2H, s), 6.51 (1H, d, J=7.4 Hz), 7.37-7.52 (3H, m), 7.78-7.85 (2H, m), 8.24-8.29 (1H, m).

MS (ESI+): 267 (M+H).

Reference Example 23

(2-methyl-8,9-dihydrofuro[3,2-c]pyrazolo[1,5-a]pyridin-1-yl)methanol

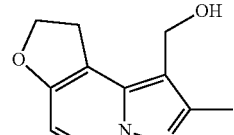

In the same manner as in Reference Example 21, the title compound was obtained (yield 92%) from ethyl 2-methyl-8,9-dihydrofuro[3,2-c]pyrazolo[1,5-a]pyridine-1-carboxylate.

$^1$H-NMR (CDCl$_3$) δ: 1.29 (1H, t, J=5.1 Hz), 2.45 (3H, s), 3.48 (2H, t, J=9.1 Hz), 4.68-4.81 (4H, m), 6.42 (1H, d, J=7.4 Hz), 8.11-8.17 (1H, m), melting point: 173-174° C. (recrystallized from ethanol/diisopropyl ether), Elemental analysis: for $C_{11}H_{12}N_2O_2$ Calculated (%): C, 64.69; H, 5.92; N, 13.72

Found (%): C, 64.69; H, 5.92; N, 13.77.

Reference Example 24

(2-cyclopropyl-8,9-dihydrofuro[3,2-c]pyrazolo[1,5-a]pyridin-1-yl)methanol

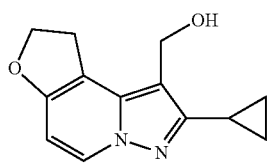

In the same manner as in Reference Example 21, the title compound was obtained (yield 93%) from methyl 2-cyclopropyl-8,9-dihydrofuro[3,2-c]pyrazolo[1,5-a]pyridine-1-carboxylate.

$^1$H-NMR (CDCl$_3$) δ: 0.96-1.06 (4H, m), 1.43 (1H, brs), 1.99-2.12 (1H, m), 3.47 (2H, t, J=9.1 Hz), 4.73 (2H, t, J=9.1 Hz), 4.81 (2H, s), 6.38 (1H, d, J=7.4 Hz), 8.06-8.13 (1H, m), melting point: 170-172° C. (recrystallized from ethyl acetate), Elemental analysis: for $C_{13}H_{14}N_2O_2 \cdot 0.1H_2O$ Calculated (%): C, 67.28; H, 6.17; N, 12.07

Found (%): C, 67.47; H, 6.14; N, 12.17.

Reference Example 25

[2-(trifluoromethyl)-8,9-dihydrofuro[3,2-c]pyrazolo[1,5-a]pyridin-1-yl]methanol

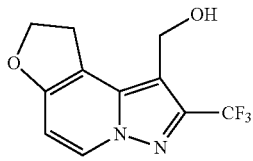

In the same manner as in Reference Example 21, the title compound was obtained (yield 49%) from ethyl 2-(trifluoromethyl)-8,9-dihydrofuro[3,2-c]pyrazolo[1,5-a]pyridine-1-carboxylate.

$^1$H-NMR (CDCl$_3$) δ: 3.56 (2H, t, J=9.2 Hz), 4.73-4.89 (4H, m), 6.65 (1H, d, J=7.4 Hz), 8.27 (1H, d, J=7.4 Hz), hidden (1H), melting point: 144-145° C. (recrystallized from ethanol/hexane),

MS (ESI+): 259 (M+H),

Elemental analysis: for $C_{11}H_9N_2O_2F_3$

Calculated (%): C, 51.17; H, 3.51; N, 10.85

Found (%): C, 51.18; H, 3.40; N, 10.92.

Reference Example 26

[2-(4-fluorophenyl)-8,9-dihydrofuro[3,2-c]pyrazolo[1,5-a]pyridin-1-yl]methanol

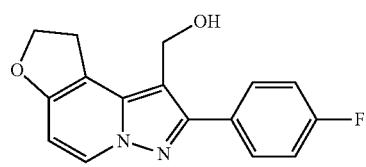

In the same manner as in Reference Example 22, the title compound was obtained (yield 85%) from methyl 2-(4-fluorophenyl)-8,9-dihydrofuro[3,2-c]pyrazolo[1,5-a]pyridine-1-carboxylate.

$^1$H-NMR (CDCl$_3$) δ: 3.53 (2H, t, J=9.1 Hz), 4.73-4.81 (4H, m), 6.51 (1H, d, J=7.1), 7.11-7.20 (2H, m), 7.78-7.86 (2H, m), 8.23-8.27 (1H, m), hidden (1H),

MS (ESI+): 285 (M+H).

Reference Example 27 furo[3,2-c]pyrazolo[1,5-a]pyridin-1-ylacetonitrile

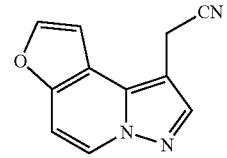

To a solution of boron trifluoride diethyl ether complex (200 μL, 1.58 mmol) and trimethylsilyl cyanide (280 μL, 2.10 mmol) in dichloromethane (5 mL) was added a solution of furo[3,2-c]pyrazolo[1,5-a]pyridin-1-ylmethanol (100 mg, 0.531 mmol) in dichloromethane (5 mL) under ice-cooling and an argon atmosphere, and the mixture was stirred for 30 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=10/90→30/70) to give the title compound (57.1 mg, yield 55%).

$^1$H-NMR (CDCl$_3$) δ: 3.96 (2H, s), 7.08 (1H, dd, J=7.4, 0.8 Hz), 7.11 (1H, dd, J=2.2, 0.8 Hz), 7.75 (1H, d, J=2.2 Hz), 7.92 (1H, s), 8.33 (1H, d, J=7.4 Hz),

MS (ESI+): 198 (M+H).

Reference Example 28

(2-phenylfuro[3,2-c]pyrazolo[1,5-a]pyridin-1-yl)acetonitrile

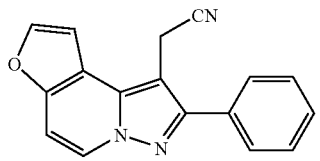

To a solution of boron trifluoride diethyl ether complex (460 μL, 3.63 mmol) and trimethylsilyl cyanide (645 μL, 4.84 mmol) in dichloromethane (12 mL) was added a solution of (2-phenylfuro[3,2-c]pyrazolo[1,5-a]pyridin-1-yl)methanol (320 mg, 1.21 mmol) in dichloromethane (12 mL) under ice-cooling and an argon atmosphere, and the mixture was stirred for 2 hr. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=10/90→50/50) to give the title compound (240 mg, yield 73%).

$^1$H-NMR (CDCl$_3$) δ: 4.01 (2H, s), 7.13 (1H, dd, J=7.4, 0.8 Hz), 7.22 (1H, dd, J=2.2, 0.8 Hz), 7.44-7.57 (3H, m), 7.65-7.70 (2H, m), 7.80 (1H, d, J=2.2 Hz), 8.37 (1H, d, J=7.4 Hz).

Reference Example 29

8,9-dihydrofuro[3,2-c]pyrazolo[1,5-a]pyridin-1-ylacetonitrile

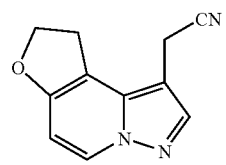

To a solution of boron trifluoride diethyl ether complex (1.26 mL, 9.94 mmol) and trimethylsilyl cyanide (1.77 mL, 13.3 mmol) in dichloromethane (13 mL) was added a solution of 8,9-dihydrofuro[3,2-c]pyrazolo[1,5-a]pyridin-1-ylmethanol (630 mg, 3.31 mmol) in dichloromethane (39 mL) under ice-cooling and an argon atmosphere, and the mixture was stirred at room temperature for 30 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=10/90→40/60) to give the title compound (274 mg, yield 42%).

$^1$H-NMR (CDCl$_3$) δ: 3.58 (2H, t, J=9.1 Hz), 3.81 (2H, s), 4.78 (2H, t, J=9.1 Hz), 6.53 (1H, d, J=7.4 Hz), 7.81 (1H, s), 8.20-8.28 (1H, m), melting point: 165-166° C. (recrystallized from ethyl acetate/hexane), MS (ESI+): 200 (M+H),
Elemental analysis: for C$_{11}$H$_9$N$_3$O
Calculated (%): C, 66.32; H, 4.55; N, 21.09
Found (%): C, 66.28; H, 4.48; N, 21.11.

Reference Example 30

(2-ethyl-8,9-dihydrofuro[3,2-c]pyrazolo[1,5-a]pyridin-1-yl)acetonitrile

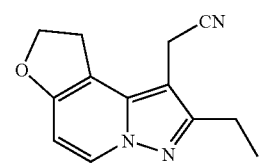

To a solution of boron trifluoride diethyl ether complex (836 μL, 6.60 mmol) and trimethylsilyl cyanide (1.17 mL, 8.77 mmol) in dichloromethane (5 mL) was added a solution of (2-ethyl-8,9-dihydrofuro[3,2-c]pyrazolo[1,5-a]pyridin-1-yl)methanol (480 mg, 2.20 mmol) in dichloromethane (10 mL) under ice-cooling and an argon atmosphere, and the mixture was stirred at room temperature for 30 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=10/90→30/70) to give the title compound (296 mg, yield 59%).

$^1$H-NMR (CDCl$_3$) δ: 1.35 (3H, t, J=7.7 Hz), 2.80 (2H, q, J=7.7 Hz), 3.56 (2H, t, J=9.1 Hz), 3.73 (2H, s), 4.76 (2H, t, J=9.1 Hz), 6.44 (1H, d, J=7.4 Hz), 8.14-8.19 (1H, m), melting point: 179-180° C. (recrystallized from ethyl acetate/hexane), MS (ESI+): 228 (M+H),
Elemental analysis: for C$_{13}$H$_{13}$N$_3$O
Calculated (%): C, 68.70; H, 5.77; N, 18.49
Found (%): C, 68.84; H, 5.74; N, 18.61.

Reference Example 31

(2-phenyl-8,9-dihydrofuro[3,2-c]pyrazolo[1,5-a]pyridin-1-yl)acetonitrile

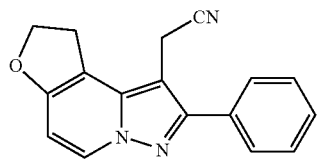

To a solution of boron trifluoride diethyl ether complex (186 μL, 1.47 mmol) and trimethylsilyl cyanide (260 μL, 1.95 mmol) in dichloromethane (5 mL) was added a solution of (2-phenyl-8,9-dihydrofuro[3,2-c]pyrazolo[1,5-a]pyridin-1-yl)methanol (130 mg, 0.488 mmol) in dichloromethane (10 mL) under ice-cooling and an argon atmosphere, and the mixture was stirred at room temperature for 1 hr. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=10/90→40/60) to give the title compound (117 mg, yield 87%).

$^1$H-NMR (CDCl$_3$) δ: 3.67 (2H, t, J=9.1 Hz), 3.85 (2H, s), 4.82 (2H, t, J=9.1 Hz), 6.55 (1H, d, J=7.4 Hz), 7.42-7.54 (3H, m), 7.62-7.67 (2H, m), 8.26-8.30 (1H, m),

MS (ESI+): 276 (M+H).

Reference Example 32

(2-methyl-8,9-dihydrofuro[3,2-c]pyrazolo[1,5-a]pyridin-1-yl)acetonitrile

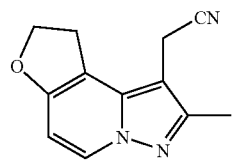

In the same manner as in Reference Example 30, the title compound was obtained (yield 46%) from (2-methyl-8,9-dihydrofuro[3,2-c]pyrazolo[1,5-a]pyridin-1-yl)methanol.

$^1$H-NMR (CDCl$_3$) δ: 2.43 (3H, s), 3.55 (2H, t, J=9.1 Hz), 3.72 (2H, s), 4.77 (2H, t, J=9.1 Hz), 6.44 (1H, d, J=7.4 Hz), 8.12-8.17 (1H, m), melting point: 173-174° C. (recrystallized from ethyl acetate/hexane),

MS (ESI+): 214 (M+H),

Elemental analysis: for C$_{12}$H$_{11}$N$_3$O

Calculated (%): C, 67.59; H, 5.20; N, 19.71

Found (%): C, 67.80; H, 5.17; N, 19.75.

Reference Example 33

(2-cyclopropyl-8,9-dihydrofuro[3,2-c]pyrazolo[1,5-a]pyridin-1-yl)acetonitrile

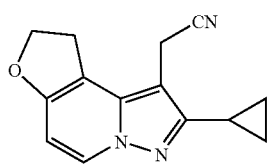

In the same manner as in Reference Example 30, the title compound was obtained (yield 55%) from (2-cyclopropyl-8,9-dihydrofuro[3,2-c]pyrazolo[1,5-a]pyridin-1-yl)methanol.

$^1$H-NMR (CDCl$_3$) δ: 0.95-1.08 (4H, m), 1.85-1.97 (1H, m), 3.55 (2H, t, J=9.1 Hz), 3.83 (2H, s), 4.76 (2H, t, J=9.1 Hz), 6.41 (1H, d, J=7.4 Hz), 8.08-8.13 (1H, m), melting point: 139-140° C. (recrystallized from ethyl acetate/hexane),

MS (ESI+): 240 (M+H),

Elemental analysis: for C$_{14}$H$_{13}$N$_3$O

Calculated (%): C, 70.28; H, 5.48; N, 17.56

Found (%): C, 70.37; H, 5.46; N, 17.66.

Reference Example 34

[2-(trifluoromethyl)-8,9-dihydrofuro[3,2-c]pyrazolo[1,5-a]pyridin-1-yl]acetonitrile

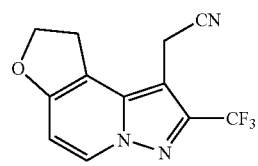

In the same manner as in Reference Example 30, the title compound was obtained (yield 96%) from [2-(trifluoromethyl)-8,9-dihydrofuro[3,2-c]pyrazolo[1,5-a]pyridin-1-yl]methanol.

$^1$H-NMR (CDCl$_3$) δ: 3.66 (2H, t, J=9.3 Hz), 3.89 (2H, s), 4.84 (2H, t, J=9.3 Hz), 6.70 (1H, d, J=7.6 Hz), 8.29 (1H, d, J=7.6 Hz), melting point: 151-153° C. (recrystallized from ethyl acetate/hexane),

MS (ESI+): 268 (M+H),

Elemental analysis: for C$_{12}$H$_8$N$_3$OF$_3$

Calculated (%): C, 53.94; H, 3.02; N, 15.73

Found (%): C, 53.45; H, 2.92; N, 15.66.

Reference Example 35

[2-(4-fluorophenyl)-8,9-dihydrofuro[3,2-c]pyrazolo[1,5-a]pyridin-1-yl]acetonitrile

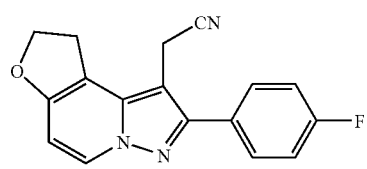

In the same manner as in Reference Example 31, the title compound was obtained (yield 89%) from [2-(4-fluorophenyl)-8,9-dihydrofuro[3,2-c]pyrazolo[1,5-a]pyridin-1-yl]methanol.

$^1$H-NMR (CDCl$_3$) δ: 3.65 (2H, t, J=9.2 Hz), 3.82 (2H, s), 4.82 (2H, t, J=9.2 Hz), 6.56 (1H, d, J=7.4 Hz), 7.16-7.24 (2H, m), 7.59-7.67 (2H, m), 8.25-8.29 (1H, m), melting point: 189-190° C. (recrystallized from ethyl acetate/hexane),

MS (ESI+): 294 (M+H),

Elemental analysis: for C$_{17}$H$_{12}$N$_3$OF

Calculated (%): C, 69.62; H, 4.12; N, 14.33

Found (%): C, 69.61; H, 4.04; N, 14.48.

Reference Example 36

2-furo[3,2-c]pyrazolo[1,5-a]pyridin-1-ylethanamine

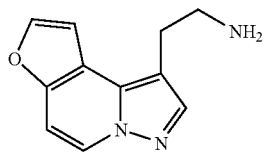

Furo[3,2-c]pyrazolo[1,5-a]pyridin-1-ylacetonitrile (55.0 mg, 0.279 mmol) and Raney cobalt (500 mg) were suspended in 2M ammonia/methanol solution (10 mL), and the suspension was stirred at room temperature for 3 hr under a hydrogen atmosphere. The catalyst was filtered through celite, and the filtrate was concentrated under reduced pressure to give the title compound (55.5 mg, yield 99%).
MS (ESI+): 202 (M+H).

Reference Example 37

2-(2-phenylfuro[3,2-c]pyrazolo[1,5-a]pyridin-1-yl) ethanamine hydrochloride

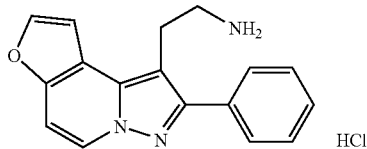

A mixture of (2-phenylfuro[3,2-c]pyrazolo[1,5-a]pyridin-1-yl)acetonitrile (150 mg, 0.549 mmol), Raney cobalt (1.5 g) and 2M ammonia/methanol solution (5 mL) in methanol (15 mL) was stirred at 40° C. for 5 hr under a hydrogen atmosphere. The catalyst was filtered through celite, and the filtrate was concentrated under reduced pressure. The residue was dissolved in methanol, 4M hydrochloric acid (ethyl acetate solution, 280 μL) was added, and the solvent was evaporated under reduced pressure. The residue was washed with ethyl acetate to give the title compound (129 mg, yield 75%).
$^1$H-NMR (DMSO-d$_6$) δ: 2.87-3.06 (2H, m), 3.28-3.41 (2H, m), 7.35 (1H, d, J=7.4 Hz), 7.43-7.58 (3H, m), 7.75-7.82 (3H, m), 8.09-8.34 (4H, m), 8.60 (1H, d, J=7.4 Hz).

Reference Example 38

2-(8,9-dihydrofuro[3,2-c]pyrazolo[1,5-a]pyridin-1-yl)ethanamine

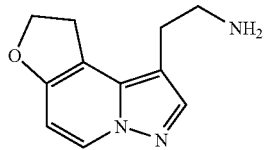

8,9-Dihydrofuro[3,2-c]pyrazolo[1,5-a]pyridin-1-ylacetonitrile (250 mg, 1.25 mmol) and Raney cobalt (2.5 g) were suspended in 2M ammonia/methanol solution (50 mL), and the suspension was stirred at room temperature for 12 hr under a hydrogen atmosphere. The catalyst was filtered through celite, and the filtrate was concentrated under reduced pressure to give the title compound (238 mg, yield 94%).
$^1$H-NMR (METHANOL-d$_4$) δ: 2.85 (2H, brs), 3.30-3.39 (2H, m), 3.43-3.59 (2H, m), 4.66-4.79 (2H, m), 6.48-6.60 (1H, m), 7.68-7.78 (1H, m), 8.21-8.24 (1H, m), hidden (2H),
MS (ESI+): 204 (M+H).

Reference Example 39

2-(2-ethyl-8,9-dihydrofuro[3,2-c]pyrazolo[1,5-a]pyridin-1-yl)ethanamine

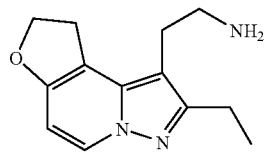

(2-Ethyl-8,9-dihydrofuro[3,2-c]pyrazolo[1,5-a]pyridin-1-yl)acetonitrile (120 mg, 0.528 mmol) and Raney cobalt (1.2 g) were suspended in 2M ammonia/methanol solution (25 mL), and the suspension was stirred at room temperature for 12 hr under a hydrogen atmosphere. The catalyst was filtered through celite, and the filtrate was concentrated under reduced pressure to give the title compound (120 mg, yield 98%).
$^1$H-NMR (METHANOL-d$_4$) δ: 1.30 (3H, t, J=7.6 Hz), 2.72-2.85 (6H, m), 3.47 (2H, t, J=9.1 Hz), 4.71 (2H, t, J=9.1 Hz), 6.46 (1H, d, J=7.4 Hz), 8.15 (1H, d, J=7.4 Hz), hidden (2H),
MS (ESI+): 232 (M+H).

Reference Example 40

2-(2-phenyl-8,9-dihydrofuro[3,2-c]pyrazolo[1,5-a]pyridin-1-yl)ethanamine hydrochloride

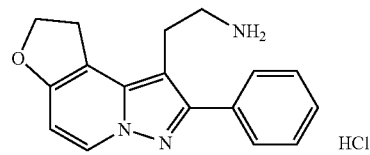

(2-Phenyl-8,9-dihydrofuro[3,2-c]pyrazolo[1,5-a]pyridin-1-yl)acetonitrile (115 mg, 0.418 mmol) and Raney cobalt (1.2 g) were suspended in 2M ammonia/methanol solution (20 mL), and the mixture was stirred at 40° C. overnight under a hydrogen atmosphere. The catalyst was filtered through celite, and the filtrate was concentrated under reduced pressure. The residue was dissolved in methanol, 4M hydrochloric acid (ethyl acetate solution, 420 μL) was added, and the solvent was evaporated under reduced pressure. The residue was washed with ethyl acetate to give the title compound (107 mg, yield 81%).

¹H-NMR (DMSO-d₆) δ: 2.80-2.92 (2H, m), 3.12-3.23 (2H, m), 3.58 (2H, t, J=9.1 Hz), 4.76 (2H, t, J=9.1 Hz), 6.67 (1H, d, J=7.2 Hz), 7.40-7.55 (3H, m), 7.73-7.80 (2H, m), 8.23 (3H, brs), 8.50 (1H, d, J=7.2 Hz),
MS (ESI+): 280 (M+H).

Reference Example 41

2-(2-methyl-8,9-dihydrofuro[3,2-c]pyrazolo[1,5-a]pyridin-1-yl)ethanamine

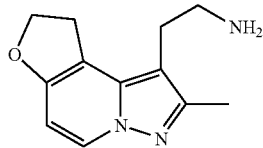

In the same manner as in Reference Example 39, the title compound was obtained (yield 95%) from (2-methyl-8,9-dihydrofuro[3,2-c]pyrazolo[1,5-a]pyridin-1-yl)acetonitrile.
¹H-NMR (METHANOL-d₄) δ: 2.35 (2H, brs), 2.79 (3H, brs), 3.23-3.53 (4H, m), 4.62-4.77 (2H, m), 6.40-6.51 (1H, m), 8.03-8.18 (1H, m), hidden (2H),
MS (ESI+): 218 (M+H).

Reference Example 42

2-(2-cyclopropyl-8,9-dihydrofuro[3,2-c]pyrazolo[1,5-a]pyridin-1-yl)ethanamine

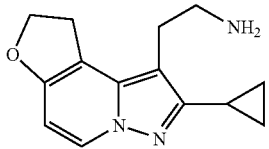

In the same manner as in Reference Example 39, the title compound was obtained (yield 97%) from (2-cyclopropyl-8,9-dihydrofuro[3,2-c]pyrazolo[1,5-a]pyridin-1-yl)acetonitrile.
¹H-NMR (METHANOL-d₄) δ: 0.87-1.06 (4H, m), 1.95-2.10 (1H, m), 2.76-2.98 (4H, m), 3.46 (2H, t, J=9.1 Hz), 4.70 (2H, t, J=9.1 Hz), 6.42 (1H, d, J=7.4 Hz), 8.08 (1H, d, J=7.4 Hz), hidden (2H),
MS (ESI+): 244 (M+H).

Reference Example 43

2-[2-(trifluoromethyl)-8,9-dihydrofuro[3,2-c]pyrazolo[1,5-a]pyridin-1-yl]ethanamine

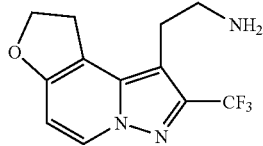

In the same manner as in Reference Example 39, the title compound was obtained (yield 95%) from [2-(trifluoromethyl)-8,9-dihydrofuro[3,2-c]pyrazolo[1,5-a]pyridin-1-yl]acetonitrile.
¹H-NMR (CDCl₃) δ: 2.92 (4H, s), 3.54 (2H, t, J=9.3 Hz), 4.78 (2H, t, J=9.3 Hz), 6.61 (1H, d, J=7.6 Hz), 8.25 (1H, d, J=7.6 Hz), hidden (2H),
melting point: 118-119° C. (recrystallized from ethyl acetate/hexane),
MS (ESI+): 272 (M+H),
Elemental analysis: for $C_{12}H_{12}N_3OF_3 \cdot 0.3H_2O$
Calculated (%): C, 52.10; H, 4.58; N, 15.19
Found (%): C, 52.19; H, 4.42; N, 14.92.

Reference Example 44

2-[2-(4-fluorophenyl)-8,9-dihydrofuro[3,2-c]pyrazolo[1,5-a]pyridin-1-yl]ethanamine hydrochloride

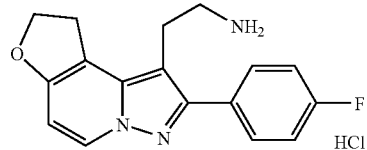

In the same manner as in Reference Example 40, the title compound was obtained (yield 100%) from [2-(4-fluorophenyl)-8,9-dihydrofuro[3,2-c]pyrazolo[1,5-a]pyridin-1-yl]acetonitrile.
¹H-NMR (DMSO-d₆) δ: 2.76-2.92 (2H, m), 3.09-3.18 (2H, m), 3.56 (2H, t, J=9.2 Hz), 4.76 (2H, t, J=9.2 Hz), 6.68 (1H, d, J=7.4 Hz), 7.28-7.37 (2H, m), 7.75-7.85 (2H, m), 8.10 (3H, brs), 8.50 (1H, d, J=7.4 Hz).

Reference Example 45

(2E)-3-furo[3,2-c]pyridin-4-ylacrylamide

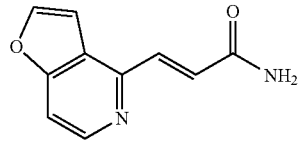

A mixture of 4-chlorofuro[3,2-c]pyridine (1.00 g, 6.51 mmol), acrylamide (694 mg, 9.77 mmol), sodium acetate (641 mg, 7.81 mmol), tetrabutylammonium bromide (2.31 g, 7.16 mmol), tri-o-tolylphosphine (396 mg, 1.30 mmol) and palladium(II) acetate (146 mg, 0.65 mmol) in N,N-dimethylformamide (20 mL) was stirred at 140° C. for 16 hr. The reaction solution was diluted with saturated aqueous sodium hydrogen carbonate solution, and the mixture was extracted with ethyl acetate. The extract was washed with water and saturated brine and dried over anhydrous magnesium sulfate. The solvent was evaporated under reduced pressure and the residue was purified by silica gel column chromatography (methanol/ethyl acetate=0/100→10/90) to give the title compound (508 mg, yield 41%).

¹H-NMR (CDCl₃) δ: 5.84 (2H, brs), 7.06 (1H, s), 7.24 (1H, d, J=15.1 Hz), 7.44 (1H, d, J=5.8 Hz), 7.72 (1H, s), 7.98 (1H, d, J=15.1 Hz), 8.51 (1H, d, J=5.8 Hz).

Reference Example 46

3-(2,3-dihydrofuro[3,2-c]pyridin-4-yl)propanamide

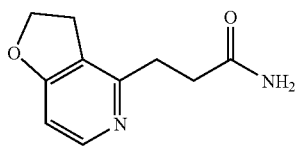

To a solution of (2E)-3-furo[3,2-c]pyridin-4-ylacrylamide (500 mg, 2.65 mmol) in acetic acid (5 mL) was added palladium-carbon powder (10 mg), and the mixture was stirred at room temperature for 14 hr under a hydrogen atmosphere. The catalyst was filtered off, and the filtrate was evaporated under reduced pressure. The residue was purified by silica gel column chromatography (NH, methanol/ethyl acetate=3/97→15/85) to give the title compound (211 mg, yield 41%).

¹H-NMR (METHANOL-d₄) δ: 2.48 (2H, t, J=7.4 Hz), 2.88 (2H, t, J=7.4 Hz), 3.18 (2H, t, J=8.9 Hz), 4.66 (2H, t, J=8.9 Hz), 6.81 (1H, d, J=6.6 Hz), 8.08 (1H, d, J=6.6 Hz), hidden (2H).

Reference Example 47

3-(2,3-dihydrofuro[3,2-c]pyridin-4-yl)propanenitrile

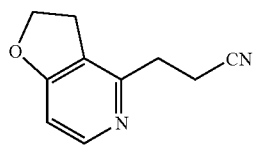

To a solution of 3-(2,3-dihydrofuro[3,2-c]pyridin-4-yl)propanamide (435 mg, 2.26 mmol) in dichloromethane (10 mL) were added pyridine (384 μL, 4.75 mmol) and trifluoroacetic anhydride (384 μL, 2.72 mmol), and the mixture was stirred at room temperature for 13 min. The reaction solution was diluted with saturated aqueous sodium hydrogen carbonate solution, and the mixture was extracted with dichloromethane. The extract was dried over anhydrous magnesium sulfate. The solvent was evaporated under reduced pressure and the residue was purified by silica gel column chromatography (NH, ethyl acetate/hexane=30/70→70/30) to give the title compound (132 mg, yield 33%).

¹H-NMR (CDCl₃) δ: 2.87 (2H, t, J=7.1 Hz), 3.02 (2H, t, J=7.1 Hz), 3.25 (2H, t, J=8.8 Hz), 4.68 (2H, t, J=8.8 Hz), 6.66 (1H, d, J=5.5 Hz), 8.25 (1H, d, J=5.5 Hz).

Reference Example 48

N-[3-(2,3-dihydrofuro[3,2-c]pyridin-4-yl)propyl]acetamide

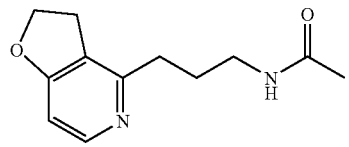

3-(2,3-Dihydrofuro[3,2-c]pyridin-4-yl)propanenitrile (110 mg, 0.63 mmol) and Raney cobalt (200 mg) were suspended in 2M ammonia/ethanol solution (10 mL), and the suspension was stirred at room temperature for 13 hr under a hydrogen atmosphere. The catalyst was filtered through celite, and the filtrate was evaporated under reduced pressure. This was dissolved in dichloromethane (5 mL), triethylamine (173 μL, 1.24 mmol) and acetyl chloride (52.8 μL, 0.743 mmol) were added, and the mixture was stirred at room temperature for 20 min. The reaction solution was diluted with saturated aqueous sodium hydrogen carbonate solution and the mixture was extracted with dichloromethane. The extract was dried over anhydrous magnesium sulfate. The solvent was evaporated under reduced pressure and the residue was purified by silica gel column chromatography (NH, methanol/ethyl acetate=0/100→10/90) to give the title compound (47 mg, yield 35%).

¹H-NMR (CDCl₃) δ: 1.87 (2H, t, J=7.1 Hz), 1.87 (3H, s), 2.69 (2H, t, J=7.1 Hz), 3.11 (2H, t, J=8.8 Hz), 3.16-3.30 (2H, m), 4.58 (2H, t, J=8.8 Hz), 6.53 (1H, s), 6.54 (1H, d, J=5.5 Hz), 8.13 (1H, d, J=5.5 Hz).

Reference Example 49

2-(but-3-yn-1-yloxy)pyrimidine

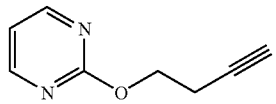

To a solution of but-3-yn-1-ol (4.59 g, 65.5 mmol) in 1,2-dimethoxyethane (120 mL) was added 60% sodium hydride (2.45 g, 61.1 mmol) under ice-cooling, and the mixture was stirred for 1 hr. A solution of 2-chloropyrimidine (5.00 g, 43.7 mmol) in tetrahydrofuran (30 mL) was added thereto, and the mixture was stirred at room temperature for 4 hr. The reaction solution was diluted with water, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane=20/80→60/40) to give the title compound (5.18 g, yield 80%).

¹H-NMR (CDCl₃) δ: 2.02 (1H, t, J=2.7 Hz), 2.73 (2H, dt, J=7.3, 2.7 Hz), 4.48 (2H, t, J=7.3 Hz), 6.94 (1H, t, J=4.7 Hz), 8.50 (2H, d, J=4.7 Hz).

Reference Example 50

2-{[4-(trimethylsilyl)but-3-yn-1-yl]oxy}pyrimidine

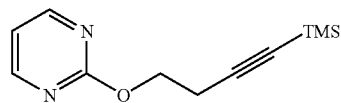

To a solution of diisopropylamine (1.37 g, 13.5 mmol) in tetrahydrofuran (20 mL) was added 1.6M butyllithium/hexane solution (8.44 mL, 13.5 mmol) at −78° C., and the mixture was stirred for 2 hr. A solution of 2-(but-3-yn-1-yloxy)pyrimidine (1.00 g, 6.75 mmol) in tetrahydrofuran (2.5 mL) was added thereto, and the mixture was stirred for 1 hr. Chlorotrimethylsilane (1.80 mL, 14.2 mmol) was added, the reaction solution was diluted with water, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane=10/90→40/60) to give the title compound (1.43 g, yield 91%).

¹H-NMR (CDCl₃) δ: 0.15 (9H, s), 2.77 (2H, t, J=7.4 Hz), 4.48 (2H, t, J=7.4 Hz), 6.94 (1H, t, J=5.0 Hz), 8.51 (2H, d, J=4.9 Hz).

Reference Example 51

4-(trimethylsilyl)-2,3-dihydrofuro[2,3-b]pyridine

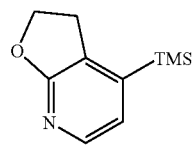

A solution of 2-{[4-(trimethylsilyl)but-3-yn-1-yl]oxy}pyrimidine (116 g, 524 mmol) in nitrobenzene (1000 mL) was stirred at 200° C. for 24 hr. The solvent was removed by silica gel column chromatography (ethyl acetate/hexane=13/87→50/50). The residue was diluted with ethyl acetate, and the mixture was extracted twice with 1M hydrochloric acid. The aqueous layer was neutralized with 8M aqueous sodium hydroxide solution and extracted with ethyl acetate. The solvent was evaporated under reduced pressure to give the title compound (16.2 g, yield 14%).

¹H-NMR (CDCl₃) δ: 0.31 (9H, s), 3.26 (2H, t, J=8.5 Hz), 4.60 (2H, t, J=8.5 Hz), 6.83 (1H, d, J=4.9 Hz), 7.95 (1H, d, J=4.9 Hz).

Reference Example 52

5-bromo-4-(trimethylsilyl)-2,3-dihydrofuro[2,3-b]pyridine

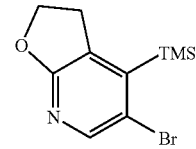

To a solution of 4-(trimethylsilyl)-2,3-dihydrofuro[2,3-b]pyridine (463 mg, 2.40 mmol) in dichloromethane (10 mL) were added sodium hydrogen carbonate (504 mg, 6.00 mmol) and bromine (959 mg, 6.00 mmol) at room temperature, and the mixture was stirred for 9 hr. An aqueous sodium thiosulfate solution was added to the reaction solution, and the mixture was extracted with dichloromethane. The extract was washed with saturated brine and dried over anhydrous sodium sulfate. The solvent was evaporated under reduced pressure and the residue was purified by silica gel column chromatography (ethyl acetate/hexane=5/95→30/70) to give the title compound (522 mg, yield 80%).

¹H-NMR (CDCl₃) δ: 0.44 (9H, s), 3.31 (2H, t, J=8.6 Hz), 4.58 (2H, t, J=8.6 Hz), 8.03 (1H, s), melting point: 92-94° C. (recrystallized from hexane), Elemental analysis: for $C_{10}H_{14}NOBrSi \cdot 0.1H_2O$ Calculated (%): C, 43.54; H, 5.25; N, 5.07

Found (%): C, 43.34; H, 5.20; N, 5.05.

Reference Example 53

5-allyl-4-(trimethylsilyl)-2,3-dihydrofuro[2,3-b]pyridine

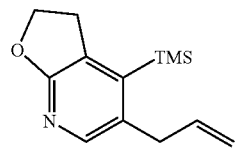

A mixture of 5-bromo-4-(trimethylsilyl)-2,3-dihydrofuro[2,3-b]pyridine (37.5 g, 138 mmol), allyltributyltin (65.8 mL, 212 mmol) and trans-dichlorobis(triphenylphosphine)palladium(II) (9.9 g, 14.1 mmol) in N,N-dimethylformamide (500 mL) was stirred at 100° C. for 1.5 hr. The reaction solution was diluted with water, and the mixture was extracted with diethyl ether. The extract was washed with saturated brine and dried over anhydrous sodium sulfate. The solvent was evaporated under reduced pressure and the residue was purified by silica gel column chromatography (ethyl acetate/hexane=25/75→33/67) to give the title compound (30.9 g, yield 96%).

¹H-NMR (CDCl₃) δ: 0.35 (9H, s), 3.27 (2H, t, J=8.5 Hz), 3.37-3.42 (2H, m), 4.54 (2H, t, J=8.5 Hz), 4.83-4.93 (1H, m), 5.03-5.12 (1H, m), 5.88-6.04 (1H, m), 7.75 (1H, s).

Reference Example 54

3-[4-(trimethylsilyl)-2,3-dihydrofuro[2,3-b]pyridin-5-yl]propan-1-ol

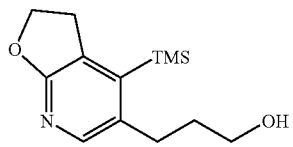

To a solution of 5-allyl-4-(trimethylsilyl)-2,3-dihydrofuro[2,3-b]pyridine (9.00 g, 38.6 mmol) in tetrahydrofuran (300 mL) was added boron trifluoride diethyl ether complex (5.38 mL, 42.5 mmol) under ice-cooling, and the mixture was warmed to room temperature. A 9-borabicyclo[3.3.1]nonane tetrahydrofuran solution (0.4M, 241 mL, 96.4 mmol) was added. After stirring for 1 hr, N,N,N',N'-tetramethylethylenediamine (3.20 mL, 21.2 mmol) was added, and a mixed solution of 30% aqueous hydrogen peroxide (100 mL) and 2.5M aqueous sodium hydroxide solution (100 mL) was further added. The mixture was extracted with ethyl acetate, and the extract was washed with saturated brine and dried over anhydrous sodium sulfate. The solvent was evaporated under reduced pressure. The residue was purified by silica gel column chromatography (ethyl acetate/hexane=5/95→60/40) to give the title compound (6.64 g, yield 68%).

¹H-NMR (CDCl₃) δ: 0.37 (9H, s), 1.73-1.88 (2H, m), 2.66-2.76 (2H, m), 3.27 (2H, t, J=8.6 Hz), 3.72 (2H, t, J=6.3 Hz), 4.54 (2H, t, J=8.6 Hz), 7.79 (1H, s), hidden (1H), melting point: 107-109° C. (recrystallized from ethyl acetate), MS (ESI+): 252 (M+H),
Elemental analysis: for $C_{13}H_{21}NO_2Si \cdot 0.2H_2O$
Calculated (%): C, 61.23; H, 8.46; N, 5.49
Found (%): C, 61.40; H, 8.32; N, 5.48.

Reference Example 55

3-[4-(trimethylsilyl)-2,3-dihydrofuro[2,3-b]pyridin-5-yl]propanal

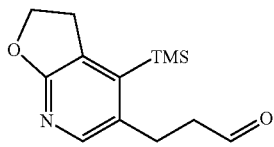

A mixture of 3-[4-(trimethylsilyl)-2,3-dihydrofuro[2,3-b]pyridin-5-yl]propan-1-ol (6.54 g, 26.0 mmol) and orthoiodoxybenzoic acid (9.47 g, 33.8 mmol) in dimethyl sulfoxide (80 mL) was stirred at room temperature for 5 hr. The reaction solution was diluted with diethyl ether, and the mixture was washed with saturated aqueous sodium hydrogen carbonate solution and saturated brine, and dried over anhydrous sodium sulfate. The solvent was evaporated under reduced pressure and the residue was purified by silica gel column chromatography (ethyl acetate/hexane=30/70→70/30) to give the title compound (5.69 g, yield 87%).

¹H-NMR (CDCl₃) δ: 0.38 (9H, s), 2.67-2.77 (2H, m), 2.91-3.01 (2H, m), 3.27 (2H, t, J=8.5 Hz), 4.55 (2H, t, J=8.5 Hz), 7.76 (1H, s), 9.83 (1H, s), melting point: 59-60° C. (recrystallized from ethyl acetate/hexane), MS (ESI+): 250 (M+H)
Elemental analysis: for $C_{13}H_{19}NO_2Si \cdot 0.2H_2O$
Calculated (%): C, 61.72; H, 7.72; N, 5.53
Found (%): C, 61.81; H, 7.77; N, 5.53.

Reference Example 56

1,6,7,8-tetrahydro-2H-cyclopenta[d]furo[2,3-b]pyridin-8-ol

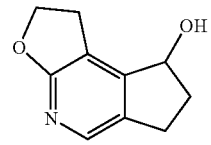

To a solution of tetrabutylammonium difluorotriphenylsilicate (43.3 mg, 0.802 mmol) in 1,2-dimethoxyethane (3 mL) heated to 70° C. was added dropwise a solution of 3-[4-(trimethylsilyl)-2,3-dihydrofuro[2,3-b]pyridin-5-yl]propanal (100 mg, 0.401 mmol) in 1,2-dimethoxyethane (1 mL). After dropwise addition, the reaction solution was diluted with saturated aqueous ammonium chloride solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane=30/70→100/0) to give the title compound (50.4 mg, yield 71%).

¹H-NMR (CDCl₃) δ: 1.88-2.06 (1H, m), 2.45-2.63 (1H, m), 2.65-2.82 (2H, m), 2.87-3.01 (1H, m), 3.11-3.31 (1H, m), 3.32-3.54 (1H, m), 4.60 (2H, t, J=8.7 Hz), 5.17-5.33 (1H, m), 7.79 (1H, s), melting point: 130-131° C. (recrystallized from ethyl acetate/hexane), MS (ESI+): 178 (M+H),
Elemental analysis: for $C_{10}H_{11}NO_2$
Calculated (%): C, 67.78; H, 6.26; N, 7.90
Found (%): C, 67.51; H, 6.25; N, 7.71.

Reference Example 57

1,2,6,7-tetrahydro-8H-cyclopenta[d]furo[2,3-b]pyridin-8-one

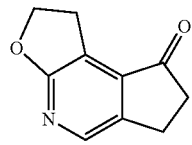

A suspension of 1,6,7,8-tetrahydro-2H-cyclopenta[d]furo[2,3-b]pyridin-8-ol (500 mg, 2.82 mmol), 4 Å molecular sieves (1 g), 4-methylmorpholine N-oxide (825 mg, 7.05 mmol) and tetra-n-propylammonium perruthenate(VII) (99 mg, 0.282 mmol) in acetonitrile (15 mL) was stirred at room temperature for 15 min. The solvent was evaporated under reduced pressure, and the residue was purified by silica gel column chromatography (ethyl acetate) to give the title compound (335 mg, yield 68%).

$^1$H-NMR (CDCl$_3$) δ: 2.68-2.80 (2H, m), 3.07-3.18 (2H, m), 3.49 (2H, t, J=8.7 Hz), 4.72 (2H, t, J=8.7 Hz), 8.24 (1H, s), MS (ESI+): 176 (M+H).

Reference Example 58

7-(1-methylethylidene)-1,2,6,7-tetrahydro-8H-cyclopenta[d]furo[2,3-b]pyridin-8-one

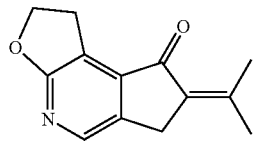

1,2,6,7-Tetrahydro-8H-cyclopenta[d]furo[2,3-b]pyridin-8-one (610 mg, 3.48 mmol), acetone (1.28 mL, 17.4 mmol) and ICN Alumina B (manufactured by ICN, Akt. 1, 10 g) were suspended in tetrahydrofuran (15 mL), and the suspension was stirred at room temperature for 3 hr. Acetone (1.28 mL, 17.4 mmol) was added, and the mixture was further stirred for 3 hr. The reaction solution was filtered, and the filtrate was evaporated under reduced pressure to give the title compound (539 mg, yield 72%).

$^1$H-NMR (CDCl$_3$) δ: 2.02 (3H, s), 2.42 (3H, s), 3.52 (2H, t, J=−8.8 Hz), 3.61 (2H, s), 4.70 (2H, t, J=8.8 Hz), 8.20 (1H, s), MS (ESI+): 216 (M+H).

Reference Example 59

7-isopropyl-1,2,6,7-tetrahydro-8H-cyclopenta[d]furo[2,3-b]pyridin-8-one

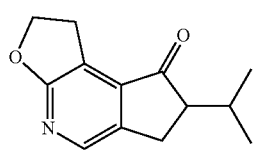

To a solution of 7-(1-methylethylidene)-1,2,6,7-tetrahydro-8H-cyclopenta[d]furo[2,3-b]pyridin-8-one (539 mg, 2.51 mmol) in methanol (20 mL) was added palladium-carbon powder (50 mg), and the mixture was stirred at room temperature for 3 hr under a hydrogen atmosphere. The catalyst was filtered off, and the filtrate was concentrated under reduced pressure. The residue was purified by silica gel column chromatography (ethyl acetate/hexane=10/90→40/60) to give the title compound (465 mg, yield 85%).

$^1$H-NMR (CDCl$_3$) δ: 0.82 (3H, d, J=2.1 Hz), 1.05 (3H, d, J=7.1 Hz), 2.31-2.46 (1H, m), 2.69 (1H, m), 2.83-2.93 (1H, dd, J=17.0, 4.4 Hz), 3.13 (1H, dd, J=17.0, 8.2 Hz), 3.48 (2H, t, J=8.6 Hz), 4.71 (2H, t, J=8.6 Hz), 8.22 (1H, s),
melting point: 68-69° C. (recrystallized from hexane),
MS (ESI+): 218 (M+H),
Elemental analysis: for C$_{13}$H$_{15}$NO$_2$
Calculated (%): C, 71.87; H, 6.96; N, 6.45
Found (%): C, 71.89; H, 6.92; N, 6.36.

Reference Example 60

1,2,6,7-tetrahydro-8H-cyclopenta[d]furo[2,3-b]pyridin-8-ylidene acetonitrile

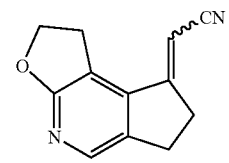

To a suspension of 60% sodium hydride (137 mg, 3.42 mmol) in tetrahydrofuran (15 mL) was added diethyl cyanomethylphosphonate (600 μL, 3.71 mmol) under ice-cooling, and the mixture was stirred for 15 min. A solution of 1,2,6,7-tetrahydro-8H-cyclopenta[d]furo[2,3-b]pyridin-8-one (500 mg, 2.85 mmol) in tetrahydrofuran (15 mL) was added thereto, and the mixture was further stirred for 15 min. The reaction mixture was diluted with saturated aqueous sodium hydrogen carbonate solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane=30/70→80/20) to give the title compound (514 mg, yield 91%).

$^1$H-NMR (CDCl$_3$) δ: 3.04-3.10 (2H, m), 3.11-3.20 (2H, m), 3.35 (2H, t, J=8.7 Hz), 4.71 (2H, t, J=8.7 Hz), 5.63 (1H, t, J=2.7 Hz), 8.05 (1H, s),
melting point: 153-155° C. (recrystallized from ethyl acetate),
MS (ESI+): 199 (M+H),
Elemental analysis: for C$_{12}$H$_{10}$N$_2$O
Calculated (%): C, 72.71; H, 5.08; N, 14.13
Found (%): C, 72.61; H, 4.92; N, 13.95.

Reference Example 61

(8-hydroxy-7-isopropyl-1,6,7,8-tetrahydro-2H-cyclopenta[d]furo[2,3-b]pyridin-8-yl)acetonitrile To a solution of 1,1,1,3,3,3-hexamethyldisilazane (684 mg, 4.24 mmol) in tetrahydrofuran (3 mL) was added 1.6M butyllithium/hexane solution (2.65 mL, 4.24 mmol) at −78° C., and the mixture was stirred for 15 min. A solution of acetonitrile (234 μL, 4.45 mmol) in tetrahydrofuran (1 mL) was added thereto, and the mixture was stirred for 30 min. Then, a solution of 7-isopropyl-1,2,6,7-tetrahydro-8H-cyclopenta[d]furo[2,3-b]pyridin-8-one (460 mg, 2.12 mmol) in tetrahydrofuran (6 mL) was added. After stirring for 20 min, the reaction solution was diluted with saturated aqueous ammonium chloride solution, and the solvent was evaporated under reduced pressure. The residue was diluted with ethyl acetate, and the mixture was washed with saturated brine, and dried over anhydrous sodium sulfate. The solvent was evaporated under reduced pressure. The residue was purified by silica gel column chromatography (ethyl acetate/hexane=30/70→80/20) to give the title compound (457 mg, yield 83%).

$^1$H-NMR (DMSO-$d_6$) δ: 0.71 (3H, d, J=6.4 Hz), 1.00 (3H, d, J=6.4 Hz), 2.00-2.14 (2H, m), 2.66 (1H, dd, J=15.8, 4.8 Hz), 2.89 (1H, dd, J=15.8, 7.0 Hz), 2.98-3.14 (2H, m), 3.39 (2H, t, J=8.7 Hz), 4.42-4.65 (2H, m), 5.81 (1H, s), 7.77 (1H, s).

melting point: 169-170° C. (recrystallized from ethyl acetate),

MS (ESI+): 259 (M+H),

Elemental analysis: for $C_{15}H_{18}N_2O_2$

Calculated (%): C, 69.74; H, 7.02; N, 10.84

Found (%): C, 69.63; H, 7.05; N, 10.77.

Reference Example 62

2-(1,2,6,7-tetrahydro-8H-cyclopenta[d]furo[2,3-b]pyridin-8-ylidene)ethanamine

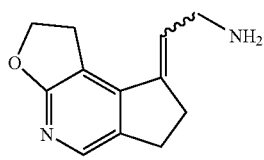

To a solution of 1,2,6,7-tetrahydro-8H-cyclopenta[d]furo[2,3-b]pyridine-8-ylideneacetonitrile (84.9 mg, 0.428 mmol) in methanol (3 mL) were added Raney cobalt (400 mg) and 2M ammonia/ethanol solution (1.5 mL), and the mixture was stirred at room temperature for 4 hr under a hydrogen atmosphere. The catalyst was filtered through celite, and the filtrate was concentrated under reduced pressure to give the title compound. The obtained title compound was used for the reaction in Example 19 without purification.

$^1$H-NMR (CDCl$_3$) δ: 2.69-2.80 (2H, m), 2.90-2.99 (2H, m), 3.32 (2H, t, J=8.5 Hz), 3.50 (2H, d, J=6.6 Hz), 4.64 (2H, t, J=8.5 Hz), 5.93-6.04 (1H, m), 7.86 (1H, s), hidden (2H).

Reference Example 63

2-(1,6,7,8-tetrahydro-2H-cyclopenta[d]furo[2,3-b]pyridin-8-yl)ethanamine

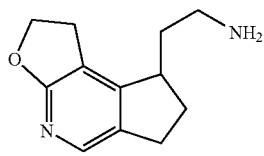

To a solution of 1,2,6,7-tetrahydro-8H-cyclopenta[d]furo[2,3-b]pyridin-8-ylideneacetonitrile (500 mg, 2.52 mmol) in ethanol (16 mL) were added Raney cobalt (1 g) and 2M ammonia/ethanol solution (8 mL), and the mixture was stirred at room temperature for 30 hr under a hydrogen atmosphere. The catalyst was filtered through celite, and the filtrate was concentrated under reduced pressure. The residue was dissolved in methanol (20 mL), palladium-carbon powder (100 mg) was added, and the mixture was stirred at room temperature for 12 hr under a hydrogen atmosphere. The catalyst was filtered off, and the filtrate was concentrated under reduced pressure to give the title compound. The obtained title compound was used for the reaction in Examples 25, 26, 27 and 28 without purification.

$^1$H-NMR (CDCl$_3$) δ: 1.50-1.68 (1H, m), 1.69-1.82 (1H, m), 1.94-2.10 (1H, m), 2.19-2.39 (1H, m), 2.59-2.95 (4H, m), 3.06-3.38 (3H, m), 4.46-4.71 (2H, m), 7.79 (1H, s), hidden (2H).

Reference Example 64

8-(2-aminoethyl)-7-isopropyl-1,6,7,8-tetrahydro-2H-cyclopenta[d]furo[2,3-b]pyridin-8-ol

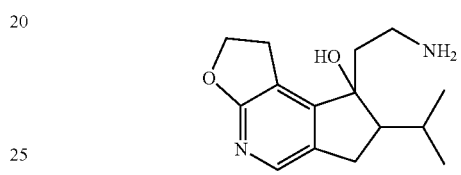

To a solution of (8-hydroxy-7-isopropyl-1,6,7,8-tetrahydro-2H-cyclopenta[d]furo[2,3-b]pyridin-8-yl)acetonitrile (440 mg, 1.70 mmol) in ethanol (12 mL) were added Raney cobalt (4 g) and 2M ammonia/ethanol solution (6 mL), and the mixture was stirred at room temperature for 4 hr under a hydrogen atmosphere. The catalyst was filtered through celite, and the filtrate was concentrated under reduced pressure to give the title compound (446 mg, yield 100%).

$^1$H-NMR (CDCl$_3$) δ: 0.49 (3H, d, J=6.9 Hz), 0.95 (3H, d, J=6.9 Hz), 1.42 (2H, brs), 1.65-1.76 (1H, m), 1.77-1.88 (1H, m), 2.20-2.36 (2H, m), 2.71 (2H, d, J=4.7 Hz), 2.96-3.18 (2H, m), 3.17-3.31 (1H, m), 3.46-3.61 (1H, m), 4.55-4.66 (2H, m), 7.07 (1H, brs), 7.74 (1H, s), melting point: 142-143° C. (recrystallized from methanol/diisopropyl ether),

MS (ESI+): 263 (M+H),

Elemental analysis: for $C_{15}H_{22}N_2O_2 \cdot 0.2H_2O$

Calculated (%): C, 67.74; H, 8.49; N, 10.53

Found (%): C, 67.93; H, 8.33; N, 10.41.

Reference Example 65 methyl 4-[(2-ethoxy-2-oxoethyl)amino]-4-oxobutanoate

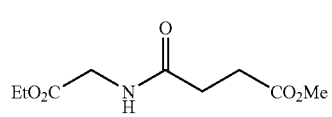

To a suspension of glycine ethyl ester hydrochloride (5.00 g, 35.8 mmol) in tetrahydrofuran (300 mL) were added triethylamine (9.99 mL, 71.6 mmol) and methyl 4-chloro-4-oxobutyrate (5.39 g, 35.8 mmol) under ice-cooling, and the mixture was stirred at room temperature for 30 min. The reaction mixture was diluted with water, and the mixture was extracted with ethyl acetate. The extract was washed with saturated aqueous sodium hydrogen carbonate solution and saturated brine, and dried over anhydrous magnesium sulfate. The solvent was evaporated under reduced pressure and the residue was purified by recrystallization (ethyl acetate/hexane) to give the title compound (5.05 g, yield 65%).

$^1$H-NMR (CDCl$_3$) δ: 1.29 (3H, t, J=7.0 Hz), 2.56 (2H, t, J=6.2 Hz), 2.69 (2H, t, J=6.2 Hz), 3.69 (3H, s), 4.03 (2H, d, J=4.9 Hz), 4.21 (2H, q, J=7.0 Hz), 6.17 (1H, s), melting point: 61-62° C. (recrystallized from ethyl acetate/hexane), Elemental analysis: for C$_9$H$_{15}$NO$_5$
Calculated (%): C, 49.76; H, 6.96; N, 6.45
Found (%): C, 49.80; H, 6.95; N, 6.39.

Reference Example 66 methyl 3-(5-ethoxy-1,3-oxazol-2-yl)propanoate

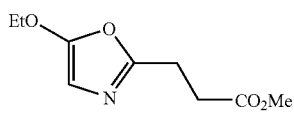

To a suspension of diphosphorus pentoxide (70.0 g, 433 mmol) in acetonitrile (200 mL) was added a solution of methyl 4-[(2-ethoxy-2-oxoethyl)amino]-4-oxobutanoate (20.0 g, 92.1 mmol) in acetonitrile (50 mL) at room temperature under an argon gas atmosphere. The mixture was stirred at 60° C. for 1 hr and poured into saturated brine (1.5 L), and the mixture was extracted with ethyl acetate. The extract was dried over anhydrous sodium sulfate. The solvent was evaporated under reduced pressure and the residue was purified by silica gel column chromatography (ethyl acetate/hexane=0/100→30/70) to give the title compound (7.06 g, yield 38%).

$^1$H-NMR (CDCl$_3$) δ: 1.41 (3H, t, J=7.2 Hz), 2.72-2.80 (2H, m), 2.92-3.01 (2H, m), 3.70 (3H, s), 4.08 (2H, q, J=7.2 Hz), 5.95 (1H, s).

Reference Example 67 dimethyl 5-hydroxy-2-(3-methoxy-3-oxopropyl)pyridine-3,4-dicarboxylate

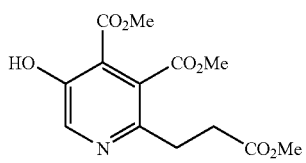

A mixture of methyl 3-(5-ethoxy-1,3-oxazol-2-yl)propanoate (7.00 g, 35.1 mmol) and maleic anhydride (3.44 g, 35.1 mmol) was stirred at room temperature for 2 hr, 10% hydrochloric acid-methanol solution (100 mL) was added, and the mixture was heated under reflux for 15 hr. The solvent was evaporated under reduced pressure, and the residue was purified by silica gel column chromatography (ethyl acetate/methanol=100/0→70/30). The purified product was dissolved in methanol, 2M trimethylsilyldiazomethane/diethyl ether solution (34 mL, 68 mmol) was added at room temperature, and the mixture was stirred for 30 min. The solvent was evaporated under reduced pressure, and the residue was purified by silica gel column chromatography (ethyl acetate/hexane=25/75→50/50) to give the title compound (3.10 g, yield 30%).

$^1$H-NMR (CDCl$_3$) δ: 2.72-2.82 (2H, m), 2.96-3.04 (2H, m), 3.67 (3H, s), 3.94 (3H, s), 3.96 (3H, s), 8.47 (1H, s), 10.23 (1H, s), melting point: 66-67° C. (recrystallized from ethyl acetate/diisopropyl ether), MS (ESI+): 298 (M+H),
Elemental analysis: for C$_{13}$H$_{15}$NO$_5$
Calculated (%): C, 52.53; H, 5.09; N, 4.71
Found (%): C, 52.51; H, 4.94; N, 4.67.

Reference Example 68 dimethyl 5-(2-methoxy-2-oxoethoxy)-2-(3-methoxy-3-oxopropyl)pyridine-3,4-dicarboxylate

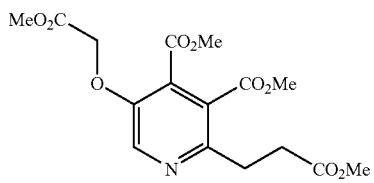

To a mixture of dimethyl 5-hydroxy-2-(3-methoxy-3-oxopropyl)pyridine-3,4-dicarboxylate (5.10 g, 17.2 mmol) and potassium carbonate (12.3 g, 69.0 mmol) in acetone (100 mL) was added methyl bromoacetate (3.26 mL, 34.4 mmol) at room temperature, and the mixture was stirred for 30 min. The solvent was evaporated under reduced pressure, the residue was diluted with water, and the mixture was extracted with ethyl acetate. The extract was dried over anhydrous sodium sulfate. The solvent was evaporated under reduced pressure and the residue was purified by silica gel column chromatography (ethyl acetate/hexane=10/90→40/60) to give the title compound (5.14 g, yield 81%).

$^1$H-NMR (CDCl$_3$) δ: 2.79 (2H, t, J=7.3 Hz), 3.25 (2H, t, J=7.3 Hz), 3.67 (3H, s), 3.80 (3H, s), 3.90 (3H, s), 3.92 (3H, s), 4.75 (2H, s), 8.30 (1H, s),

MS (ESI+): 370 (M+H).

Reference Example 69 dimethyl 3-hydroxy-5-(3-methoxy-3-oxopropyl)furo[2,3-c]pyridine-2,4-dicarboxylate

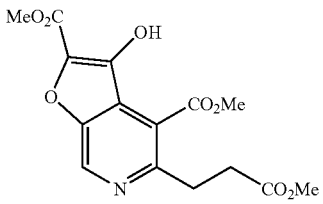

To a solution of dimethyl 5-(2-methoxy-2-oxoethoxy)-2-(3-methoxy-3-oxopropyl)pyridine-3,4-dicarboxylate (2.20 g, 5.96 mmol) in methanol (60 mL) was added sodium methoxide (0.805 g, 14.9 mmol) at 80° C., and the mixture was stirred for 30 min. The resulting precipitate was collected by filtration, washed with methanol, and dissolved in 1M hydrochloric acid (10 mL). The mixture was extracted with ethyl acetate and the extract was dried over anhydrous sodium sulfate. The solvent was evaporated under reduced pressure and the residue was purified by recrystallization (ethyl acetate/diisopropyl ether) to give the title compound (1.35 g, yield 67%).

$^1$H-NMR (CDCl$_3$) δ: 2.86 (2H, t, J=7.3 Hz), 3.51 (2H, t, J=7.3 Hz), 3.68 (3H, s), 4.03 (3H, s), 4.11 (3H, s), 8.93 (1H, s), 10.13 (1H, brs), melting point: 117-118° C. (recrystallized from ethyl acetate/diisopropyl ether),

MS (ESI+): 338 (M+H),

Elemental analysis: for C$_{15}$H$_{15}$NO$_8$

Calculated (%): C, 53.42; H, 4.48; N, 4.15

Found (%): C, 53.44; H, 4.41; N, 4.14.

Reference Example 70 methyl 5-(3-methoxy-3-oxopropyl)-2,3-dihydrofuro [2,3-c]pyridine-4-carboxylate

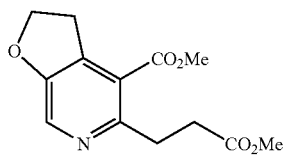

A mixture of dimethyl 3-hydroxy-5-(3-methoxy-3-oxopropyl)furo[2,3-c]pyridine-2,4-dicarboxylate (3.10 g, 9.19 mmol) and 12M hydrochloric acid (31 mL) was stirred at 150° C. for 1 hr and concentrated under reduced pressure. The residue was dissolved in methanol (60 mL), palladium-carbon powder (600 mg) was added, and the mixture was stirred at room temperature for 3 hr under a hydrogen atmosphere. The catalyst was filtered off, and the filtrate was evaporated under reduced pressure. The residue was dissolved in methanol (60 mL) again, palladium-carbon powder (1.00 g) was added, and the mixture was stirred at 50° C. for 4 hr under a hydrogen atmosphere. The catalyst was filtered off, and the filtrate was evaporated under reduced pressure. The residue was dissolved in methanol (60 mL), 2M trimethylsilyldiazomethane/diethyl ether solution (9.2 mL, 18 mmol) was added under ice-cooling, and the mixture was stirred for 30 min. The reaction solution was diluted with saturated aqueous sodium hydrogen carbonate solution, and the mixture was extracted with ethyl acetate. The extract was dried over anhydrous sodium sulfate, and the solvent was evaporated under reduced pressure to give the title compound (1.98 g, yield 81%).

$^1$H-NMR (CDCl$_3$) δ: 2.78 (2H, t, J=7.4 Hz), 3.33 (2H, t, J=7.4 Hz), 3.43 (2H, t, J=8.8 Hz), 3.66 (3H, s), 3.92 (3H, s), 4.62 (2H, t, J=8.8 Hz), 8.13 (1H, s), melting point: 80-81° C. (recrystallized from ethyl acetate), Elemental analysis: for C$_{13}$H$_{15}$NO$_5$ Calculated (%): C, 58.86; H, 5.70; N, 5.28

Found (%): C, 58.81; H, 5.67; N, 5.24.

Reference Example 71

1,2,6,7-tetrahydro-8H-cyclopenta[b]furo[3,2-d]pyridin-8-one

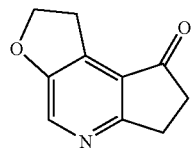

To a suspension of 65% sodium hydride (1.38 g, 37.4 mmol) in tetrahydrofuran (10 mL) were added a solution of methyl 5-(3-methoxy-3-oxopropyl)-2,3-dihydrofuro[2,3-c]pyridine-4-carboxylate (1.98 g, 7.46 mmol) in tetrahydrofuran (80 mL) and methanol (0.2 mL), and the mixture was stirred at 80° C. for 10 min. 12M Hydrochloric acid (40 mL) was added thereto under ice-cooling, and the organic solvent was evaporated under reduced pressure. The residual aqueous solution was stirred at 150° C. for 20 min, the reaction mixture was basified with 8M aqueous sodium hydroxide solution under ice-cooling, and extracted with ethyl acetate. The extract was dried over anhydrous sodium sulfate. The solvent was evaporated under reduced pressure and the residue was purified by silica gel column chromatography (ethyl acetate/hexane=10/90→40/60) to give the title compound (886 mg, yield 68%).

$^1$H-NMR (CDCl$_3$) δ: 2.75-2.82 (2H, m), 3.17-3.23 (2H, m), 3.49 (2H, t, J=8.9 Hz), 4.71 (2H, t, J=8.9 Hz), 8.31 (1H, s), melting point: 148-149° C. (recrystallized from hexane/ethyl acetate), Elemental analysis: for C$_{10}$H$_9$NO$_2$ Calculated (%): C, 68.56; H, 5.18; N, 8.00

Found (%): C, 68.61; H, 5.18; N, 8.03.

Reference Example 72

(2E)-1,2,6,7-tetrahydro-8H-cyclopenta[b]furo[3,2-d]pyridin-8-ylideneacetonitrile

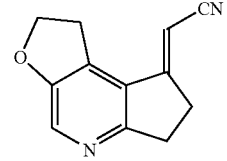

To a solution of diethyl cyanomethylphosphonate (757 mg, 4.27 mmol) in tetrahydrofuran (20 mL) was added 65% sodium hydride (137 mg, 3.71 mmol) under ice-cooling, and the mixture was stirred at room temperature for 30 min. The mixture was added to a solution of 1,2,6,7-tetrahydro-8H-cyclopenta[b]furo[3,2-d]pyridin-8-one (500 mg, 2.85 mmol) in tetrahydrofuran (10 mL) under ice-cooling, and the mixture was stirred for 10 min. The reaction solution was diluted with saturated aqueous sodium hydrogen carbonate solution, and the mixture was extracted with ethyl acetate. The extract was dried over anhydrous sodium sulfate. The solvent was

Reference Example 73

(2E)-2-(1,2,6,7-tetrahydro-8H-cyclopenta[b]furo[3,2-d]pyridin-8-ylidene)ethanamine

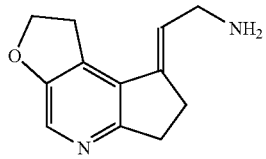

A suspension of (2E)-1,2,6,7-tetrahydro-8H-cyclopenta[b]furo[3,2-d]pyridin-8-ylideneacetonitrile (10.0 mg, 0.054 mmol) and Raney cobalt (100 mg) in 2M ammonia/ethanol (1 mL) was stirred at 50° C. for 3 hr under a hydrogen atmosphere. The catalyst was filtered through celite, and the filtrate was concentrated under reduced pressure to give the title compound (10.0 mg, yield 99%).

$^1$H-NMR (CDCl$_3$) δ: 2.75-2.83 (2H, m), 2.99-3.06 (2H, m), 3.31 (2H, t, J=8.7 Hz), 3.47-3.54 (2H, m), 4.64 (2H, d, J=8.7 Hz), 5.80-5.92 (1H, m), 7.94 (1H, s), hidden (2H).

Reference Example 74

2-[(dimethylamino)methyl]pyridin-3-ol

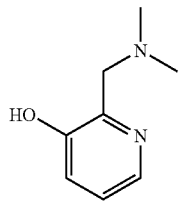

To a solution of 4-hydroxypyridine (200 g, 2.10 mol) in water (500 mL) were added 50% aqueous dimethylamine (228 g) solution and 36% aqueous formalin (210 g) solution, and the mixture was stirred at 50° C. for 4 hr. The solvent was evaporated under reduced pressure, and the resulting crystals were collected by filtration to give the title compound (207 g, yield 65%).

$^1$H-NMR (CDCl$_3$) δ: 2.38 (6H, s), 3.86 (2H, s), 7.01-7.18 (2H, m), 8.00 (1H, t, J=3.2 Hz), hidden (1H).

Reference Example 75

(3-hydroxypyridin-2-yl)-N,N,N-trimethylmethanaminium iodide

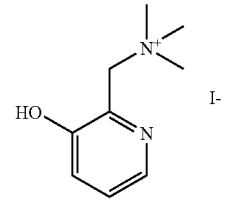

To a solution of 2-[(dimethylamino)methyl]pyridin-3-ol (207 g, 1.37 mol) in acetone (2000 mL) was added dropwise iodomethane (778 g, 5.48 mol) under ice-cooling, and the mixture was stirred at room temperature for 3 hr. The resulting crystals were collected by filtration to give the title compound (369 g, yield 92%).

$^1$H-NMR (METHANOL-d$_4$) δ: 3.21 (9H, s), 4.61 (2H, s), 7.30-7.45 (2H, m), 8.15-8.28 (1H, m), hidden (1H).

Reference Example 76

2,3-dihydrofuro[3,2-b]pyridine

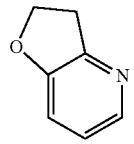

To a suspension of 60% sodium hydride (11.4 g, 286 mmol) in DMSO (170 mL) was added trimethylsulfonium iodide (29.9 g, 136 mmol), and the mixture was stirred at room temperature for 30 min. A solution of (3-hydroxypyridin-2-yl)-N,N,N-trimethylmethanaminium iodide (40.0 g, 136 mmol) in DMSO (130 mL) was added dropwise thereto, and the mixture was further stirred at room temperature for 2 hr. The reaction mixture was diluted with water, and the mixture was extracted with ethyl acetate. 1M Hydrochloric acid was added to the extract, and the mixture was extracted with water. The extract was basified with 1M aqueous sodium hydroxide solution and extracted again with ethyl acetate. The extract was washed with saturated brine and dried over anhydrous sodium sulfate. The solvent was evaporated under reduced pressure and the residue was purified by silica gel column chromatography (ethyl acetate/hexane=20/80→50/50) to give the title compound (7.77 g, yield 47%).

--- evaporated under reduced pressure and the residue was purified by recrystallization (ethyl acetate) to give the title compound (337 mg, yield 60%).

$^1$H-NMR (CDCl$_3$) δ: 3.13-3.17 (4H, m), 3.33 (2H, t, J=8.8 Hz), 4.72 (2H, t, J=8.8 Hz), 5.48-5.52 (1H, m), 8.14 (1H, s), melting point: 231-233° C. (recrystallized from ethyl acetate), Elemental analysis: for C$_{12}$H$_{10}$NO$_2$ Calculated (%): C, 72.71; H, 5.08; N, 14.13

Found (%): C, 72.44; H, 5.03; N, 14.01.

$^1$H-NMR (CDCl$_3$) δ: 3.33 (2H, t, J=8.8 Hz), 4.65 (2H, t, J=8.8 Hz), 6.98-7.01 (2H, m), 8.00-8.04 (1H, m).

Reference Example 77

5-nitro-2,3-dihydrofuro[3,2-b]pyridine

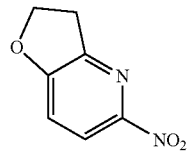

To a solution of 2,3-dihydrofuro[3,2-b]pyridine (32.9 g, 271 mmol) in sulfuric acid (50 mL) was added dropwise a mixed solution of fuming nitric acid (20 mL) and sulfuric acid (20 mL) under ice-cooling, and the mixture was stirred at room temperature for 1 hr. The reaction solution was neutralized with 8M aqueous sodium hydroxide solution and diluted with water. The resulting crystals were collected by filtration to give the title compound (37.5 g, yield 83%).

$^1$H-NMR (CDCl$_3$) δ: 3.45 (2H, t, J=8.9 Hz), 4.86 (2H, t, J=8.9 Hz), 7.17 (1H, d, J=9.3 Hz), 8.14 (1H, d, J=9.3 Hz).

Reference Example 78

2,3-dihydrofuro[3,2-b]pyridin-5-amine

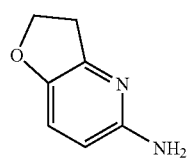

To a solution of 5-nitro-2,3-dihydrofuro[3,2-b]pyridine (7.41 g, 44.6 mmol) in methanol (100 mL) was added palladium-carbon powder (500 mg), and the mixture was stirred at room temperature for 16 hr under a hydrogen atmosphere. The catalyst was filtered through celite, and the filtrate was concentrated under reduced pressure. The residue was purified by recrystallization (ethyl acetate/hexane) to give the title compound (4.87 g, yield 80%).

$^1$H-NMR (CDCl$_3$) δ: 3.19 (2H, t, J=8.9 Hz), 4.11 (2H, s), 4.57 (2H, t, J=8.9 Hz), 6.27 (1H, d, J=8.5 Hz), 6.90 (1H, d, J=8.5 Hz), melting point: 129-131° C. (recrystallized from ethyl acetate/hexane), Elemental analysis: for C$_7$H$_8$N$_2$O Calculated (%): C, 61.75; H, 5.92; N, 20.58

Found (%): C, 61.78; H, 5.91; N, 20.50.

Reference Example 79

7-phenyl-1,2-dihydrofuro[2,3-e]imidazo[1,2-a]pyridine

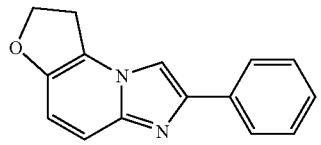

To a solution of 2,3-dihydrofuro[3,2-b]pyridin-5-amine (500 mg, 3.67 mmol) in ethanol (30 mL) were added 2-bromo-1-phenylethanone (730 mg, 3.67 mmol) and sodium carbonate (467 mg, 4.40 mmol), and the mixture was stirred at 80° C. for 14 hr. The solvent was evaporated under reduced pressure, and the residue was purified by silica gel column chromatography (ethyl acetate/hexane=20/80→50/50) to give the title compound (136 mg, yield 16%).

$^1$H-NMR (CDCl$_3$) δ: 3.46 (2H, t, J=9.1 Hz), 4.80 (2H, t, J=9.1 Hz), 6.97 (1H, d, J=9.6 Hz), 7.27-7.36 (1H, m), 7.38-7.53 (3H, m), 7.60 (1H, s), 7.89-8.00 (2H, m).

Reference Example 80

N,N-dimethyl-1-(7-phenyl-1,2-dihydrofuro[2,3-e]imidazo[1,2-a]pyridin-8-yl)methanamine 7-Phenyl-1,2-dihydrofuro[2,3-e]imidazo[1,2-a]pyridine (40 mg, 0.169 mol) was dissolved in a mixed solvent of water (400 μL) and acetonitrile (1 mL), 50% aqueous dimethylamine (15.1 mg) solution and 36% aqueous formalin (14.2 mg) solution were added, and the mixture was stirred at 70° C. for 4 hr. The solvent was evaporated under reduced pressure, and the residue was purified by silica gel column chromatography (ethyl acetate/hexane=80/20→100/0) to give the title compound (45 mg, 95%).

¹H-NMR (CDCl₃) δ: 2.11 (6H, s), 3.79 (2H, s), 3.94 (2H, t, J=9.1 Hz), 4.74 (2H, t, J=9.1 Hz), 6.97 (1H, d, J=9.3 Hz), 7.30-7.52 (4H, m), 7.60-7.75 (2H, m).

Reference Example 81

(7-phenyl-1,2-dihydrofuro[2,3-e]imidazo[1,2-a]pyridin-8-yl)acetonitrile

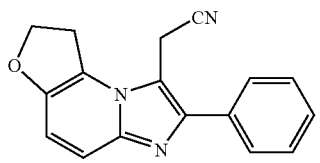

A solution of N,N-dimethyl-1-(7-phenyl-1,2-dihydrofuro[2,3-e]imidazo[1,2-a]pyridin-8-yl)methanamine (86.0 mg, 0.293 mmol) and iodomethane (166 mg, 1.17 mmol) in acetone (1 mL) was stirred at room temperature for 5 hr, and the resulting crystals were collected by filtration. The crystals were dissolved in a mixed solvent of ethanol (1 mL) and water (1 mL), sodium cyanide (59.3 mg) was added, and the mixture was stirred at 70° C. for 1 hr. The reaction solution was diluted with saturated aqueous sodium hydrogen carbonate solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane=40/60→80/20) to give the title compound (12.9 mg, yield 17%).

¹H-NMR (CDCl₃) δ: 3.98 (2H, t, J=8.8 Hz), 4.18 (2H, s), 4.82 (2H, t, J=8.8 Hz), 7.05 (1H, d, J=9.6 Hz), 7.37-7.57 (4H, m), 7.61-7.72 (2H, m).

Reference Example 82

1-(2-ethyl-8,9-dihydrofuro[3,2-c]pyrazolo[1,5-a]pyridin-1-yl)ethanone

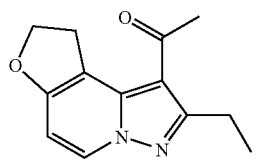

A mixture of 5-amino-2,3-dihydrofuro[3,2-c]pyridin-5-ium 2,4-dinitrobenzenolate (2.00 g, 6.24 mmol), potassium carbonate (1.21 g, 8.75 mmol) and 3-hexyn-2-one (0.750 mL, 6.87 mmol) in dimethylformamide (30 mL) was stirred at 40° C. for 16 hr, water was added, and the mixture was extracted with ethyl acetate. The extract was washed with saturated brine, dried over anhydrous sodium sulfate and filtered. The solvent was evaporated under reduced pressure and the residue was purified by silica gel column chromatography (ethyl acetate/hexane=20/80→40/60) to give the title compound (314 mg, yield 22%).

¹H-NMR (CDCl₃) δ: 1.40 (3H, t, J=7.4 Hz), 2.52 (3H, s), 3.04 (2H, q, J=7.4 Hz), 3.78 (2H, t, J=9.1 Hz), 4.70 (2H, t, J=9.1 Hz), 6.57 (1H, d, J=7.1 Hz), 8.17-8.22 (1H, m), melting point: 164-165° C. (recrystallized from ethyl acetate/hexane),
MS (ESI+): 231 (M+H),
Elemental analysis: for C₁₃H₁₄N₂O₂
Calculated (%): C, 67.81; H, 6.13; N, 12.17
Found (%): C, 67.72; H, 6.14; N, 12.17.

Reference Example 83

1-(2-ethyl-8,9-dihydrofuro[3,2-c]pyrazolo[1,5-a]pyridin-1-yl)ethanol

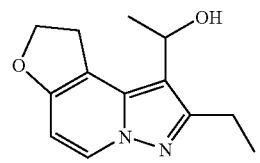

To a suspension of 80% lithium aluminum hydride (233 mg, 5.03 mmol) in tetrahydrofuran (13 mL) was added a solution of 1-(2-ethyl-8,9-dihydrofuro[3,2-c]pyrazolo[1,5-a]pyridin-1-yl)ethanone (290 mg, 1.26 mmol) in tetrahydrofuran (13 mL) under ice-cooling, and the mixture was stirred at room temperature for 1 hr. Sodium sulfate decahydrate (2.9 g) was added under ice-cooling, and the insoluble material was filtered off. The filtrate was concentrated under reduced pressure to give the title compound (265 mg, yield 90%).

¹H-NMR (CDCl₃) δ: 1.31 (3H, t, J=7.6 Hz), 1.55 (3H, d, J=6.6 Hz), 2.76-2.87 (2H, m), 3.35-3.62 (2H, m), 4.62-4.78 (2H, m), 5.19 (1H, q, J=6.6 Hz), 6.40 (1H, d, J=7.1 Hz), 8.12-8.17 (1H, m), hidden (1H), melting point: 124-126° C. (recrystallized from ethyl acetate),
MS (ESI+): 233 (M+H),
Elemental analysis: for C₁₃H₁₆N₂O₂
Calculated (%): C, 67.22; H, 6.94; N, 12.06
Found (%): C, 66.92; H, 6.91; N, 12.04.

Reference Example 84

2-(2-ethyl-8,9-dihydrofuro[3,2-c]pyrazolo[1,5-a]pyridin-1-yl)propanenitrile

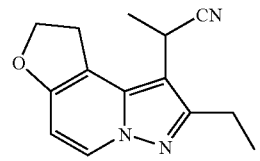

Under an argon atmosphere, to a solution of boron trifluoride diethyl ether complex (0.411 mL, 3.24 mmol) and trimethylsilyl cyanide (0.576 mL, 4.32 mmol) in chlorobenzene (10 mL) was added a solution of 1-(2-ethyl-8,9-dihydrofuro[3,2-c]pyrazolo[1,5-a]pyridin-1-yl)ethanol (250 mg, 1.08 mmol) in chlorobenzene (20 mL) under ice-cooling, and the mixture was stirred at room temperature for 15 min. A saturated aqueous sodium hydrogen carbonate solution was added, and the mixture was extracted with ethyl acetate. The extract was washed with saturated brine, dried over anhydrous sodium sulfate and filtered. The solvent was evaporated under reduced pressure and the residue was purified by silica gel column chromatography (ethyl acetate/hexane=5/95→40/60) to give the title compound (195 mg, yield 75%).

¹H-NMR (CDCl₃) δ: 1.35 (3H, t, J=7.6 Hz), 1.65 (3H, d, J=7.4 Hz), 2.77-2.87 (2H, m), 3.41-3.55 (1H, m), 3.62-3.77 (1H, m), 4.06 (1H, q, J=7.4 Hz), 4.71-4.80 (2H, m), 6.45 (1H, d, J=7.4 Hz), 8.15-8.20 (1H, m), melting point: 86-88° C. (recrystallized from ethyl acetate/hexane), MS (ESI+): 242 (M+H),
Elemental analysis: for C₁₄H₁₅N₃O
Calculated (%): C, 69.69; H, 6.27; N, 17.41
Found (%): C, 69.63; H, 6.27; N, 17.56.

Reference Example 85

2-(2-ethyl-8,9-dihydrofuro[3,2-c]pyrazolo[1,5-a]pyridin-1-yl)propan-1-amine

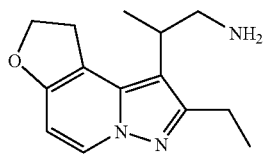

A mixture of 2-(2-ethyl-8,9-dihydrofuro[3,2-c]pyrazolo[1,5-a]pyridin-1-yl)propanenitrile (185 mg, 0.767 mmol), Raney cobalt (1.9 g) and 2M ammonia/ethanol solution (15 mL) was stirred at room temperature for 12 hr under a hydrogen atmosphere, and further stirred at 40° C. for 3 hr. The catalyst was filtered through celite, and the filtrate was concentrated under reduced pressure to give the title compound (185 mg, yield 98%).

¹H-NMR (CDCl₃) δ: 1.29-1.38 (6H, m), 2.81 (2H, q, J=7.7 Hz), 2.88-2.95 (2H, m), 2.97-3.11 (1H, m), 3.33-3.55 (2H, m), 4.69 (2H, t, J=9.1 Hz), 6.37 (1H, d, J=7.4 Hz), 8.16 (1H, d, J=7.4 Hz), hidden (2H),
MS (ESI+): 246 (M+H).

Reference Example 86

2-methylfuro[3,2-c]pyridine

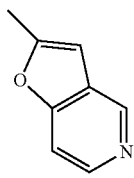

A n-butyllithium/hexane solution (1.6M, 8.55 mL, 13.7 mmol) was added to a solution of diisopropylamine (1.92 mL, 13.7 mmol) in tetrahydrofuran (20 mL) under ice-cooling. After stirring for 30 min, the mixture was cooled to −78° C. A solution of furo[3,2-c]pyridine (1.36 g, 11.4 mmol) in tetrahydrofuran (20 mL) was added to the mixture at −78° C., and the mixture was stirred for 30 min. A solution of methyl iodide (1.94 g, 13.7 mmol) in tetrahydrofuran (20 mL) was added to the mixture at −78° C., and the mixture was stirred at room temperature for 30 min. A saturated aqueous sodium hydrogen carbonate solution and water were added, and the mixture was extracted with ethyl acetate. The extract was washed with saturated brine, dried over anhydrous sodium sulfate and filtered, and the solvent was evaporated under reduced pressure. The residue was purified by silica gel column chromatography (NH, ethyl acetate/hexane=10/90→40/60) to give the title compound (1.20 g, yield 79%).

¹H-NMR (CDCl₃) δ: 2.49 (3H, d, J=1.1 Hz), 6.42-6.45 (1H, m), 7.31-7.35 (1H, m), 8.40 (1H, d, J=5.8 Hz), 8.79 (1H, s),
MS (ESI+): 134 (M+H).

Reference Example 87

5-amino-2-methylfuro[3,2-c]pyridin-5-ium 2,4-dinitrobenzenolate

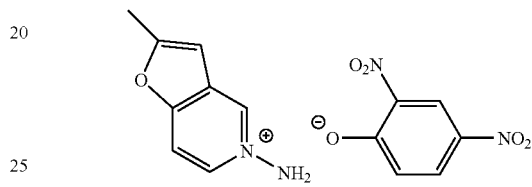

A mixture of 2-methylfuro[3,2-c]pyridine (1.20 g, 8.99 mmol) and 1-(aminooxy)-2,4-dinitrobenzene (1.79 g, 8.99 mmol) in acetonitrile (9.0 mL) was stirred at 30° C. for 22 hr, and diethyl ether was added. The resulting precipitate was collected by filtration to give the title compound (2.44 g, yield 82%).

¹H-NMR (DMSO-d₆) δ: 2.59 (3H, s), 6.29 (1H, d, J=10.2 Hz), 7.01-7.06 (1H, m), 7.71-7.79 (1H, m), 8.11 (2H, s), 8.22 (1H, d, J=6.9 Hz), 8.57 (1H, d, J=3.0 Hz), 8.64 (1H, dd, J=6.9, 1.9 Hz), 9.17 (1H, d, J=1.9 Hz).

Reference Example 88 ethyl 2-ethyl-8-methylfuro[3,2-c]pyrazolo[1,5-a]pyridine-1-carboxylate

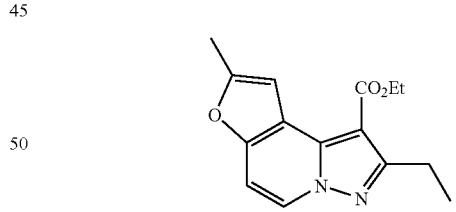

A mixture of 5-amino-2-methylfuro[3,2-c]pyridin-5-ium 2,4-dinitrobenzenolate (1.44 g, 4.33 mmol), potassium carbonate (838 mg, 6.06 mmol) and ethyl 2-pentynoate (628 μL, 4.76 mmol) in dimethylformamide (20 mL) was stirred at room temperature for 14 hr. The reaction solution was diluted with water, and the mixture was extracted with diethyl ether. The extract was washed with saturated brine, dried over anhydrous sodium sulfate and filtered. The solvent was evaporated under reduced pressure and the residue was purified by silica gel column chromatography (ethyl acetate/hexane=10/90→30/70) to give the title compound (451 mg, yield 38%).

¹H-NMR (CDCl₃) δ: 1.36 (3H, t, J=7.4 Hz), 1.46 (3H, t, J=7.1 Hz), 2.51 (3H, d, J=1.1 Hz), 3.11 (2H, q, J=7.4 Hz), 4.42 (2H, q, J=7.1 Hz), 7.05 (1H, dd, J=7.4, 0.8 Hz), 7.33-7.36 (1H, m), 8.24 (1H, d, J=7.4 Hz),
melting point: 89-90° C. (recrystallized from ethyl acetate/hexane),
MS (ESI+): 273 (M+H),
Elemental analysis: for $C_{15}H_{16}N_2O_3$
Calculated (%): C, 66.16; H, 5.92; N, 10.29
Found (%): C, 66.16; H, 5.92; N, 10.39.

Reference Example 89

(2-ethyl-8-methylfuro[3,2-c]pyrazolo[1,5-a]pyridin-1-yl)methanol

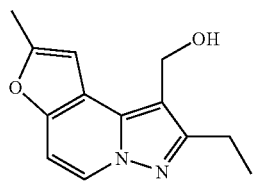

To a suspension of 80% lithium aluminum hydride (293 mg, 7.91 mmol) in tetrahydrofuran (16 mL) was added a solution of ethyl 2-ethyl-8-methylfuro[3,2-c]pyrazolo[1,5-a]pyridine-1-carboxylate (430 mg, 1.26 mmol) in tetrahydrofuran (16 mL) under ice-cooling, and the mixture was stirred at room temperature for 30 min. Sodium sulfate decahydrate (4.3 g) was added under ice-cooling, and the insoluble material was filtered off. The filtrate was concentrated under reduced pressure, and the residue was washed with diisopropyl ether to give the title compound (360 mg, yield 99%).
$^1$H-NMR (CDCl$_3$) δ: 1.36 (3H, t, J=7.7 Hz), 1.45 (1H, t, J=4.7 Hz), 2.49 (3H, d, J=1.1 Hz), 2.87 (2H, q, J=7.7 Hz), 4.88 (2H, d, J=4.7 Hz), 6.72-6.74 (1H, m), 6.87 (1H, dd, J=7.4, 0.8 Hz), 8.16 (1H, d, J=7.4 Hz),
melting point: 127-129° C. (recrystallized from ethyl acetate/diisopropyl ether),
MS (ESI+): 231 (M+H),
Elemental analysis: for $C_{13}H_{14}N_2O_2$
Calculated (%): C, 67.81; H, 6.13; N, 12.17
Found (%): C, 67.54; H, 5.91; N, 11.99.

Reference Example 90

(2-ethyl-8-methylfuro[3,2-c]pyrazolo[1,5-a]pyridin-1-yl)acetonitrile

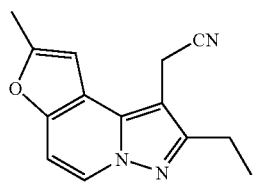

Under an argon atmosphere, to a solution of boron trifluoride diethyl ether complex (0.563 mL, 4.44 mmol) and trimethylsilyl cyanide (0.789 mL, 5.92 mmol) in chlorobenzene (30 mL) was added a solution of (2-ethyl-8-methylfuro[3,2-c]pyrazolo[1,5-a]pyridin-1-yl)methanol (340 mg, 1.48 mmol) in chlorobenzene (15 mL) under ice-cooling, and the mixture was stirred at room temperature for 15 min. A saturated aqueous sodium hydrogen carbonate solution was added, and the mixture was extracted with ethyl acetate. The extract was washed with saturated brine, dried over anhydrous sodium sulfate and filtered. The solvent was evaporated under reduced pressure and the residue was purified by silica gel column chromatography (ethyl acetate/hexane=10/90→30/70) to give the title compound (252 mg, yield 71%).
$^1$H-NMR (CDCl$_3$) δ: 1.38 (3H, t, J=7.7 Hz), 2.52 (3H, d, J=1.1 Hz), 2.85 (2H, q, J=7.7 Hz), 3.85 (2H, s), 6.71-6.73 (1H, m), 6.93 (1H, dd, J=7.4, 0.8 Hz), 8.18 (1H, d, J=7.4 Hz),
melting point: 156-157° C. (recrystallized from ethyl acetate/hexane),
MS (ESI+): 240 (M+H).

Reference Example 91

2-(2-ethyl-8-methylfuro[3,2-c]pyrazolo[1,5-a]pyridin-1-yl)ethanamine

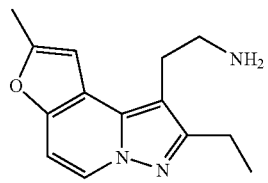

A mixture of (2-ethyl-8-methylfuro[3,2-c]pyrazolo[1,5-a]pyridin-1-yl)acetonitrile (232 mg, 0.970 mmol), Raney cobalt (2.3 g) and 2M ammonia/ethanol solution (20 mL) was stirred at room temperature for 16 hr under a hydrogen atmosphere. The catalyst was filtered through celite, and the filtrate was concentrated under reduced pressure to give the title compound (225 mg, yield 95%).
$^1$H-NMR (CDCl$_3$) δ: 1.36 (3H, t, J=7.6 Hz), 2.48 (3H, d, J=0.8 Hz), 2.83 (2H, q, J=7.6 Hz), 2.94-3.00 (4H, m), 6.65-6.67 (1H, m), 6.82 (1H, dd, J=7.4, 0.8 Hz), 8.15 (1H, d, J=7.4 Hz), hidden (2H),
MS (ESI+): 244 (M+H).

Example 1

N-(2-furo[3,2-c]pyrazolo[1,5-a]pyridin-1-ylethyl)propanamide

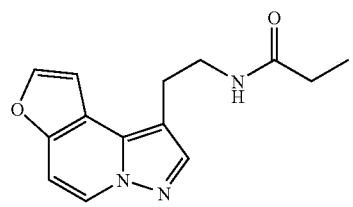

To a mixture of 2-furo[3,2-c]pyrazolo[1,5-a]pyridin-1-ylethanamine (55.5 mg, 0.276 mmol) and triethylamine (117 μL, 0.839 mmol) in tetrahydrofuran (5 mL) was added propionic anhydride (54.0 μL, 0.421 mmol) under ice-cooling, and the mixture was stirred at room temperature for 30 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=50/50→80/20) and recrystallization (ethyl acetate/hexane) to give the title compound (29.0 mg, yield 41%).

$^1$H-NMR (CDCl$_3$) δ: 1.11 (3H, t, J=7.6 Hz), 2.15 (2H, q, J=7.6 Hz), 3.09 (2H, t, J=7.2 Hz), 3.49-3.59 (2H, m), 5.59 (1H, s), 7.01 (1H, d, J=7.6 Hz), 7.29-7.32 (1H, m), 7.71 (1H, d, J=1.9 Hz), 7.81 (1H, s), 8.29 (1H, d, J=7.6 Hz), melting point: 104-106° C. (recrystallized from ethyl acetate/hexane),

MS (ESI+): 258 (M+H),

Elemental analysis: for C$_{14}$H$_{15}$N$_3$O$_2$

Calculated (%): C, 65.35; H, 5.88; N, 16.33

Found (%): C, 65.23; H, 5.79; N, 16.49.

Example 2

N-[2-(2-phenylfuro[3,2-c]pyrazolo[1,5-a]pyridin-1-yl)ethyl]propanamide

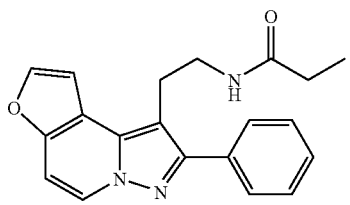

To a mixture of 2-(2-phenylfuro[3,2-c]pyrazolo[1,5-a]pyridin-1-yl)ethanamine hydrochloride (80.0 mg, 0.255 mmol) and triethylamine (142 μL, 1.02 mmol) in tetrahydrofuran (5 mL) was added propionic anhydride (49.0 μL, 0.416 mmol) under ice-cooling, and the mixture was stirred for 30 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=10/90→50/50) and recrystallization (ethyl acetate/hexane) to give the title compound (20.0 mg, yield 24%).

$^1$H-NMR (CDCl$_3$) δ: 1.06 (3H, t, J=7.7 Hz), 2.06 (2H, q, J=7.7 Hz), 3.20-3.27 (2H, m), 3.45-3.54 (2H, m), 5.56 (1H, s), 7.03 (1H, dd, J=7.4, 0.8 Hz), 7.38-7.53 (4H, m), 7.69-7.74 (3H, m), 8.32 (1H, d, J=7.4 Hz), melting point: 161-163° C. (recrystallized from ethyl acetate/hexane),

MS (ESI+): 334 (M+H),

Elemental analysis: for C$_{20}$H$_{19}$N$_3$O$_2$

Calculated (%): C, 72.05; H, 5.74; N, 12.60

Found (%): C, 71.86; H, 5.61; N, 12.59.

Example 3

N-[2-(8,9-dihydrofuro[3,2-c]pyrazolo[1,5-a]pyridin-1-yl)ethyl]acetamide

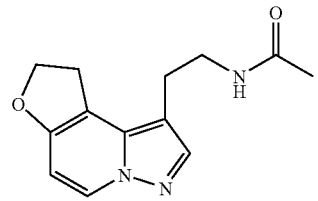

To a solution of 2-(8,9-dihydrofuro[3,2-c]pyrazolo[1,5-a]pyridin-1-yl)ethanamine (75.0 mg, 0.369 mmol) and triethylamine (105 μL, 0.753 mmol) in tetrahydrofuran (4 mL) was added acetic anhydride (70.0 μL, 0.741 mmol) under ice-cooling, and the mixture was stirred at room temperature for 1 hr. A saturated aqueous sodium hydrogen carbonate solution (50 μL) was added to the reaction solution, and the solvent was evaporated under reduced pressure. The residue was purified by silica gel column chromatography (methanol/ethyl acetate=0/100→5/95) and recrystallization (ethyl acetate/diisopropyl ether) to give the title compound (42.1 mg, yield 47%).

$^1$H-NMR (CDCl$_3$) δ: 1.96 (3H, s), 2.91 (2H, t, J=7.0 Hz), 3.41-3.55 (4H, m), 4.74 (2H, t, J=9.1 Hz), 5.57 (1H, brs), 6.47 (1H, d, J=7.6 Hz), 7.73 (1H, s), 8.20-8.26 (1H, m), melting point: 174-175° C. (recrystallized from ethyl acetate/diisopropyl ether),

MS (ESI+): 246 (M+H),

Elemental analysis: for C$_{13}$H$_{15}$N$_3$O$_2$

Calculated (%): C, 63.66; H, 6.16; N, 17.13

Found (%): C, 63.40; H, 6.09; N, 17.27.

Example 4

N-[2-(8,9-dihydrofuro[3,2-c]pyrazolo[1,5-a]pyridin-1-yl)ethyl]propanamide

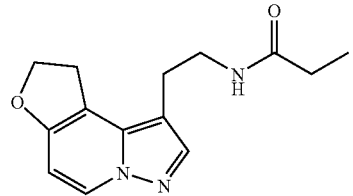

In the same manner as in Example 3, the title compound was obtained (yield 56%) from 2-(8,9-dihydrofuro[3,2-c]pyrazolo[1,5-a]pyridin-1-yl)ethanamine and propionic anhydride.

$^1$H-NMR (CDCl$_3$) δ: 1.13 (3H, t, J=7.6 Hz), 2.17 (2H, q, J=7.6 Hz), 2.91 (2H, t, J=7.2 Hz), 3.41-3.55 (4H, m), 4.74 (2H, t, J=9.1 Hz), 5.55 (1H, brs), 6.47 (1H, d, J=7.6 Hz), 7.72 (1H, s), 8.13-8.31 (1H, m), melting point: 96-97° C. (recrystallized from ethyl acetate/diisopropyl ether),

MS (ESI+): 260 (M+H),

Elemental analysis: for $C_{14}H_{17}N_3O_2$
Calculated (%): C, 64.85; H, 6.61; N, 16.20
Found (%): C, 64.78; H, 6.63; N, 16.20.

Example 5

N-[2-(8,9-dihydrofuro[3,2-c]pyrazolo[1,5-a]pyridin-1-yl)ethyl]butanamide

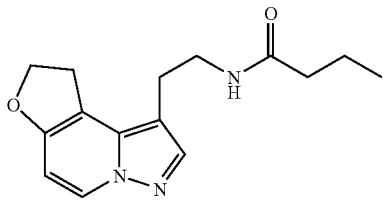

In the same manner as in Example 3, the title compound was obtained (yield 44%) from 2-(8,9-dihydrofuro[3,2-c]pyrazolo[1,5-a]pyridin-1-yl)ethanamine and butyric anhydride.

$^1$H-NMR (CDCl$_3$) δ: 0.92 (3H, t, J=7.4 Hz), 1.56-1.72 (2H, m), 2.08-2.16 (2H, m), 2.90 (2H, t, J=7.0 Hz), 3.41-3.56 (4H, m), 4.73 (2H, t, J=9.1 Hz), 5.56 (1H, brs), 6.46 (1H, d, J=7.4 Hz), 7.71 (1H, s), 8.22 (1H, d, J=7.4 Hz), melting point: 58-59° C. (recrystallized from hexane/ethyl acetate), MS (ESI+): 274 (M+H),
Elemental analysis: for $C_{15}H_{19}N_3O_2 \cdot 0.8H_2O$
Calculated (%): C, 62.61; H, 7.22; N, 14.60
Found (%): C, 62.58; H, 7.26; N, 14.42.

Example 6

N-[2-(2-ethyl-8,9-dihydrofuro[3,2-c]pyrazolo[1,5-a]pyridin-1-yl)ethyl]acetamide

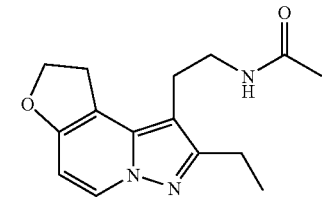

To a solution of 2-(2-ethyl-8,9-dihydrofuro[3,2-c]pyrazolo[1,5-a]pyridin-1-yl)ethanamine (110 mg, 0.476 mmol) and triethylamine (133 μL, 0.954 mmol) in tetrahydrofuran (5 mL) was added acetic anhydride (90.0 μL, 0.952 mmol) under ice-cooling, and the mixture was stirred at room temperature for 1 hr. A saturated aqueous sodium hydrogen carbonate solution (50 μL) was added to the reaction solution, and the solvent was evaporated under reduced pressure. The residue was purified by silica gel column chromatography (ethyl acetate/hexane=90/10→100/0) and recrystallization (ethyl acetate/diisopropyl ether) to give the title compound (67.8 mg, yield 52%).

$^1$H-NMR (CDCl$_3$) δ: 1.34 (3H, t, J=7.7 Hz), 1.95 (3H, s), 2.75 (2H, q, J=7.7 Hz), 2.84 (2H, t, J=7.3 Hz), 3.33-3.42 (2H, m), 3.48 (2H, t, J=9.1 Hz), 4.71 (2H, t, J=9.1 Hz), 5.57 (1H, brs), 6.38 (1H, d, J=7.4 Hz), 8.15 (1H, d, J=7.4 Hz), melting point: 161-162° C. (recrystallized from ethyl acetate/diisopropyl ether), MS (ESI+): 274 (M+H),
Elemental analysis: for $C_{15}H_{19}N_3O_2$
Calculated (%): C, 65.91; H, 7.01; N, 15.37
Found (%): C, 65.76; H, 7.06; N, 15.39.

Example 7

N-[2-(2-ethyl-8,9-dihydrofuro[3,2-c]pyrazolo[1,5-a]pyridin-1-yl)ethyl]propanamide

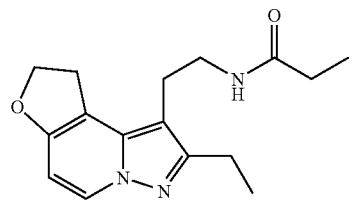

In the same manner as in Example 6, the title compound was obtained (yield 35%) from 2-(2-ethyl-8,9-dihydrofuro[3,2-c]pyrazolo[1,5-a]pyridin-1-yl)ethanamine and propionic anhydride.

$^1$H-NMR (CDCl$_3$) δ: 1.14 (3H, t, J=7.7 Hz), 1.34 (3H, t, J=7.7 Hz), 2.17 (2H, q, J=7.7 Hz), 2.76 (2H, q, J=7.7 Hz), 2.82-2.89 (2H, m), 3.34-3.43 (2H, m), 3.49 (2H, t, J=9.1 Hz), 4.72 (2H, t, J=9.1 Hz), 5.56 (1H, s), 6.39 (1H, d, J=7.4 Hz), 8.13-8.19 (1H, m), melting point: 155-156° C. (recrystallized from diisopropyl ether/ethyl acetate), MS (ESI+): 288 (M+H),
Elemental analysis: for $C_{16}H_{21}N_3O_2$
Calculated (%): C, 66.88; H, 7.37; N, 14.62
Found (%): C, 66.89; H, 7.34; N, 14.59.

Example 8

N-[2-(2-phenyl-8,9-dihydrofuro[3,2-c]pyrazolo[1,5-a]pyridin-1-yl)ethyl]propanamide

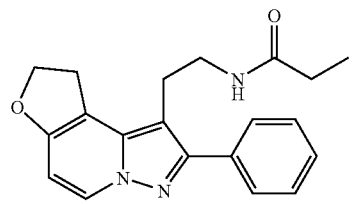

To a mixture of 2-(2-phenyl-8,9-dihydrofuro[3,2-c]pyrazolo[1,5-a]pyridin-1-yl)ethanamine hydrochloride (107 mg, 0.339 mmol) and triethylamine (233 μL, 1.67 mmol) in tetrahydrofuran (10 mL) was added propionic anhydride (110 μL, 0.858 mmol) under ice-cooling, and the mixture was stirred at room temperature for 30 min. A saturated aqueous sodium hydrogen carbonate solution was added to the reaction solution, and the mixture was extracted with ethyl acetate. The extract was dried over anhydrous sodium sulfate. The solvent was evaporated under reduced pressure and the residue was purified by silica gel column chromatography (ethyl acetate/hexane=30/70→60/40) and recrystallization (ethyl acetate/diisopropyl ether) to give the title compound (64.4 mg, yield 57%).

$^1$H-NMR (CDCl$_3$) δ: 1.03 (3H, t, J=7.4 Hz), 2.01 (2H, q, J=7.4 Hz), 3.06 (2H, t, J=7.1 Hz), 3.30-3.39 (2H, m), 3.59 (2H, t, J=9.1 Hz), 4.75 (2H, t, J=9.1 Hz), 5.44 (1H, brs), 6.48 (1H, d, J=7.4 Hz), 7.36-7.50 (3H, m), 7.66-7.72 (2H, m), 8.24 (1H, d, J=7.4 Hz), melting point: 169-170° C. (recrystallized from ethyl acetate/diisopropyl ether),
MS (ESI+): 336 (M+H),
Elemental analysis: for C$_{20}$H$_{21}$N$_3$O$_2$
Calculated (%): C, 71.62; H, 6.31; N, 12.53
Found (%): C, 71.54; H, 6.21; N, 12.60.

Example 9

N-[2-(2-methyl-8,9-dihydrofuro[3,2-c]pyrazolo[1,5-a]pyridin-1-yl)ethyl]acetamide

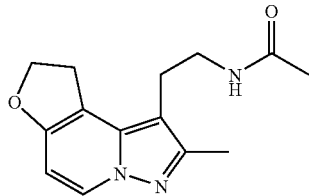

In the same manner as in Example 6, the title compound was obtained (yield 81%) from 2-(2-methyl-8,9-dihydrofuro[3,2-c]pyrazolo[1,5-a]pyridin-1-yl)ethanamine and acetic anhydride.

$^1$H-NMR (CDCl$_3$) δ: 1.95 (3H, s), 2.38 (3H, s), 2.84 (2H, t, J=7.2 Hz), 3.32-3.52 (4H, m), 4.72 (2H, t, J=9.1 Hz), 5.56 (1H, brs), 6.38 (1H, d, J=7.4 Hz), 8.13 (1H, d, J=7.4 Hz), melting point: 158-159° C. (recrystallized from ethyl acetate/diisopropyl ether),
MS (ESI+): 260 (M+H),
Elemental analysis: for C$_{14}$H$_{17}$N$_3$O$_2$·0.3H$_2$O
Calculated (%): C, 63.52; H, 6.70; N, 15.87
Found (%): C, 63.61; H, 6.71; N, 15.78.

Example 10

N-[2-(2-methyl-8,9-dihydrofuro[3,2-c]pyrazolo[1,5-a]pyridin-1-yl)ethyl]propanamide

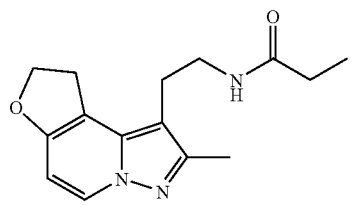

In the same manner as in Example 6, the title compound was obtained (yield 46%) from 2-(2-methyl-8,9-dihydrofuro[3,2-c]pyrazolo[1,5-a]pyridin-1-yl)ethanamine and propionic anhydride.

$^1$H-NMR (CDCl$_3$) δ: 1.13 (3H, t, J=7.7 Hz), 2.17 (2H, q, J=7.7 Hz), 2.38 (3H, s), 2.84 (2H, t, J=7.1 Hz), 3.33-3.52 (4H, m), 4.71 (2H, t, J=9.1 Hz), 5.53 (1H, brs), 6.37 (1H, d, J=7.1 Hz), 8.10-8.14 (1H, m), melting point: 161-162° C. (recrystallized from ethyl acetate/diisopropyl ether),
MS (ESI+): 274 (M+H),
Elemental analysis: for C$_{15}$H$_{19}$N$_3$O$_2$
Calculated (%): C, 65.91; H, 7.01; N, 15.37
Found (%): C, 65.67; H, 6.86; N, 15.53.

Example 11

N-[2-(2-cyclopropyl-8,9-dihydrofuro[3,2-c]pyrazolo[1,5-a]pyridin-1-yl)ethyl]acetamide

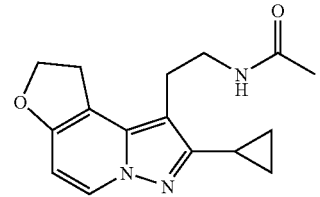

In the same manner as in Example 6, the title compound was obtained (yield 52%) from 2-(2-cyclopropyl-8,9-dihydrofuro[3,2-c]pyrazolo[1,5-a]pyridin-1-yl)ethanamine and acetic anhydride.

$^1$H-NMR (CDCl$_3$) δ: 0.95-1.04 (4H, m), 1.87-2.02 (4H, m), 2.94 (2H, t, J=7.0 Hz), 3.39-3.50 (4H, m), 4.71 (2H, t, J=9.1 Hz), 5.61 (1H, brs), 6.35 (1H, d, J=7.4 Hz), 8.06-8.10 (1H, m), melting point: 149-150° C. (recrystallized from ethyl acetate/diisopropyl ether),
MS (ESI+): 286 (M+H),
Elemental analysis: for C$_{16}$H$_{19}$N$_3$O$_2$
Calculated (%): C, 67.35; H, 6.71; N, 14.73
Found (%): C, 67.10; H, 6.59; N, 14.83.

Example 12

N-[2-(2-cyclopropyl-8,9-dihydrofuro[3,2-c]pyrazolo[1,5-a]pyridin-1-yl)ethyl]propanamide

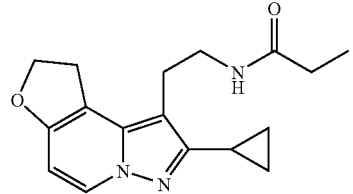

In the same manner as in Example 6, the title compound was obtained (yield 33%) from 2-(2-cyclopropyl-8,9-dihydrofuro[3,2-c]pyrazolo[1,5-a]pyridin-1-yl)ethanamine and propionic anhydride.

$^1$H-NMR (CDCl$_3$) δ: 0.93-1.05 (4H, m), 1.13 (3H, t, J=7.7 Hz), 1.87-1.99 (1H, m), 2.17 (2H, q, J=7.7 Hz), 2.94 (2H, t, J=7.0 Hz), 3.41-3.50 (4H, m), 4.70 (2H, t, J=9.1 Hz), 5.59 (1H, brs), 6.35 (1H, d, J=7.4 Hz), 8.05-8.10 (1H, m), melting point: 164-165° C. (recrystallized from ethyl acetate/diisopropyl ether),
MS (ESI+): 300 (M+H),
Elemental analysis: for C$_{17}$H$_{21}$N$_3$O$_2$
Calculated (%): C, 68.20; H, 7.07; N, 14.04

Found (%): C, 67.96; H, 7.02; N, 14.22.

Example 13

N-{2-[2-(trifluoromethyl)-8,9-dihydrofuro[3,2-c]pyrazolo[1,5-a]pyridin-1-yl]ethyl}acetamide

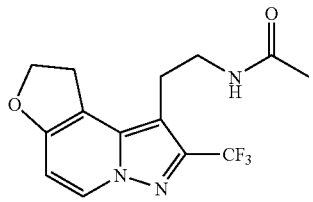

To a solution of 2-[2-(trifluoromethyl)-8,9-dihydrofuro[3,2-c]pyrazolo[1,5-a]pyridin-1-yl]ethanamine (70 mg, 0.26 mmol) and triethylamine (72 μL, 0.52 mmol) in tetrahydrofuran (3 mL) was added acetyl chloride (22 μL, 0.31 mmol) under ice-cooling, and the mixture was stirred at room temperature for 1 hr. The reaction solution was diluted with saturated aqueous sodium hydrogen carbonate solution, and the mixture was extracted with ethyl acetate. The extract was dried over anhydrous magnesium sulfate and the solvent was evaporated under reduced pressure. The residue was purified by silica gel column chromatography (ethyl acetate/hexane=70/30→100/0) and recrystallization (ethyl acetate/hexane) to give the title compound (61.8 mg, yield 76%).

$^1$H-NMR (CDCl$_3$) δ: 1.97 (3H, s), 2.92-3.07 (2H, m), 3.31-3.48 (2H, m), 3.62 (2H, t, J=9.2 Hz), 4.79 (2H, t, J=9.2 Hz), 5.71 (1H, s), 6.63 (1H, d, J=7.7 Hz), 8.25 (1H, d, J=7.7 Hz), melting point: 196-198° C. (recrystallized from ethyl acetate/hexane),

MS (ESI+): 314 (M+H),

Elemental analysis: for C$_{14}$H$_{14}$N$_3$O$_2$F$_3$

Calculated (%): C, 52.76; H, 4.61; N, 13.18

Found (%): C, 52.66; H, 4.51; N, 13.18.

Example 14

N-{2-[2-(trifluoromethyl)-8,9-dihydrofuro[3,2-c]pyrazolo[1,5-a]pyridin-1-yl]ethyl}propanamide

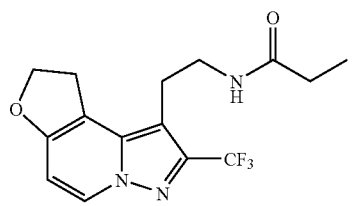

In the same manner as in Example 13, the title compound was obtained (yield 61%) from 2-[2-(trifluoromethyl)-8,9-dihydrofuro[3,2-c]pyrazolo[1,5-a]pyridin-1-yl]ethanamine and propionyl chloride.

$^1$H-NMR (CDCl$_3$) δ: 1.14 (3H, t, J=7.7 Hz), 2.19 (2H, q, J=7.7 Hz), 2.91-3.06 (2H, m), 3.34-3.48 (2H, m), 3.64 (2H, t, J=9.2 Hz), 4.78 (2H, t, J=9.2 Hz), 5.68 (1H, s), 6.63 (1H, d, J=7.4 Hz), 8.25 (1H, d, J=7.4 Hz), melting point: 186-188° C. (recrystallized from ethyl acetate/hexane),

MS (ESI+): 328 (M+H),

Elemental analysis: for C$_{15}$H$_{16}$N$_3$O$_2$F$_3$

Calculated (%): C, 55.04; H, 4.93; N, 12.84

Found (%): C, 54.81; H, 4.82; N, 12.82.

Example 15

N-{2-[2-(4-fluorophenyl)-8,9-dihydrofuro[3,2-c]pyrazolo[1,5-a]pyridin-1-yl]ethyl}acetamide

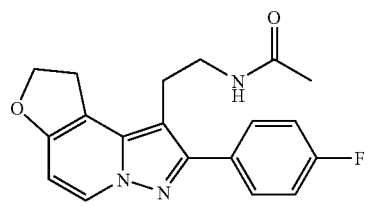

In the same manner as in Example 6, the title compound was obtained (yield 51%) from 2-[2-(4-fluorophenyl)-8,9-dihydrofuro[3,2-c]pyrazolo[1,5-a]pyridin-1-yl]ethanamine hydrochloride and acetic anhydride.

$^1$H-NMR (CDCl$_3$) δ: 1.83 (3H, s), 3.00-3.08 (2H, m), 3.27-3.37 (2H, m), 3.58 (2H, t, J=9.1 Hz), 4.76 (2H, t, J=9.1 Hz), 5.46 (1H, brs), 6.49 (1H, d, J=7.4 Hz), 7.12-7.20 (2H, m), 7.64-7.72 (2H, m), 8.21-8.25 (1H, m), melting point: 160-162° C. (recrystallized from ethyl acetate/diisopropyl ether),

MS (ESI+): 340 (M+H),

Elemental analysis: for C$_{19}$H$_{18}$N$_3$O$_2$F

Calculated (%): C, 67.24; H, 5.35; N, 12.38

Found (%): C, 67.06; H, 5.40; N, 12.32.

Example 16

N-{2-[2-(4-fluorophenyl)-8,9-dihydrofuro[3,2-c]pyrazolo[1,5-a]pyridin-1-yl]ethyl}propanamide

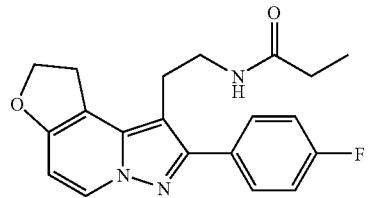

In the same manner as in Example 6, the title compound was obtained (yield 59%) from 2-[2-(4-fluorophenyl)-8,9-dihydrofuro[3,2-c]pyrazolo[1,5-a]pyridin-1-yl]ethanamine hydrochloride and propionic anhydride.

$^1$H-NMR (CDCl$_3$) δ: 1.06 (3H, t, J=7.7 Hz), 2.05 (2H, q, J=7.7 Hz), 3.00-3.08 (2H, m), 3.29-3.38 (2H, m), 3.59 (2H, t, J=9.1 Hz), 4.76 (2H, t, J=9.1 Hz), 5.45 (1H, brs), 6.49 (1H, d, J=7.4 Hz), 7.12-7.20 (2H, m), 7.64-7.72 (2H, m), 8.20-8.25 (1H, m), melting point: 170-171° C. (recrystallized from diisopropyl ether/ethyl acetate),

MS (ESI+): 354 (M+H),

Elemental analysis: for C$_{20}$H$_{20}$N$_3$O$_2$F

Calculated (%): C, 67.97; H, 5.70; N, 11.89
Found (%): C, 67.70; H, 5.73; N, 11.87.

Example 17

N-[2-(8-phenyl-1,2-dihydrofuro[2,3-g]indolizin-9-yl)ethyl]acetamide

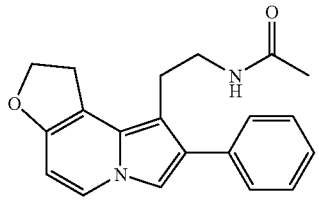

A mixture of N-[3-(2,3-dihydrofuro[3,2-c]pyridin-4-yl)propyl]acetamide (24.5 mg, 0.111 mmol) and 2-bromo-1-phenylethanone (44.2 mg, 0.222 mmol) in acetone (3 mL) was heated under reflux for 13 hr. The reaction mixture was allowed to cool to room temperature and the resulting crystals were collected by filtration and washed with acetone. The crystals were dissolved in ethanol (3 mL), sodium hydrogen carbonate (50 mg) was added, and the mixture was heated under reflux for 1 hr. The reaction mixture was evaporated under reduced pressure, and the residue was purified by silica gel column chromatography (ethyl acetate/hexane=50/50→100/50) to give the title compound (12.7 mg, yield 36%).
$^1$H-NMR (CDCl$_3$) δ: 1.73 (3H, s), 3.07 (2H, t, J=6.9 Hz), 3.19-3.31 (2H, m), 3.51 (2H, t, J=8.9 Hz), 4.66 (2H, t, J=8.9 Hz), 5.32 (1H, brs), 6.30 (1H, d, J=7.1 Hz), 7.23 (1H, s), 7.38-7.52 (5H, m), 7.71 (1H, d, J=7.1 Hz).

Example 18

N-[2-(1,2,6,7-tetrahydro-8H-cyclopenta[d]furo[2,3-b]pyridin-8-ylidene)ethyl]propanamide

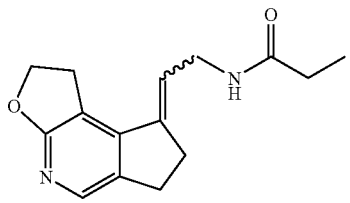

To a solution of 1,2,6,7-tetrahydro-8H-cyclopenta[d]furo[2,3-b]pyridin-8-ylideneacetonitrile (700 mg, 3.53 mmol) in ethanol (24 mL) were added Raney cobalt (4 g) and 2M ammonia/ethanol solution (12 mL), and the mixture was stirred at room temperature for 4 hr under a hydrogen atmosphere. The catalyst was filtered through celite, and the filtrate was evaporated under reduced pressure. The residue was dissolved in dichloromethane (35 mL), triethylamine (984 μL, 7.06 mmol) and propionyl chloride (337 μL, 3.88 mmol) were added under ice-cooling, and the mixture was stirred for 5 min. The reaction solution was diluted with saturated aqueous sodium hydrogen carbonate solution, the mixture was extracted with ethyl acetate, and the extract was washed with saturated brine. The solvent was evaporated under reduced pressure. The residue was purified by silica gel column chromatography (methanol/ethyl acetate=0/100→10/90) to give the title compound. The obtained title compound was used for the reaction of Example 22 without purification.
$^1$H-NMR (CDCl$_3$) δ: 1.19 (3H, t, J=7.4 Hz), 2.25 (2H, q, J=7.4 Hz), 2.80-2.87 (2H, m), 2.92-3.00 (2H, m), 3.30 (2H, t, J=8.7 Hz), 4.03-4.10 (2H, m), 4.65 (2H, t, J=8.7 Hz), 5.63 (1H, brs), 5.83-5.93 (1H, m), 7.89 (1H, s).

Example 19

N-[2-(1,6,7,8-tetrahydro-2H-cyclopenta[d]furo[2,3-b]pyridin-8-yl)ethyl]acetamide

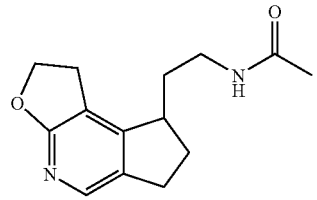

2-(1,2,6,7-Tetrahydro-8H-cyclopenta[d]furo[2,3-b]pyridin-8-ylidene)ethanamine obtained in Reference Example 62 was dissolved in dichloromethane (4 mL), triethylamine (119 μL, 0.856 mmol) and acetyl chloride (30.4 μL, 0.428 mmol) were added under ice-cooling, and the mixture was stirred for 5 min. A saturated aqueous sodium hydrogen carbonate solution was added to the reaction solution, and the solvent was evaporated under reduced pressure. The residue was purified by silica gel column chromatography (methanol/ethyl acetate=0/100→415/85) and dissolved in methanol (3 mL). Palladium-carbon powder (10 mg) was added, and the mixture was stirred at room temperature for 3 hr under a hydrogen atmosphere. The catalyst was filtered off, and the filtrate was evaporated under reduced pressure. The residue was purified by silica gel column chromatography (methanol/ethyl acetate=0/100→15/85) to give the title compound (70.8 mg, total yield from Reference Example 62, 67%).
$^1$H-NMR (CDCl$_3$) δ: 1.55-1.66 (1H, m), 1.75-1.91 (1H, m), 1.98 (3H, s), 2.01-2.16 (1H, m), 2.20-2.39 (1H, m), 2.67-2.94 (2H, m), 3.08-3.39 (5H, m), 4.47-4.69 (2H, m), 5.58 (1H, brs), 7.79 (1H, s),
MS (ESI+): 247 (M+H).

Example 20 optically active N-[2-(1,6,7,8-tetrahydro-2H-cyclopenta[d]furo[2,3-b]pyridin-8-yl)ethyl]acetamide

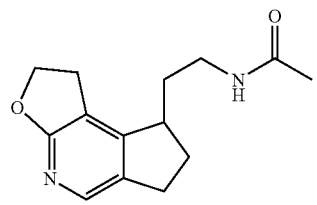

Racemic N-[2-(1,6,7,8-tetrahydro-2H-cyclopenta[d]furo[2,3-b]pyridin-8-yl)ethyl]acetamide (67 mg, 0.272 mmol) was fractioned by high performance liquid chromatography (instrument: Prep LC 2000 (manufactured by Nihon Waters K.K.), column: CHIRALPAK AS (50 mm ID×500 mm L, manufactured by Dicel Chemical Industries, Ltd.), mobile phase: hexane/ethanol/diethylamine=70/30/0.1, flow rate: 60 mL/min, column temperature: 25° C., injection amount: 15 mg). A fraction solution containing an optically active compound having shorter retention time under the above-mentioned high performance liquid chromatography conditions was concentrated. The residue was re-dissolved in ethanol, and the solution was concentrated to dryness. Hexane was added and the mixture was concentrated again to dryness to give the title compound (28 mg, recovery rate 80%).

$^1$H-NMR (CDCl$_3$) δ: 1.54-1.68 (1H, m), 1.73-1.88 (1H, m), 1.98 (3H, s), 2.00-2.16 (1H, m), 2.22-2.38 (1H, m), 2.69-2.98 (2H, m), 3.08-3.43 (5H, m), 4.47-4.69 (2H, m), 5.54 (1H, brs), 7.81 (1H, s),

MS (ESI+): 247 (M+H).

Example 21 optically active N-[2-(1,6,7,8-tetrahydro-2H-cyclopenta[d]furo[2,3-b]pyridin-8-yl)ethyl]acetamide

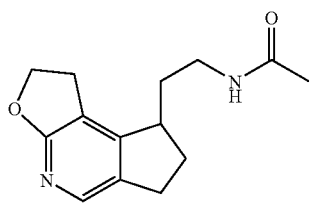

Racemic N-[2-(1,6,7,8-tetrahydro-2H-cyclopenta[d]furo[2,3-b]pyridin-8-yl)ethyl]acetamide (67 mg, 0.272 mmol) was fractioned by high performance liquid chromatography (instrument: Prep LC 2000 (manufactured by Nihon Waters K.K.), column: CHIRALPAK AS (50 mm ID×500 mm L, manufactured by Dicel Chemical Industries, Ltd.), mobile phase: hexane/ethanol/diethylamine=70/30/0.1, flow rate: 60 mL/min, column temperature: 25° C., injection amount: 15 mg). A fraction solution containing an optically active compound having longer retention time under the above-mentioned high performance liquid chromatography conditions was concentrated. The residue was re-dissolved in ethanol, and the solution was concentrated to dryness. Hexane was added and the mixture was concentrated again to dryness to give the title compound (29 mg, recovery rate 87%).

$^1$H-NMR (CDCl$_3$) δ: 1.54-1.71 (1H, m), 1.73-1.89 (1H, m), (3H, s), 1.99-2.15 (1H, m), 2.22-2.38 (1H, m), 2.67-2.96 (2H, m), 3.05-3.41 (5H, m), 4.46-4.69 (2H, m), 5.54 (1H, brs), 7.81 (1H, s),

MS (ESI+): 247 (M+H).

Example 22

N-[2-(1,6,7,8-tetrahydro-2H-cyclopenta[d]furo[2,3-b]pyridin-8-yl)ethyl]propanamide

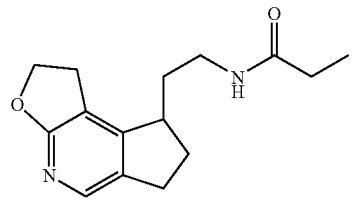

N-[2-(1,2,6,7-tetrahydro-8H-cyclopenta[d]furo[2,3-b]pyridin-8-ylidene)ethyl]propanamide obtained in Example 18 was dissolved in ethanol (20 mL), palladium-carbon powder (60 mg) was added, and the mixture was stirred at room temperature for 2.5 hr under a hydrogen atmosphere. The catalyst was filtered off, and the filtrate was evaporated under reduced pressure. The residue was purified by silica gel column chromatography (methanol/ethyl acetate=0/100→10/90) to give the title compound (517 mg, total yield from Example 18, 56%).

$^1$H-NMR (CDCl$_3$) δ: 1.14 (3H, t, J=7.5 Hz), 1.54-1.70 (1H, m), 1.73-1.88 (1H, m), 1.97-2.13 (1H, m), 2.19 (2H, q, J=7.5 Hz), 2.25-2.36 (1H, m), 2.66-2.94 (2H, m), 3.06-3.45 (5H, m), 4.45-4.69 (2H, m), 5.67 (1H, brs), 7.77 (1H, s).

Example 23 optically active N-[2-(1,6,7,8-tetrahydro-2H-cyclopenta[d]furo[2,3-b]pyridin-8-yl)ethyl]propanamide

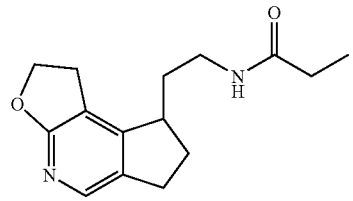

Racemic N-[2-(1,6,7,8-tetrahydro-2H-cyclopenta[d]furo[2,3-b]pyridin-8-yl)ethyl]propanamide (515 mg, 2.17 mmol) was fractioned by high performance liquid chromatography (instrument: Prep LC 2000 (manufactured by Nihon Waters K.K.), column: CHIRALPAK AS (50 mm ID×500 mm L, manufactured by Dicel Chemical Industries, Ltd.), mobile phase: hexane/ethanol/diethylamine=84/16/0.1, flow rate: 60 mL/min→90 mL/min, column temperature: 25° C., injection amount: 128 mg). A fraction solution containing an optically active compound having shorter retention time under the above-mentioned high performance liquid chromatography conditions was concentrated. The residue was re-dissolved in ethanol, and the solution was concentrated to dryness. Hexane was added and the mixture was concentrated again to dryness to give the title compound (237 mg, recovery rate 92%).

$^1$H-NMR (CDCl$_3$) δ: 1.16 (3H, t, J=7.4 Hz), 1.56-1.71 (1H, m), 1.74-1.90 (1H, m), 1.99-2.13 (1H, m), 2.20 (2H, q, J=7.4

Hz), 2.25-2.40 (1H, m), 2.69-2.94 (2H, m), 3.07-3.41 (5H, m), 4.46-4.72 (2H, m), 5.50 (1H, brs), 7.80 (1H, s),
MS (ESI+): 261 (M+H).

Example 24 optically active N-[2-(1,6,7,8-tetrahydro-2H-cyclopenta[d]furo[2,3-b]pyridin-8-yl)ethyl]propanamide

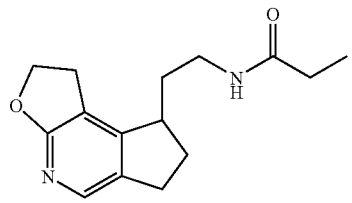

Racemic N-[2-(1,6,7,8-tetrahydro-2H-cyclopenta[d]furo[2,3-b]pyridin-8-yl)ethyl]propanamide (515 mg, 2.17 mmol) was fractioned by high performance liquid chromatography (instrument: Prep LC 2000 (manufactured by Nihon Waters K.K.), column: CHIRALPAK AS (50 mm ID×500 mm L, manufactured by Dicel Chemical Industries, Ltd.), mobile phase: hexane/ethanol/diethylamine=84/16/0.1, flow rate: 60 mL/min→90 mL/min, column temperature: 25° C., injection amount: 128 mg). A fraction solution containing an optically active compound having longer retention time under the above-mentioned high performance liquid chromatography conditions was concentrated. The residue was re-dissolved in ethanol, and the solution was concentrated to dryness. Hexane was added and the mixture was concentrated again to dryness to give the title compound (241 mg, recovery rate 93%).
$^1$H-NMR (CDCl$_3$) δ: 1.16 (3H, t, J=7.7 Hz), 1.57-1.70 (1H, m), 1.75-1.90 (1H, m), 2.00-2.13 (1H, m), 2.20 (2H, q, J=7.7 Hz), 2.25-2.38 (1H, m), 2.69-2.94 (2H, m), 3.08-3.39 (5H, m), 4.50-4.67 (2H, m), 5.49 (1H, brs), 7.80 (1H, s),
MS (ESI+): 261 (M+H).

Example 25

N-[2-(1,6,7,8-tetrahydro-2H-cyclopenta[d]furo[2,3-b]pyridin-8-yl)ethyl]butanamide

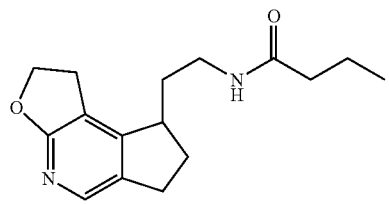

One-eighth (about 0.32 mmol) of 2-(1,6,7,8-tetrahydro-2H-cyclopenta[d]furo[2,3-b]pyridin-8-yl)ethanamine obtained in Reference Example 63 was dissolved in tetrahydrofuran (3 mL), triethylamine (87.9 μL, 0.630 mmol) and butyryl chloride (32.7 μL, 0.315 mmol) were added under ice-cooling, and the mixture was stirred for 15 min. The reaction solution was diluted with saturated aqueous sodium hydrogen carbonate solution, the mixture was extracted with ethyl acetate, and the extract was washed with saturated brine. The solvent was evaporated under reduced pressure and the residue was purified by silica gel column chromatography (methanol/ethyl acetate=0/100→10/90) to give the title compound (30.0 mg).
$^1$H-NMR (CDCl$_3$) δ: 0.95 (3H, t, J=7.3 Hz), 1.55-1.88 (4H, m), 2.00-2.19 (3H, m), 2.22-2.39 (1H, m), 2.68-2.95 (2H, m), 3.07-3.41 (5H, m), 4.46-4.69 (2H, m), 5.57 (1H, brs), 7.79 (1H, s),
MS (ESI+): 275 (M+H).

Example 26

N-[2-(1,6,7,8-tetrahydro-2H-cyclopenta[d]furo[2,3-b]pyridin-8-yl)ethyl]cyclopropanecarboxamide

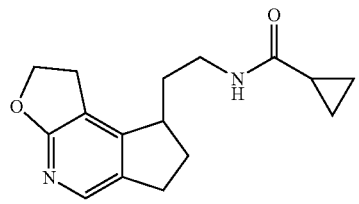

One-eighth (about 0.32 mmol) of 2-(1,6,7,8-tetrahydro-2H-cyclopenta[d]furo[2,3-b]pyridin-8-yl)ethanamine obtained in Reference Example 63 was dissolved in tetrahydrofuran (3 mL), triethylamine (87.9 μL, 0.630 mmol) and cyclopropanecarbonyl chloride (28.6 μL, 0.315 mmol) were added under ice-cooling, and the mixture was stirred for 15 min. The reaction solution was diluted with saturated aqueous sodium hydrogen carbonate solution, the mixture was extracted with ethyl acetate, and the extract was washed with saturated brine. The solvent was evaporated under reduced pressure and the residue was purified by silica gel column chromatography (methanol/ethyl acetate=0/100→10/90) to give the title compound (5.3 mg).
$^1$H-NMR (CDCl$_3$) δ: 0.65-0.83 (2H, m), 0.89-1.04 (2H, m), 1.19-1.38 (1H, m), 1.55-1.92 (2H, m), 1.98-2.15 (1H, m), 2.22-2.40 (1H, m), 2.67-2.97 (2H, m), 3.06-3.45 (5H, m), 4.45-4.72 (2H, m), 5.72 (1H, brs), 7.80 (1H, s).

Example 27

N-[2-(1,6,7,8-tetrahydro-2H-cyclopenta[d]furo[2,3-b]pyridin-8-yl)ethyl]benzamide

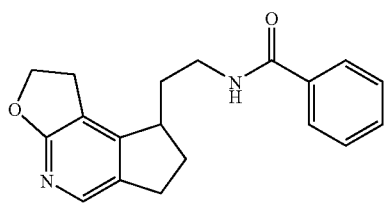

One-eighth (about 0.32 mmol) of 2-(1,6,7,8-tetrahydro-2H-cyclopenta[d]furo[2,3-b]pyridin-8-yl)ethanamine obtained in Reference Example 63 was dissolved in tetrahydrofuran (3 mL), triethylamine (87.9 μL, 0.630 mmol) and benzoyl chloride (36.6 μL, 0.315 mmol) were added under ice-cooling, and the mixture was stirred for 15 min. The reaction solution was diluted with saturated aqueous sodium hydrogen carbonate solution, the mixture was extracted with ethyl acetate, and the extract was washed with saturated brine. The solvent was evaporated under reduced pressure and the residue was purified by silica gel column chromatography (methanol/ethyl acetate=0/100→10/90) to give the title compound (22.3 mg).

¹H-NMR (CDCl₃) δ: 1.69-1.96 (2H, m), 2.14-2.27 (1H, m), 2.28-2.44 (1H, m), 2.71-2.97 (2H, m), 3.09-3.40 (3H, m), 3.49-3.63 (2H, m), 4.48-4.66 (2H, m), 6.23 (1H, brs), 7.37-7.56 (3H, m), 7.68-7.77 (2H, m), 7.81 (1H, s),

MS (ESI+): 309 (M+H).

Example 28

N-ethyl-N'-[2-(1,6,7,8-tetrahydro-2H-cyclopenta[d]furo[2,3-b]pyridin-8-yl)ethyl]urea

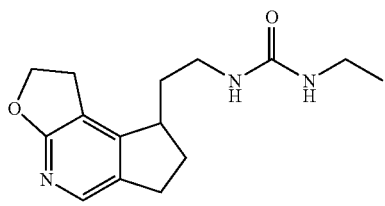

One-eighth (about 0.32 mmol) of 2-(1,6,7,8-tetrahydro-2H-cyclopenta[d]furo[2,3-b]pyridin-8-yl)ethanamine obtained in Reference Example 63 was dissolved in tetrahydrofuran (3 mL), ethyl isocyanate (24.9 μL, 0.315 mmol) was added under ice-cooling, and the mixture was stirred for 15 min. The solvent was evaporated under reduced pressure, and the residue was purified by silica gel column chromatography (methanol/ethyl acetate=0/100→10/90) to give the title compound (13.8 mg).

¹H-NMR (CDCl₃) δ: 1.14 (3H, t, J=7.1 Hz), 1.53-1.68 (1H, m), 1.72-1.88 (1H, m), 1.98-2.12 (1H, m), 2.21-2.37 (1H, m), 2.67-2.93 (2H, m), 3.05-3.37 (7H, m), 4.32-4.66 (4H, m), 7.78 (1H, s),

MS (ESI+): 276 (M+H).

Example 29

N-[2-(1,6-dihydro-2H-cyclopenta[d]furo[2,3-b]pyridin-8-yl)ethyl]propanamide

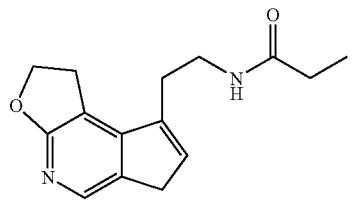

To a solution of N-[2-(1,2,6,7-tetrahydro-8H-cyclopenta[d]furo[2,3-b]pyridin-8-ylidene)ethyl]propanamide (612 mg, 2.37 mmol) in xylene (20 mL) was added sulfuric acid (693 μL, 12.9 mmol), and the mixture was heated under reflux for 22 hr. The reaction solution was diluted with saturated aqueous sodium hydrogen carbonate solution, and the mixture was extracted with ethyl acetate. The extract was washed with saturated brine and dried over anhydrous sodium sulfate. The solvent was evaporated under reduced pressure and the residue was purified by silica gel column chromatography (methanol/ethyl acetate=0/100→10/90) and recrystallization (ethyl acetate) to give the title compound (97.0 mg, yield 16%).

¹H-NMR (CDCl₃) δ: 1.16 (3H, t, J=7.7 Hz), 2.21 (2H, q, J=7.7 Hz), 2.73-2.84 (2H, m), 3.34-3.39 (2H, m), 3.40-3.61 (4H, m), 4.64 (2H, t, J=8.5 Hz), 5.63 (1H, brs), 6.49 (1H, s), 7.99 (1H, s), melting point: 111-112° C. (recrystallized from ethyl acetate),

MS (ESI+): 259 (M+H),

Elemental analysis: for C₁₅H₁₈N₂O₂

Calculated (%): C, 69.74; H, 7.02; N, 10.84

Found (%): C, 69.43; H, 7.05; N, 10.67.

Example 30

N-[2-(7-isopropyl-1,6-dihydro-2H-cyclopenta[d]furo[2,3-b]pyridin-8-yl)ethyl]acetamide

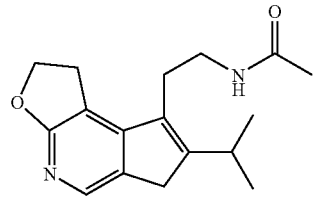

To a solution of 8-(2-aminoethyl)-7-isopropyl-1,6,7,8-tetrahydro-2H-cyclopenta[d]furo[2,3-b]pyridin-8-ol (214 mg, 0.816 mmol) in tetrahydrofuran (8.2 mL) were added triethylamine (228 μL, 1.63 mmol) and acetic anhydride (92.5 μL, 0.979 mmol) under ice-cooling, and the mixture was stirred for 5 min. A saturated aqueous sodium hydrogen carbonate solution was added to the reaction solution, and the solvent was evaporated under reduced pressure. The residue was purified by silica gel column chromatography (methanol/ethyl acetate=0/100→15/85) and dissolved in toluene (10 mL). p-Toluenesulfonic acid monohydrate (478 mg, 2.52 mmol) and magnesium sulfate (900 mg) were added, and the mixture was stirred at 100° C. for 13 hr. The reaction solution was diluted with saturated aqueous sodium hydrogen carbonate solution, and the mixture was extracted with ethyl acetate. The extract was washed with saturated brine and dried over anhydrous sodium sulfate. The solvent was evaporated under reduced pressure and the residue was purified by silica gel column chromatography (methanol/ethyl acetate=0/100→10/90) to give the title compound (37.4 mg, yield 16%).

¹H-NMR (CDCl₃) δ: 1.18 (6H, d, J=6.8 Hz), 1.98 (3H, s), 2.74 (2H, t, J=7.6 Hz), 2.98-3.12 (1H, m), 3.28-3.42 (4H, m), 3.47 (2H, t, J=8.7 Hz), 4.63 (2H, t, J=8.7 Hz), 5.66 (1H, brs), 7.91 (1H, s), melting point: 164-166° C. (recrystallized from ethyl acetate),

MS (ESI+): 287 (M+H),

Elemental analysis: for C₁₇H₂₂N₂O₂

Calculated (%): C, 71.30; H, 7.74; N, 9.78

Found (%): C, 70.73; H, 7.73; N, 9.53.

Example 31

N-[2-(7-isopropyl-1,6-dihydro-2H-cyclopenta[d]furo[2,3-b]pyridin-8-yl)ethyl]propanamide

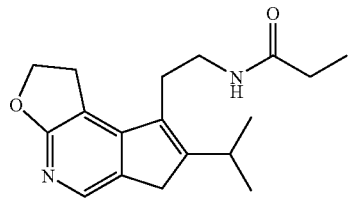

To a solution of 8-(2-aminoethyl)-7-isopropyl-1,6,7,8-tetrahydro-2H-cyclopenta[d]furo[2,3-b]pyridin-8-ol (212 mg, 0.808 mmol) in tetrahydrofuran (8.1 mL) were added triethylamine (225 μL, 1.62 mmol) and propionic anhydride (124 μL, 0.970 mmol) under ice-cooling, and the mixture was stirred for 5 min. A saturated aqueous sodium hydrogen carbonate solution was added to the reaction solution, and the solvent was evaporated under reduced pressure. The residue was purified by silica gel column chromatography (methanol/ethyl acetate=0/100→15/85). The residue was dissolved in toluene (8 mL), p-toluenesulfonic acid monohydrate (364 mg, 1.92 mmol) and magnesium sulfate (700 mg) were added, and the mixture was stirred at 100° C. for 13 hr. The reaction solution was diluted with saturated aqueous sodium hydrogen carbonate solution, and the mixture was extracted with ethyl acetate. The extract was washed with saturated brine and dried over anhydrous sodium sulfate. The solvent was evaporated under reduced pressure and the residue was purified by silica gel column chromatography (methanol/ethyl acetate=0/100→10/90) to give the title compound (80.1 mg, yield 33%).

$^1$H-NMR (CDCl$_3$) δ: 1.10-1.26 (9H, m), 2.20 (2H, q, J=7.5 Hz), 2.74 (2H, t, J=7.5 Hz), 2.99-3.13 (1H, m), 3.28-3.43 (4H, m), 3.48 (2H, t, J=8.5 Hz), 4.63 (2H, t, J=8.5 Hz), 5.64 (1H, brs), 7.91 (1H, s), melting point: 168-170° C. (recrystallized from methanol/ethyl acetate),

MS (ESI+): 301 (M+H),

Elemental analysis: for C$_{18}$H$_{24}$N$_2$O$_2$

Calculated (%): C, 71.97; H, 8.05; N, 9.33

Found (%): C, 71.82; H, 7.92; N, 9.13.

Example 32

N-[(2E)-2-(1,2,6,7-tetrahydro-8H-cyclopenta[b]furo[3,2-d]pyridin-8-ylidene)ethyl]propanamide

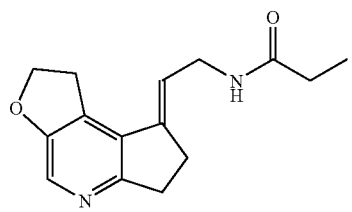

To a mixture of (2E)-2-(1,2,6,7-tetrahydro-8H-cyclopenta[b]furo[3,2-d]pyridin-8-ylidene)ethanamine (220 mg, 0.999 mmol) and triethylamine (167 μL, 1.20 mmol) in dichloromethane (10 mL) was added propionyl chloride (104 μL, 1.20 mmol) under ice-cooling, and the mixture was stirred for 10 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (NH, methanol/ethyl acetate=0/100→10/90) and recrystallization (chloroform/hexane) to give the title compound (195 mg, yield 75%).

$^1$H-NMR (CDCl$_3$) δ: 1.19 (3H, t, J=7.7 Hz), 2.24 (2H, q, J=7.7 Hz), 2.80-2.89 (2H, m), 3.01-3.09 (2H, m), 3.29 (2H, t, J=8.8 Hz), 4.02-4.09 (2H, m), 4.65 (2H, t, J=8.8 Hz), 5.56 (1H, brs), 5.71-5.80 (1H, m), 7.96 (1H, s), melting point: 163-164° C. (recrystallized from chloroform/hexane), Elemental analysis: for C$_{15}$H$_{18}$N$_2$O$_2$ Calculated (%): C, 69.74; H, 7.02; N, 10.84

Found (%): C, 69.58; H, 6.99; N, 10.85.

Example 33

N-[2-(1,6,7,8-tetrahydro-2H-cyclopenta[b]furo[3,2-d]pyridin-8-yl)ethyl]propanamide

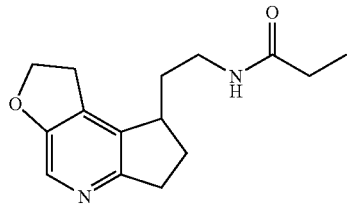

To a solution of N-[(2E)-2-(1,2,6,7-tetrahydro-8H-cyclopenta[b]furo[3,2-d]pyridin-8-ylidene)ethyl]propanamide (65.0 mg, 0.252 mmol) in methanol (1.3 mL) was added palladium-carbon powder (13 mg), and the mixture was stirred at 50° C. for 6 hr under a hydrogen atmosphere. The catalyst was filtered off, and the filtrate was evaporated under reduced pressure. The residue was purified by silica gel column chromatography (ethyl acetate/hexane=50/50→100/0) to give the title compound (39.5 mg, yield 60%).

$^1$H-NMR (CDCl$_3$) δ: 1.15 (3H, t, J=7.7 Hz), 1.59-1.73 (1H, m), 1.77-1.90 (1H, m), 1.98-2.11 (1H, m), 2.19 (2H, q, J=7.7

Hz), 2.27-2.39 (1H, m), 2.78-3.39 (7H, m), 4.48-4.66 (2H, m), 5.48 (1H, brs), 7.91 (1H, s).

Example 34

N-[2-(1,6,7,8-tetrahydro-2H-cyclopenta[b]furo[3,2-d]pyridin-8-yl)ethyl]acetamide

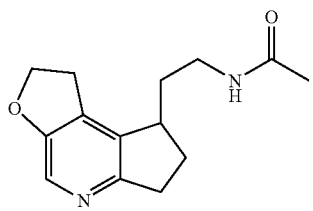

To a solution of (2E)-2-(1,2,6,7-tetrahydro-8H-cyclopenta [b]furo[3,2-d]pyridin-8-ylidene)ethanamine (186 mg, 0.920 mmol) in pyridine (3.7 mL) was added acetyl chloride (78.5 µL, 1.10 mmol) under ice-cooling, and the mixture was stirred for 10 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (ethyl acetate/hexane=50/50→100/0). The residue was dissolved in methanol (1.1 mL), palladium-carbon powder (11 mg) was added, and the mixture was stirred at 50° C. for 3 hr under a hydrogen atmosphere. The catalyst was filtered off, and the filtrate was evaporated under reduced pressure. The residue was purified by silica gel column chromatography (ethyl acetate/hexane=90/10→100/0) to give the title compound (49.1 mg, yield 22%).

$^1$H-NMR (CDCl$_3$) δ: 1.58-1.73 (1H, m), 1.76-1.90 (1H, m), 1.98 (3H, s), 2.01-2.13 (1H, m), 2.27-2.41 (1H, m), 2.79-3.03 (2H, m), 3.06-3.38 (5H, m), 4.50-4.67 (2H, m), 5.62 (1H, brs), 7.92 (1H, s).

Example 35

N-[2-(7-phenyl-1,2-dihydrofuro[2,3-e]imidazo[1,2-a]pyridin-8-yl)ethyl]acetamide

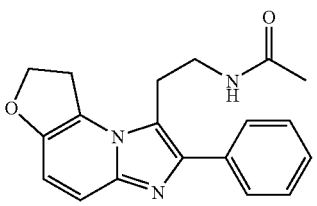

To a solution (5 mL) of (7-phenyl-1,2-dihydrofuro[2,3-e] imidazo[1,2-a]pyridin-8-yl)acetonitrile (17.0 mg, 0.062 mmol) in 2M ammonia/ethanol was added Raney cobalt (500 mg), and the mixture was stirred at room temperature for 2.5 hr under a hydrogen atmosphere. The catalyst was filtered through celite, and the filtrate was concentrated under reduced pressure. The residue was dissolved in tetrahydrofuran (2 mL), triethylamine (17.3 µL, 0.124 mmol) and acetyl chloride (5.3 µL, 0.074 mmol) were added, and the mixture was stirred at room temperature for 20 min. The reaction solution was diluted with saturated aqueous sodium hydrogen carbonate solution, and the mixture was extracted with ethyl acetate. The extract was dried over anhydrous sodium sulfate. The solvent was evaporated under reduced pressure and the residue was purified by silica gel column chromatography (methanol/ethyl acetate=0/100→10/90) and recrystallization (ethyl acetate/hexane) to give the title compound (12.9 mg, yield 65%).

$^1$H-NMR (CDCl$_3$) δ: 1.80 (3H, s), 3.32-3.47 (4H, m), 3.91 (2H, t, J=8.9 Hz), 4.76 (2H, t, J=8.9 Hz), 5.64 (1H, s), 6.96 (1H, d, J=9.3 Hz), 7.29-7.50 (4H, m), 7.65-7.75 (2H, m).

Example 36

N-[2-(2-phenyl-8,9-dihydrofuro[3,2-c]pyrazolo[1,5-a]pyridin-1-yl)ethyl]acetamide

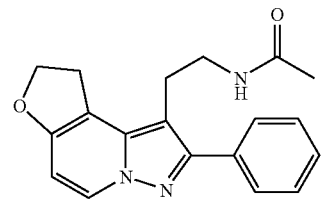

In the same manner as in Example 8, the title compound was obtained (yield 55%) from 2-(2-phenyl-8,9-dihydrofuro [3,2-c]pyrazolo[1,5-a]pyridin-1-yl)ethanamine hydrochloride and acetic anhydride.

$^1$H-NMR (CDCl$_3$) δ: 1.78 (3H, s), 3.06 (2H, t, J=7.1 Hz), 3.28-3.38 (2H, m), 3.57 (2H, t, J=9.1 Hz), 4.76 (2H, t, J=9.1 Hz), 5.43 (1H, brs), 6.48 (1H, d, J=7.4 Hz), 7.35-7.51 (3H, m), 7.65-7.73 (2H, m), 8.22 (1H, d, J=7.4 Hz), melting point: 195-196° C. (recrystallized from ethyl acetate/diisopropyl ether),

MS (ESI+): 322 (M+H),

Elemental analysis: for C$_{19}$H$_{19}$N$_3$O$_2$

Calculated (%): C, 71.01; H, 5.96; N, 13.08

Found (%): C, 70.78; H, 5.91; N, 13.00.

Example 37

N-[2-(2-ethyl-8,9-dihydrofuro[3,2-c]pyrazolo[1,5-a] pyridin-1-yl)propyl]acetamide

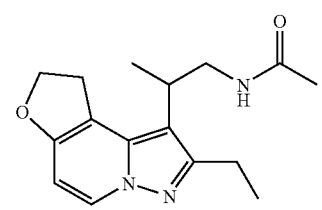

To a solution of 2-(2-ethyl-8,9-dihydrofuro[3,2-c]pyrazolo [1,5-a]pyridin-1-yl)propan-1-amine (118 mg, 0.481 mmol) and triethylamine (134 µL, 0.961 mmol) in tetrahydrofuran (5 mL) was added acetyl chloride (90.9 µL, 0.962 mmol) under ice-cooling, and the mixture was stirred at room temperature for 10 min. A saturated aqueous sodium hydrogen carbonate solution (100 µL) was added and the mixture was concentrated under reduced pressure. The residue was purified by silica gel column chromatography (methanol/ethyl acetate=0/100→5/95) to give the title compound (133 mg, yield 96%).

$^1$H-NMR (CDCl$_3$) δ: 1.29-1.38 (6H, m), 1.87 (3H, s), 2.79 (2H, q, J=7.5 Hz), 3.06-3.33 (2H, m), 3.35-3.52 (2H, m), 3.70-3.82 (1H, m), 4.69 (2H, t, J=9.1 Hz), 5.42 (1H, brs), 6.39 (1H, d, J=7.4 Hz), 8.16 (1H, d, J=7.4 Hz), melting point: 151-153° C. (recrystallized from ethyl acetate/hexane),

MS (ESI+): 288 (M+H),

Elemental analysis: for C$_{16}$H$_{21}$N$_3$O$_2$

Calculated (%): C, 66.88; H, 7.37; N, 14.62

Found (%): C, 66.76; H, 7.17; N, 14.65.

Example 38

N-[2-(2-ethyl-8,9-dihydrofuro[3,2-c]pyrazolo[1,5-a]pyridin-1-yl)propyl]propanamide

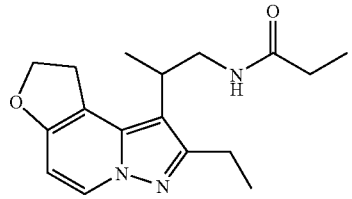

In the same manner as in Example 37, the title compound was obtained (yield 86%) from 2-(2-ethyl-8,9-dihydrofuro[3,2-c]pyrazolo[1,5-a]pyridin-1-yl)propan-1-amine and propionic anhydride.

$^1$H-NMR (CDCl$_3$) δ: 1.05 (3H, t, J=7.5 Hz), 1.31-1.36 (6H, m), 2.03-2.12 (2H, m), 2.80 (2H, q, J=7.5 Hz), 3.06-3.32 (2H, m), 3.35-3.49 (2H, m), 3.73-3.83 (1H, m), 4.62-4.76 (2H, m), 5.38 (1H, brs), 6.39 (1H, d, J=7.4 Hz), 8.13-8.18 (1H, m), melting point: 173-175° C. (recrystallized from ethyl acetate/hexane),

MS (ESI+): 302 (M+H),

Elemental analysis: for C$_{17}$H$_{23}$N$_3$O$_2$

Calculated (%): C, 67.75; H, 7.69; N, 13.94

Found (%): C, 67.60; H, 7.51; N, 13.98.

Example 39

N-[2-(2-ethyl-8-methylfuro[3,2-c]pyrazolo[1,5-a]pyridin-1-yl)ethyl]acetamide

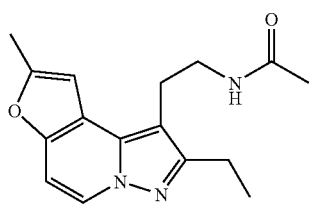

To a solution of 2-(2-ethyl-8-methylfuro[3,2-c]pyrazolo[1,5-a]pyridin-1-yl)ethanamine (100 mg, 0.411 mmol) and triethylamine (85.9 µL, 0.616 mmol) in tetrahydrofuran (4 mL) was added acetyl chloride (58.3 µL, 0.617 mmol) under ice-cooling, and the mixture was stirred at room temperature for 10 min. A saturated aqueous sodium hydrogen carbonate solution (100 µL) was added and the mixture was concentrated under reduced pressure. The residue was purified by silica gel column chromatography (methanol/ethyl acetate=0/100→5/95) and recrystallization (ethyl acetate/hexane) to give the title compound (59.7 mg, yield 51%).

$^1$H-NMR (CDCl$_3$) δ: 1.35 (3H, t, J=7.6 Hz), 1.90 (3H, s), 2.50 (3H, d, J=0.8 Hz), 2.80 (2H, q, J=7.6 Hz), 2.99 (2H, t, J=7.0 Hz), 3.43-3.50 (2H, m), 5.60 (1H, brs), 6.81-6.87 (2H, m), 8.15 (1H, d, J=7.4 Hz), melting point: 128-129° C. (recrystallized from ethyl acetate/hexane),

MS (ESI+): 286 (M+H),

Elemental analysis: for C$_{16}$H$_{19}$N$_3$O$_2$·1.2H$_2$O

Calculated (%): C, 62.60; H, 7.03; N, 13.69

Found (%): C, 62.48; H, 7.08; N, 13.74.

Formulation Example 1

| | |
|---|---|
| (1) Compound obtained in Example 1 | 10.0 g |
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is granulated using 10 wt % aqueous gelatin solution (30 mL) (3.0 g as gelatin) by passing a 1 mm mesh sieve, dried at 40° C. and sieved again. The obtained granules are mixed with magnesium stearate (2.0 g) and the mixture is compressed. The obtained core tablets are coated with a sugar coating using an aqueous suspension of saccharose, titanium dioxide, talc and gum arabic. The coated tablets are glazed with beeswax to give 1000 coated tablets.

Formulation Example 2

| | |
|---|---|
| (1) Compound obtained in Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Melatonin Receptor Binding Inhibitory Test (1) Preparation of CHO-hMelR7 Cells Expressing Human Melatonin 1 Receptors A cDNA fragment (SEQ ID NO: 1) encoding full-length of human melatonin 1 receptors (human MT$_1$ receptors) was incorporated into expression vector pAKKO-111H (former name pAKKO1.11H; Biochim Biophys Acta. Vol. 1219(2), pp. 251-259, 1994) to give plasmid pAKKO-hMelR7 for animal cell expression. CHO/dhfr-cells (ATCC, #CRL-9096)

were plated at a concentration of 0.3×10$^6$ cells/dish in a 6 cm culture dish (Becton Dickinson), and cultured under the conditions of 37° C., 5% CO$_2$ for 48 hr. The cells were transfected with pAKKO-hMelR7 plasmid DNA (5 µg) using Cellphect Transfection Kit (Amersham, #27-9268-01). The transfected cells were cultured in Dulbecco's modified Eagle medium (DMEM) (Sigma, #D6046) containing 10% dialyzed FBS (Biowest, #S180D), 1× Non-Essential Amino Acid (Invitrogen, #11140-050) and 50 µg/mL Gentamycin (Invitrogen, #15750-060), and the cell line that stably expressed the plasmid gene was selected. By a receptor binding assay using 2-[$^{125}$I] Iodomelatonin, CHO-hMelR7 cell line showing specific binding of 2-[$^{125}$I] Iodomelatonin was selected from the obtained clones.

(2) Preparation of CHO-hMT2 Cells Expressing Human Melatonin 2 Receptors

A cDNA fragment (SEQ ID NO: 2) encoding full-length of human melatonin 2 receptors (human MT$_2$ receptors) was incorporated into expression vector pCMV-Script (Stratagene, #212220) to give the plasmid that was pCMV-human MT2 receptors expression vector for animal cell expression. CHO-K1 cells (ATCC, #CCL-61) were plated at the concentration of 1.5×10$^5$ cells/cm$^2$ in a 6 well plate (ASAHI TECHNO GLASS), and cultured under the conditions of 37° C., 5% CO$_2$ for 24 hr. For gene transfection, solution obtained by blending pCMV-human MT2 receptors expression vector (1.9 µg), Lipofectamine Transfection Reagent (Invitrogen, #18324-012) (11.3 µL) and Minimum Essential Medium Eagle (MEM) medium (Sigma, M8042) (93.8 µL), and reacting at room temperature for 20 min was added to the cells per one well. The transfected cells were cultured in MEM medium containing 10% FBS (Life Technology) and 300 µg/mL Geneticin (GIBCO, #10131), and the cell line that stably expressed the plasmid gene was selected. By a receptor binding assay using 2-[$^{125}$I] Iodomelatonin, CHO-hMT2 cell line showing specific binding of 2-[$^{125}$I] Iodomelatonin was selected from the obtained clones.

(3) Preparation of Cellular Membrane Fraction of CHO Cell (CHO-hMelR7 and CHO-hMT2) Stably Expressing Human MT$_1$ and MT$_2$ Receptors CHO-hMelR7 and CHO-hMT2 cells were plated using Cellfactory (Nunc, #170009) under the conditions of 1×10$^8$ cells/2000 mL/flask. The cells were grown to confluent, and recovered by the following method. As the medium for CHO-hMelR7 and CHO-hMT2, MEM α containing 10% FBS and penicillin/streptomycin was used. 300 ng/mL of geneticin was added to the medium for CHO-hMT2.

The medium was discarded, cells were washed twice with 200 mL of EDTA/PBS(−), 200 mL of EDTA/PBS(−) was further added, and the cells were stood still at room temperature for 20 min until they were released. The cells were recovered in four 50 mL tubes (Becton Dickinson, #352070), and centrifuged at 1,500 rpm for 10 min at 4° C. using a low speed cooling centrifuge (Hitachi, CF7D2). The supernatant was discarded, the pellets in the four tubes were suspended in 10 mL of PBS(−), and combined in one tube (Becton Dickinson, #352070). The mixture was further centrifuged at 1,500 rpm for 10 min at 4° C., and the obtained pellets were suspended in 20 mL of ice-cooled homogenizing buffer [10 mM NaHCO$_3$, 5 mM EDTA, Protease inhibitor Complete (Roche), pH 7.4]. The cell suspension was homogenized 3 times using a polytron homogenizer at 20,000 rpm for 30 sec. The obtained homogenate was centrifuged (2,000 rpm, 10 min, 4° C.) using a low speed cooling centrifuge. The supernatant was recovered in an ultracentrifugation tube and ultracentrifuged (40,000 rpm, 60 min, 4° C.) using an ultracentrifuge (Beckman, L-90K). To the obtained pellets was added a suspending buffer [50 mM Tris-HCl, 1 mM EDTA, Protease inhibitor Complete (Roche), pH 7.4], and the pellets were suspended by pipetting. The protein concentration of this suspension was measured, diluted to 2 mg/mL to give cellular membrane fractions of CHO-hMelR7 and CHO-hMT2 cells. The membrane fractions were dispensed to 1.5 mL tubes (Eppendorf, #0030120.086) by 100 µL, preserved in a freezer (−80° C.) and used for a binding assay. Protein was quantified using BCA protein assay kit (Pierce) with BSA as the standard.

(4) Preparation of Membrane Fraction Suspension

Immediately before use, the membrane fractions of CHO-hMelR7 and CHO-hMT2 cells of the above-mentioned (3) were diluted 20-fold with assay buffer (50 mM Tris-HCl, pH 7.7).

(5) Preparation of 2-[$^{125}$I] Iodomelatonin Solution

2-[$^{125}$I] Iodomelatonin (#NEX236, PerkinElmer) was diluted with the assay buffer to 400 pM for MT$_1$ and 1 nM for MT$_2$.

(6) Binding Reaction

The assay buffer (80 µL) of the above-mentioned (4) was added to each well of a 96-well plate (type 3363, Corning). Then, a test compound (compound solution diluted with DMSO to 200-fold of the final measurement concentration) was added by 2 µL. 2 µL of DMSO was added to each well of the total binding control section, and 100 µM cold Melatonin solution (Sigma, diluted with DMSO to 100 µM) was added to each well of the nonspecific binding control section by 2 µL. Then, the membrane fraction suspension (100 µL) was added. 2-[$^{125}$I] Iodomelatonin solution of the above-mentioned (5) was added to each well mentioned above by 20 µL, and a binding reaction was carried out at 25° C. for 2.5 hr in a micromixer (TAITEC, Bioshaker M.BR-024).

(7) Measurement

Using a cell harvester (PerkinElmer), the binding reaction mixture in each well of the 96-well plate was transferred to a treated (immersed in 50 mM Tris, pH 7.7 in advance) filter plate (UniFilter GF/C, PerkinElmer) and filtered. After filtration, the plate was washed 4 times with the assay buffer, and dried in a dryer (42° C.) for 2 hr or more. 25 µL of a liquid scintillator (MicroScint O, PerkinElmer) was added to each well of the filter plate after drying, and the luminescence of scintillator was measured by TopCount (PerkinElmer) for 1 min.

Specific binding is a value obtained by subtracting nonspecific binding from the total binding. The binding inhibitory activity of the test compound is shown by the ratio of the value obtained by subtracting the measurement value when the test compound was added from the total binding, to the specific binding. The compound concentration (IC$_{50}$ value) showing 50% of binding inhibitory activity was calculated from the dose reaction curve.

The binding inhibitory activity of the compound of Examples 2, 3, 4, 5, 6, 7, 8, 9, 10, 11, 12, 13, 14, 15, 16, 17, 19, 20, 22, 23, 25, 26, 29, 30, 31, 35, 36, 37, 38 and 39 was not more than 100 nM as IC$_{50}$ value for MT$_1$.

The binding inhibitory activity of the compound of Examples 1, 2, 3, 4, 5, 6, 7, 8, 9, 10, 11, 12, 13, 14, 15, 16, 17, 20, 22, 23, 25, 29, 30, 31, 35, 36, 37, 38 and 39 was not more than 100 nM as IC$_{50}$ value for MT$_2$.

This application is based on application No. 2006-332647 filed in Japan, the contents of which are incorporated hereinto by reference.

The invention claimed is:

1. A compound represented by the formula:

<chemical structure (I)> wherein
$R^1$ is $C_{1-6}$ alkyl, $C_{3-6}$ cycloalkyl, $C_{6-10}$ aryl or mono-$C_{1-6}$ alkylamino,
$R^2$ is a hydrogen atom or $C_{1-6}$ alkyl,
$R^3$ is a hydrogen atom or $C_{1-6}$ alkyl,
m is 0, 1 or 2,
the tricycle consisting of ring A, ring B and ring C is a ring represented by the formula <chemical structures> wherein ring A optionally has one $C_{1-6}$ alkyl,
ring B is unsubstituted, and
ring C optionally has one substituent at the carbon atom selected from the group consisting of (1) $C_{1-6}$ alkyl optionally having 1 to 3 halogen atoms, (2) $C_{3-6}$ cycloalkyl and (3) $C_{6-10}$ aryl optionally having 1 to 3 halogen atoms, and
------ is a single bond or a double bond,
or a salt thereof.

2. The compound of claim 1, wherein $R^1$ is $C_{1-6}$ alkyl.

3. The compound of claim 1, wherein $R^2$ is a hydrogen atom.

4. The compound of claim 1, wherein $R^3$ is a hydrogen atom.

5. The compound of claim 1, wherein m is 1.

6. The compound of claim 1, wherein
$R^2$ is a hydrogen atom; and
m is 1.

7. N-[2-(8,9-Dihydrofuro[3,2-c]pyrazolo[1,5-a]pyridin-1-yl)ethyl]acetamide, N-[2-(2-ethyl-8,9-dihydrofuro[3,2-c]pyrazolo[1,5-a]pyridin-1-yl)ethyl]acetamide, N-[2-(2-ethyl-8,9-dihydrofuro[3,2-c]pyrazolo[1,5-a]pyridin-1-yl)ethyl]propanamide, N-[2-(2-methyl-8,9-dihydrofuro[3,2-c]pyrazolo[1,5-a]pyridin-1-yl)ethyl]acetamide, N-{2-[2-(trifluoromethyl)-8,9-dihydrofuro[3,2-c]pyrazolo[1,5-a]pyridin-1-yl]ethyl}acetamide, N-[2-(7-phenyl-1,2-dihydrofuro[2,3-e]imidazo[1,2-a]pyridin-8-yl)ethyl]acetamide, N-[2-(2-phenyl-8,9-dihydrofuro[3,2-c]pyrazolo[1,5-a]pyridin-1-yl)ethyl]acetamide, or N-[2-(2-ethyl-8,9-dihydrofuro[3,2-c]pyrazolo[1,5-a]pyridin-1-yl)propyl]acetamide, or a salt thereof.

8. A pharmaceutical composition comprising the compound of claim 1 or a salt thereof, and a pharmacologically acceptable carrier.

9. The pharmaceutical composition of claim 8, which is a melatonin receptor agonist.

10. A compound represented by the formula

<chemical structure> wherein
$R^2$ is a hydrogen atom or $C_{1-6}$ alkyl,
$R^3$ is a hydrogen atom or $C_{1-6}$ alkyl,
m is 0, 1 or 2,
the tricycle consisting of ring A, ring B and ring C is a ring represented by the formula <chemical structures> wherein ring A optionally has one $C_{1-6}$ alkyl,
ring B is unsubstituted, and
ring C optionally has one substituent at the carbon atom selected from the group consisting of (1) $C_{1-6}$ alkyl optionally having 1 to 3 halogen atoms, (2) $C_{3-6}$ cycloalkyl and (3) $C_{6-10}$ aryl optionally having 1 to 3 halogen atoms, and
------ is a single bond or a double bond,
or a salt thereof.

* * * * *